United States Patent
Vishwakarma et al.

(10) Patent No.: US 9,206,201 B2
(45) Date of Patent: Dec. 8, 2015

(54) BORONIC ACID BEARING LIPHAGANE COMPOUNDS AS INHIBITORS OF PI3K-α AND/OR β

(71) Applicant: COUNCIL OF SCIENTIFIC & INDUSTRIAL RESEARCH, New Delhi (IN)

(72) Inventors: Ram Asrey Vishwakarma, Jammu (IN); Sanghapal Damodhar Sawant, Jammu (IN); Parvinder Pal Singh, Jammu (IN); Abid Hamid Dar, Jammu (IN); Parduman Raj Sharma, Jammu (IN); Ajit Kumar Saxena, Jammu (IN); Amit Nargotra, Jammu (IN); Anjaneya Aravind Kumar Kolluru, Jammu (IN); Ramesh Mudududdla, Jammu (IN); Asif Khurshid Qazi, Jammu (IN); Aashiq Hussain, Jammu (IN); Nayan Chanauria, Jammu (IN)

(73) Assignee: Counsel of Scientific & Industrial Research (IN)

( * ) Notice: Subject to any disclaimer, the term of this patent is extended or adjusted under 35 U.S.C. 154(b) by 0 days.

(21) Appl. No.: 14/385,808

(22) PCT Filed: Mar. 18, 2013

(86) PCT No.: PCT/IN2013/000169
§ 371 (c)(1),
(2) Date: Sep. 17, 2014

(87) PCT Pub. No.: WO2013/140417
PCT Pub. Date: Sep. 26, 2013

(65) Prior Publication Data
US 2015/0051173 A1   Feb. 19, 2015

(30) Foreign Application Priority Data
Mar. 19, 2012  (IN) .......................... 0794/DEL/2012

(51) Int. Cl.
*C07F 5/02* (2006.01)
*A61K 31/69* (2006.01)

(52) U.S. Cl.
CPC ................ *C07F 5/025* (2013.01); *A61K 31/69* (2013.01)

(58) Field of Classification Search
None
See application file for complete search history.

(56) References Cited

PUBLICATIONS

International Search Report, Council of Scientific & Industrial Research, PCT/IN2013/000169, Aug. 2, 2013.
Written Opinion of the International Searching Authority, Council of Scientific & Industrial Research, PCT/IN2013/000169, Aug. 2, 2013.
Marion, Frederic et al., Liphagal, a Selective Inhibitor of PI3 Kinase α Isolated from the Sponge Aka coralliphaga: Structure Elucidation and Biomimetic Synthesis, Orginal Letters., vol. 8, No. 2, 2006, pp. 321-324.
Mehta, Goverdhan et al., A concise synthesis of the bioactive meroterpenoid natural product (±)-liphagal, a potent PI3K inhibitor, Tetrahedron Letters 50 (2009), pp. 5260-5262.
Kim, Yeong Gil et al., Aromatic hole injecting or transportingmaterial for organic electroluminescent device, C:\EPOPROGS\SEA\.\..\.. \epodata\sea\eplogf\SA1202753.1og, XP-002704039, 2 pgs. Jul. 19, 2013.
Kawamura, Masahiro et al., Anthracene derivative for organic electroluminescent device, C:\EPOPROGS\SEA\.\..\.. \epodata\sea\eplogf\SA1202753.log, XP-002704040, 3 pgs. Jul. 19, 2013.

*Primary Examiner* — Michael Barker
(74) *Attorney, Agent, or Firm* — McDonald Hopkins LLC

(57) ABSTRACT

Compounds with unique liphagane meroterpenoid scaffold having boronic acid functionality in the skeleton are described (formula 1) together with pharmacological potential of these compounds as anticancer agents. A method of preparation and inhibiting the activity of phosphoinositide-3-kinase (PI3K-alpha and beta) has been presented. In particular, the invention describes a method of inhibiting PI3K isoforms, wherein the compounds are novel structures based on liphagane scaffold with unique boronic acid functionality. The methods and uses thereof are described herein this invention.

18 Claims, 18 Drawing Sheets

Figure 2:
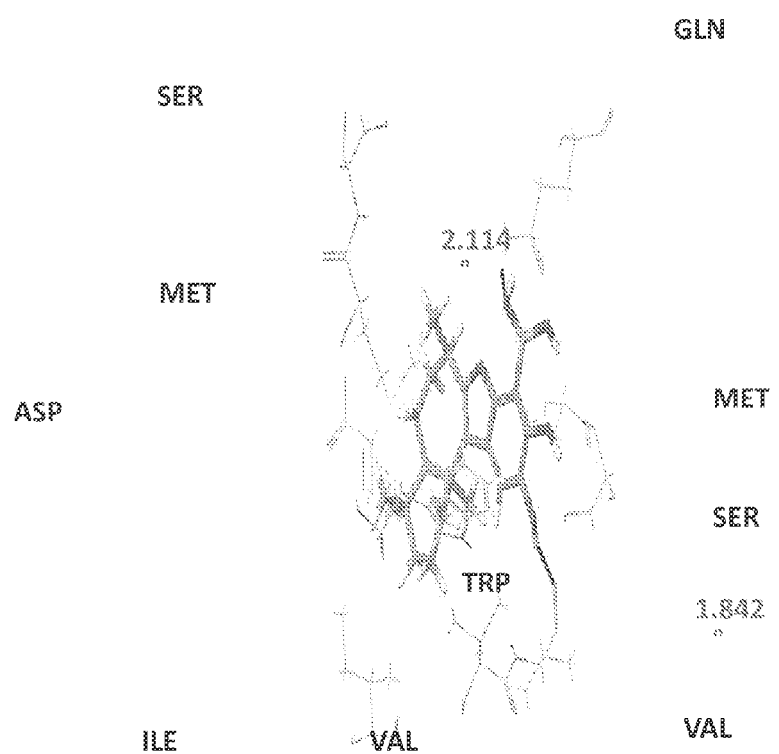

| | Tissue | | Lung | Leukemia | Prostate | Colon | | | Normal Epithelial |
|---|---|---|---|---|---|---|---|---|---|
| | Cell type | | A 549 | THP 1 | PC 3 | Colo 205 | Caco 2 | HCT-116 | fR-2 |
| S.NO | CCL CODE | Conc(uM) | | | | % Growth Inhibition | | | |
| 1 | Compound A | 10uM | 86 | 95 | 89 | 90 | 94 | 74 | 16 |
| | | 1uM | 16 | 13. | 13 | 42 | 41 | 35 | 3 |
| | | 0.1uM | 10 | 24 | 10 | 34 | 31 | 30 | 2 |
| | | 0.01uM | 7 | 30 | 7 | 32 | 24 | 2 | 2 |
| 2 | Compound D | 10uM | 17 | 24 | 7 | 58 | 14 | 20 | 10 |
| | | 1uM | 15 | 23 | 5 | 36 | 4 | 10 | 6 |
| | | 0.1uM | 14 | 22 | 3 | 30 | 3 | 5 | 1 |
| | | 0.01uM | 9 | 11 | 1 | 29 | 1 | 7 | 1 |
| 3 | Compound E | 10uM | 16 | 61 | 9 | 8 | 77 | 67 | 14 |
| | | 1uM | 13 | 48 | 8 | 4 | 20 | 10 | 4 |
| | | 0.1uM | 2 | 18 | 5 | 2 | 14 | 8 | 3 |
| | | 0.01uM | 1 | 3 | 1 | 1 | 2 | 2 | 1 |
| 4 | Compound S | 10uM | 34 | 30 | 10 | 59 | 20 | 42 | 7 |
| | | 1uM | 30 | 24 | 6 | 17 | 19 | 28 | 5 |
| | | 0.1uM | 10 | 10 | 1 | 3 | 12 | 20 | 3 |
| | | 0.01uM | 5 | 4 | 1 | 0 | 2 | 15 | 1 |
| 5 | Compound T | 10uM | 65 | 42 | 15 | 64 | 20 | 34 | 10 |
| | | 1uM | 10 | 25 | 10 | 20 | 10 | 20 | 6 |
| | | 0.1uM | 8 | 25 | 5 | 13 | 5 | 17 | 1 |
| | | 0.01uM | 2 | 2 | 1 | 8 | 7 | 11 | 1 |
| | | 10 | 36 | 25 | 22 | 52 | 39 | 25 | 41 |
| 6 | Compound U | 1 | 24 | 15 | 5 | 15 | 13 | 15 | 19 |
| | | 0.1 | 9 | 12 | 4 | 20 | 1 | 16 | 25 |
| 7 | Compound AD | 10uM | 10 | 42 | 13 | 27 | 25 | 21 | 21 |
| | | 1uM | 5 | 39 | 3 | 22 | 15 | 11 | 11 |
| | | 0.1uM | 2 | 12 | 1 | 10 | 10 | 9 | 9 |
| | | 0.01uM | 0 | 10 | 0 | 5 | 9 | 6 | 6 |
| 8 | Compound AE | 10uM | 30 | 14 | 4 | 27 | 9 | 16 | 22 |
| | | 1uM | 22 | 12 | 1 | 20 | 8 | 14 | 13 |
| | | 0.1uM | 13 | 10 | 1 | 23 | 5 | 8 | 10 |
| | | 0.01uM | 11 | 8 | 1 | 0 | 1 | 5 | 5 |
| 9 | Compound AF | 10uM | 19 | 7 | 6 | 25 | 22 | 27 | 20 |
| | | 1uM | 10 | 5 | 4 | 21 | 20 | 19 | 14 |
| | | 0.1uM | 9 | 2 | 2 | 19 | 18 | 12 | 12 |
| | | 0.01uM | 5 | 1 | 0 | 10 | 16 | 1 | 8 |
| 10 | Compound AG | 10uM | 24 | 21 | 16 | 40 | 10 | 7 | 14 |
| | | 1uM | 15 | 11 | 14 | 37 | 4 | | 12 |
| | | 0.1uM | 10 | 9 | 8 | 31 | 3 | 3 | 10 |
| | | 0.01uM | 3 | 6 | 5 | 23 | 1 | 1 | 8 |
| 11 | Compound AN | 10uM | 13 | 7 | 38 | 20 | 35 | 31 | 17 |

Figure 1

|  |  | 1uM | 11 | 5 | 26 | 14 | 21 | 25 | 15 |
|  |  | 0.1uM | 10 | 3 | 11 | 12 | 3 | 21 | 14 |
|  |  | 0.01uM | 8 | 1 | 7 | 8 | 1 | 14 | 9 |
| 12 | Compound AZ | 10uM | 55 | 87 | 82 | 77 | 86 | 71 | 77 |
|  |  | 1uM | 51 | 79 | 80 | 64 | 81 | 55 | 45 |
|  |  | 0.1uM | 50 | 63 | 71 | 62 | 73 | 51 | 44 |
|  |  | 0.01uM | 48 | 42 | 47 | 58 | 61 | 44 | 39 |
|  | Liphagal | 10uM | 27 | 55 | 25 | 31 | 53 | 34 | 7 |
|  |  | 1uM | 19 | 40 | 15 | 25 | 7 | 25 | 5 |
|  |  | 0.1uM | 12 | 34 | 10 | 21 | 3 | 23 | 2 |

Figure 1 (Continued...)

Reagents and conditions: a) DCC, DMAP, DCM, rt, 18h, b) ii) Et$_3$N, THF, reflux, 5h c) ClSO$_3$H, 2-Nitropropane, -78 °C, 0.5h d) n-BuLi, 0 oC, triethylborate, 45 min b) AlCl$_3$, thiourea, DCM, rt, 2h Table 2: Showing $IC_{50}$ values of PI3K isoforms for compound-AZ

| Compound | PI3K ($IC_{50}$) | | | |
|---|---|---|---|---|
| AZ | α | β | γ | δ |
| | 23 nM | 5.7 µM | 85.39 µM | 303 µM |

Figure 12:
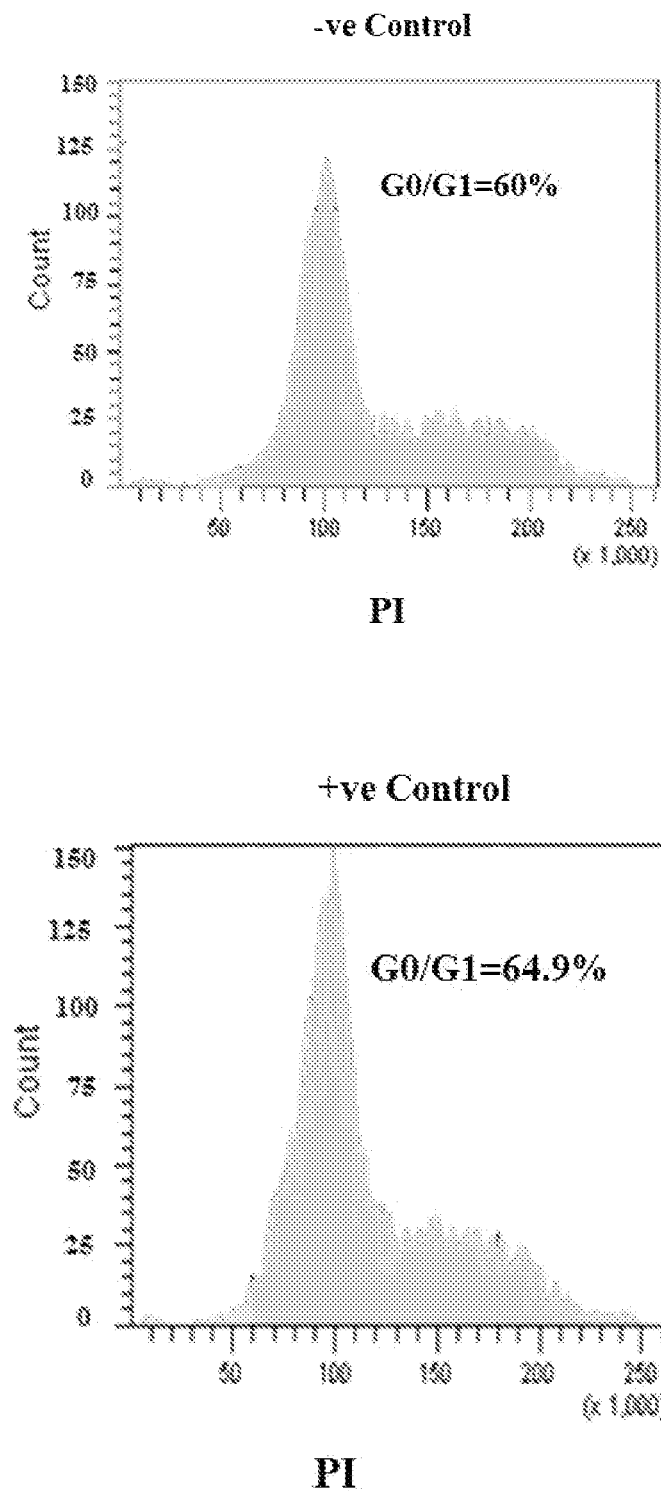

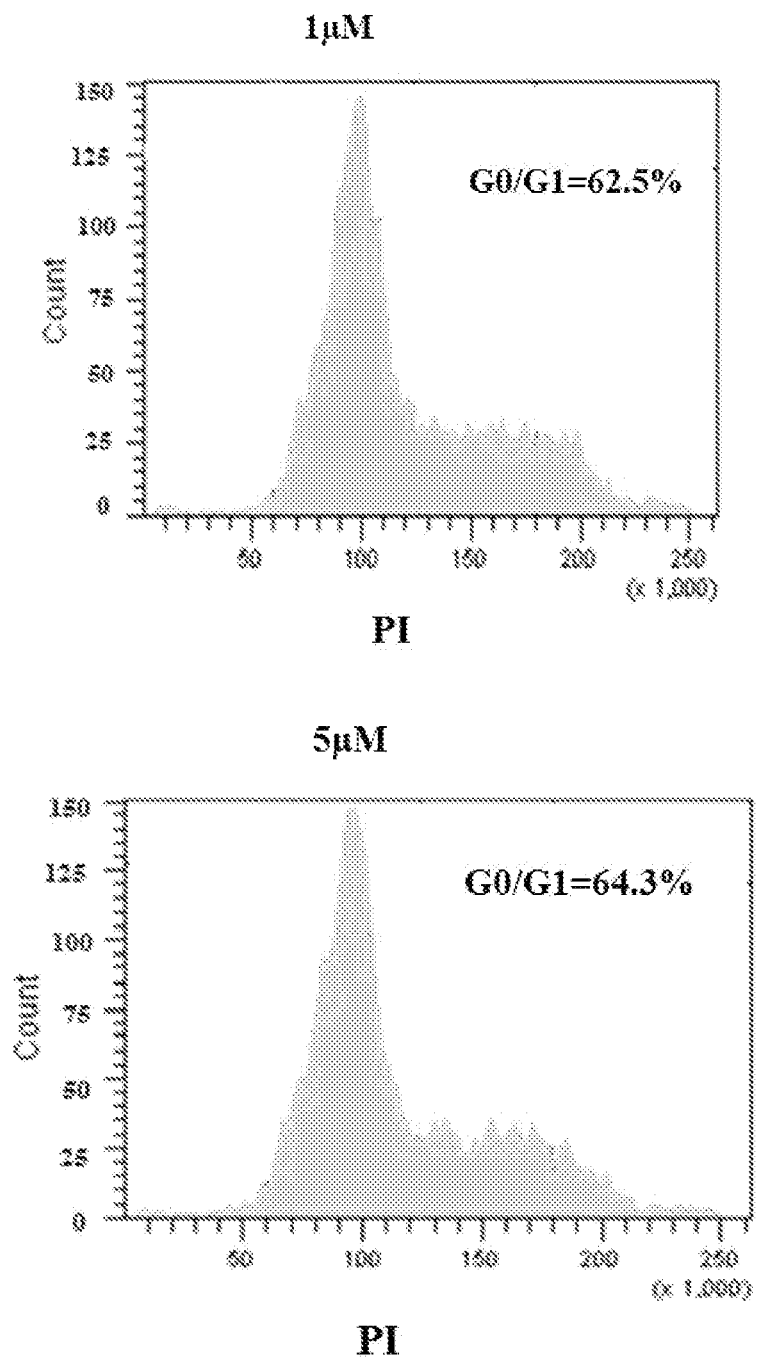
Figure 12 (Continued...)

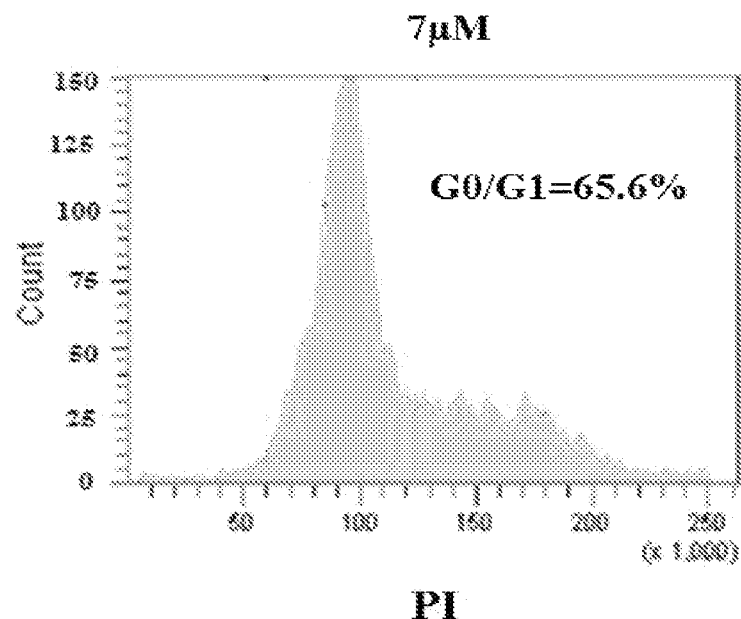
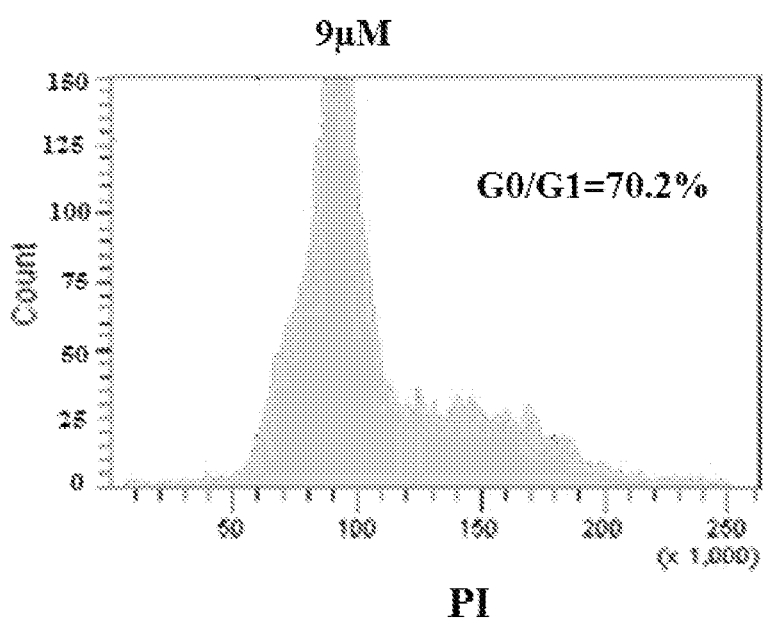
Figure 12 (continued...)

Figure 13:
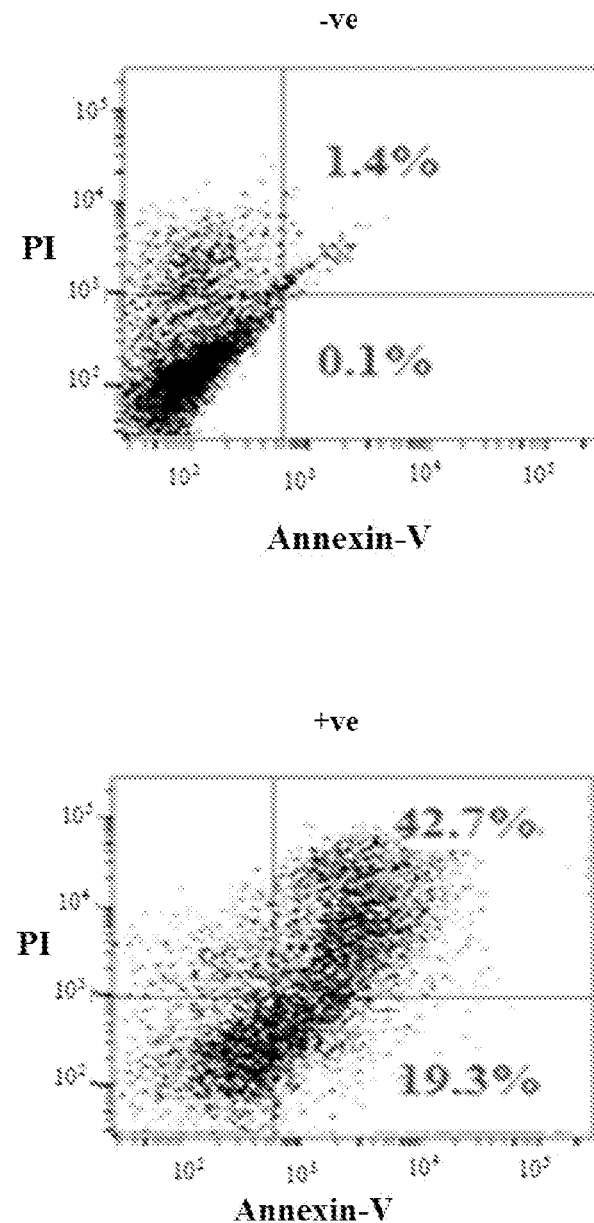

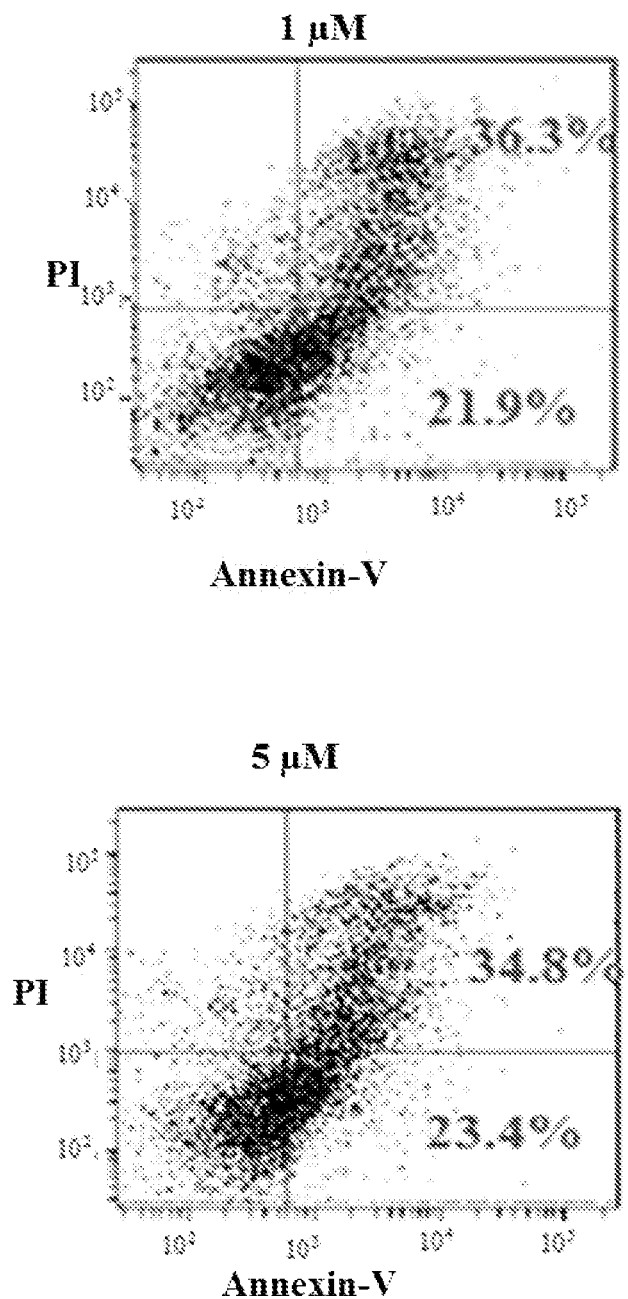
Figure 13 (Continued...)

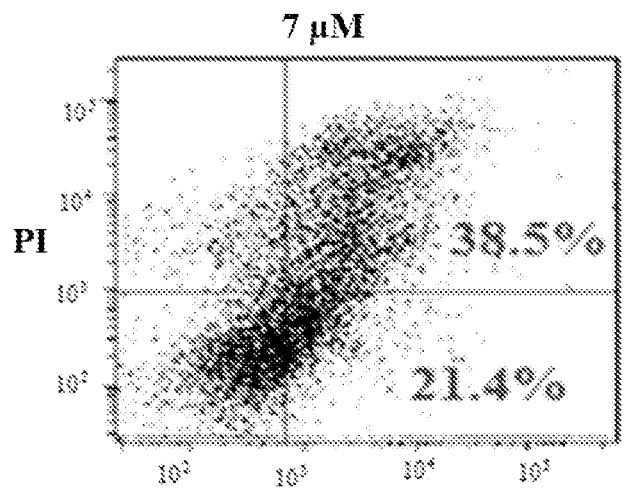
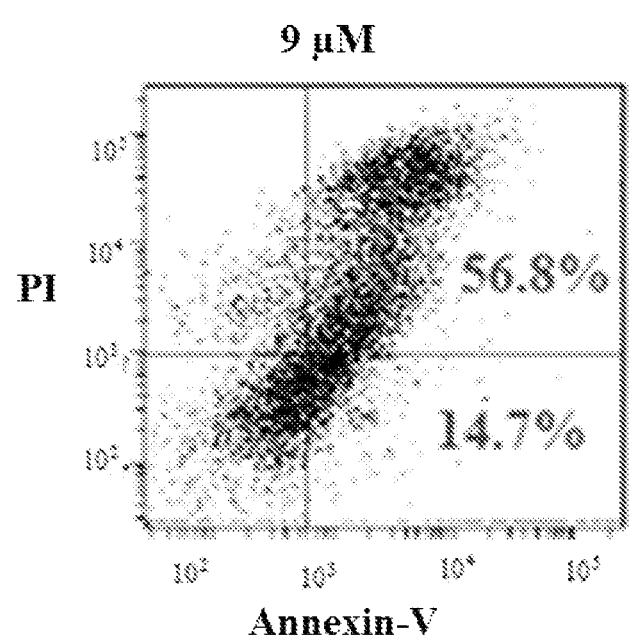
Figure 13 (continued...)

BORONIC ACID BEARING LIPHAGANE COMPOUNDS AS INHIBITORS OF PI3K-α AND/OR β

FIELD OF THE INVENTION

The present invention relates to boronic acid bearing liphagane compounds. The present invention particularly relates to boronic acid bearing meroterpenoid liphagane scaffold based compounds. The compounds have been designed, synthesized and their biological evaluation results for anticancer activity by inhibiting PI3K pathway are presented in this invention. The field of invention for this work relates and covers the development of novel PI3K-α/β inhibitors based on meroterpenoid liphagane scaffold for anticancer activity.

BACKGROUND OF THE INVENTION

PI3Ks are a family of related intracellular signal transducer capable of phosphorylating the 3 position hydroxyl group of the inositol ring of Phosphatidylinositol (PtdIns). They are also known as phosphatidylinositol-3-kinases. The pathway, with oncogene PIK3 and tumor suppressor (PTEN) gene is implicated in insensitivity of cancer tumors to insulin and IGF1, in calorie restriction. 3-kinase (PI3K) signaling pathway is a newly identified strategy for the discovery and development of certain therapeutic agents. Among the various subtypes of PI3K, class IA PI3K-alpha has gained increasing attention as a promising drug target for the treatment of cancer due to its frequent mutations and amplifications in various human cancers. In contrast with cytotoxic agents that do not differentiate between normal proliferating and tumour cells, targeted therapies primarily exert their action in cancer cells. Initiation and maintenance of tumours are due to genetic alterations in specific loci. The identification of the genes in these alterations occurs has opened new opportunities for cancer treatment. The PI3K (phosphoinositide 3-kinase) pathway is often overactive in human cancers and various genetic alteration have been found to cause this. In all cases, PI3K inhibition is considered to be one of the most promising targeted therapies for cancer treatment.

Owing to its widespread activation in inflammation and cancer, a growing appreciation of the therapeutic potential of inhibitors of the phosphoinositide 3-kinase (PI3K) pathway has stimulated intense interest in compounds with suitable pharmacological profiles. These are primarily directed toward PI3K itself. However, as class I PI3Ks are also essential for a range of normal physiological processes, broad spectrum PI3K inhibition could be poorly tolerated.

In recent years, patents describing a new generation of PI3K inhibitors have started to appear, with a particular focus on the development of compounds with enhanced isoform selectivity for use as anti-cancer and anti-inflammatory therapies. However, challenges remain for the efforts to pharmacologically target this enzyme family in a successful manner.

Rationale for the Selection of Phosphoinositide 3-Kinase-α (PI3K-α/β) Inhibitors:—

At cellular level, phosphoinositide-3-kinase signaling contributes to many processes, including cell cycle progression, cell growth, survival and migration and intracellular vesicular transport. The PI3K represents the family of lipid kinases that can be classified into three subfamilies according to structure and substrate specificity viz., class I, class II and class III. The class I PI3Ks are the most extensively studied among lipid kinases, are heterodimeric proteins; each containing a smaller regulatory domain and a larger 110 kDa catalytic domain, which occur in four isoforms differentiated as p110α, p110β, p110γ, and p110δ. Although, there are natural product based small molecules reported in the literature which inhibit the PI3-kinases having the $IC_{50}$ value in nano-gram range (viz., Wortmannin isolated from *Penicillium wortmanni*, LY294002 a synthetic analogue of the flavonoid quercetin, etc) but these molecules did not reach to market because of low potency, poor isoform or kinase selectivity, limited stability and unacceptable pharmacological and pharmacokinetic properties. However, PI3 kinase inhibitors having isoform selectivity and promising drug-like properties have now begun to emerge that show promise for the treatment of cancer and other disease indications. In cancer, evidence suggests that inhibition of the class 1A PI3 kinases p110α and p110β appear to be the most appropriate to target. Recently, Andersen et al., in 2006 reported the potential isoform selective PI3K-alpha inhibitor from marine sponge *Aka coralliphaga* under the collaborative program to screen marine invertabrates against human PI3K-alpha keeping in mind that natural products from marine resources have emerged as a copious repository of molecular diversity and hold considerable promise as a rich source of lead structures in drug discovery. Liphagal (Joshua J. Day, Ryan M. McFadden; The catalytic enantioselective total synthesis of (+)-Liphagal; *Angew. Chem. Int. Ed.* 2011, 50, 6814-6818; Enrique Alvarez-Manzaneda, RachidChahboun; Enantioselectivetotal synthesis of the selective PI3-kinase inhibitor Liphagal; *Org. Lett.*, 2010, 12 (20), pp 4450-4453; Jonathan H. George, Jack E. Baldwin; Enantiospecific biosynthetically inspired formal total synthesis of (+)-Liphagal, *Org. Lett.*, 2010, 12 (10), pp 2394-2397; Alban R. Pereira, Wendy K. Strangman, Synthesis of phosphatidylinositol 3-kinase (PI3K) inhibitory analogues of the sponge meroterpenoid Liphagal; *J. Med Chem.*, 2010, 53 (24), pp 8523-8533; Dima A. Sabbah, Jonathan L. Vennerstrom; Docking studies on isoform-specific inhibition of phosphoinositide-3-kinases; *J. Chem. Inf. Model.*, 2010, 50 (10), pp 1887-1898; Ram Vishwakarma and Sanjay Kumar; Efficient Synthesis of key intermediate toward Liphagal synthesis; *Synthetic Communications;* 2010, 41(2), pp 177-183; Frederic Marion, David E. Williams, Liphagal, a selective inhibitor of PI3 kinase-α isolated from the sponge *Aka coralliphaga*: Structure elucidation and biomimetic synthesis; *Org. Lett.*, 2006, 8 (2), pp 321-324; Goverdhan Mehta, Nachiket S. Likhite, C. S. Ananda Kumar A concise synthesis of the bioactive meroterpenoid natural product (±)-liphagal, a potent PI3K inhibitor, *Tet. Lett*, 2009, vol. 50, no. 37, pp 321-324) was ~10-fold more potent against PI3K-α than against PI3K-γ. We have synthesized boron containing analog of liphagal by rational modification on this molecule following diversity oriented synthesis approach for the discovery of lead molecules.

OBJECTS OF THE PRESENT INVENTION

The main object of the present invention is to provide boronic acid bearing liphagane compounds. Another object of the invention provides a process for preparation of boronic acid functional group containing liphagane compounds.

Yet another object of the present invention is to provide process for the preparation for step A6 to A7 and A7 to A by the synthetic route mentioned in the claims of this invention document.

Still another object of the present invention is to evaluate biological activity of the boronic acid based liphagal compounds as anticancer agents.

Yet another object of the present invention is to identify isoform selectivity of these compounds for PI3K inhibition as alpha or beta specific when studied for enzyme specificity.

Yet another object of the invention is to explore the mechanism of action and growth inhibition of the liphagal boronic acid bearing compound by Annexin-V or immunofluroscent assay and by cell cycle analysis.

SUMMARY OF THE INVENTION

Accordingly the present invention provides a compound of general formula 1, and pharmaceutically acceptable salts thereof,

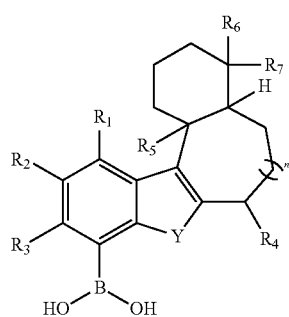

Formula 1 wherein,
- a) 'Y'=O, S, NH or NR, wherein R=alkyl moiety, aryl moiety, heteroaryl moiety cyclic aliphatic ring or aromatic system;
- b) wherein n=0 or 1;
- c) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
  wherein, R, R', R" are independently selected from a group consisting of alkyl moiety, aryl moiety, heteroaryl moiety and cyclic aliphatic ring,
  wherein the cyclic aliphatic ring is selected from a group consisting of cyclopropyl, cyclobutyl, cyclopentyl and cyclohexyl ring and wherein the cyclic aliphatic ring has different substitutions at different positions,
  wherein the alkyl moiety is selected from a group consisting of methyl, ethyl, propyl, isopropyl, butyl and isobutyl,
  and wherein aryl or heteroaryl moiety has substitutions selected from a group consisting of halo, alkyl with different chain length, nitro, amino, and sulphonyl substitutions;
- d) wherein $R_4$=H or OR or SR or $SO_2R$ or $OSO_3R$ or SiRR'R" or $NH_2$ or NHR or NRR' or an alkyl substituent or one to ten carbon chain either linear or branched, saturated or unsaturated alkyl group optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R,
  wherein R, R', R" are independently selected from a group consisting of alkyl moiety, aryl moiety, heteroaryl moiety and cyclic aliphatic ring with different substitutions with varying chain length cyclic aliphatic ring with different substitutions and varying chain length,
  and wherein aryl or heteroaryl moiety has substitutions selected from a group consisting of halo, alkyl with different chain length, nitro, amino, and sulphonyl substitutions;
  wherein the alkyl substituent is selected from a group consisting of methyl, ethyl, propyl and higher homologues,
  wherein the higher homologues are linear, branched or alicyclic substituents,
  wherein the alicyclic substituents are selected from a group consisting of cyclopentane, cyclohexane, higher membered rings, fused rings and aryl/heteroaryl substituted alkyl groups,
  wherein the aryl/heteroaryl substituted alkyl groups are benzylic or unsaturated alkyl groups further selected from a group consisting of cinnamul, crotyl and prenyl substituents;
- e) wherein $R_5$, $R_6$ and $R_7$ are independently selected from a group consisting of H, one to ten carbon chain either linear or branched, saturated or unsaturated at any position, and alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R" and R,
  wherein R, R', R" independently selected from a group consisting of alkyl moiety, aryl moiety, heteroaryl moiety and cyclic aliphatic ring with different substitutions.

In another embodiment of the invention, the compound of general formula 1 is represented by compounds of formula A, B, C, D, E, F, G, H, I, J, K, L, M, N, O, P, Q, R, S, T, U, V, W, X, Y, Z, AA, AB, AC, AD, AE, AF, AG, AH, AI, AJ, AK, AL, AM, AN, AO, AP, AQ, AR, AS, AT, AU, AV, AW, AX, AY and AZ comprising the following structural formula:

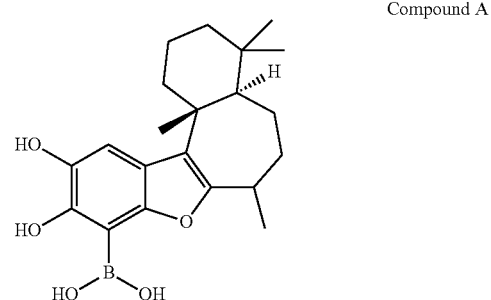

Compound A

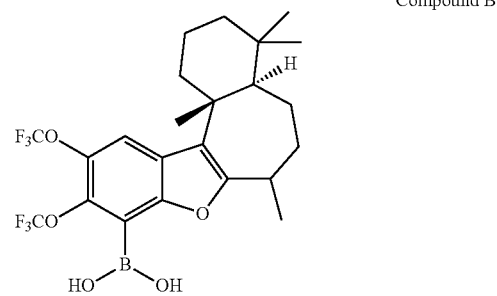

Compound B

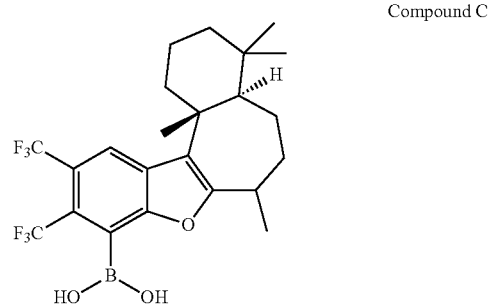

Compound C

Compound D
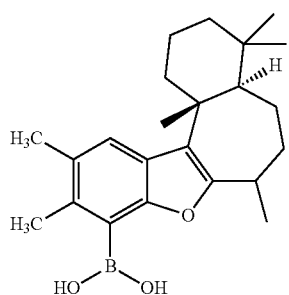
Compound E
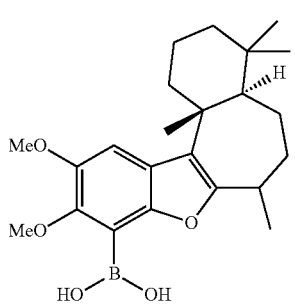
Compound F
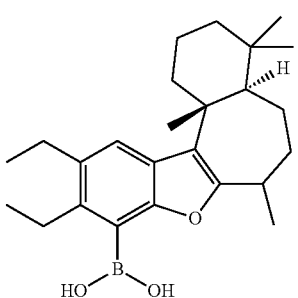
Compound G
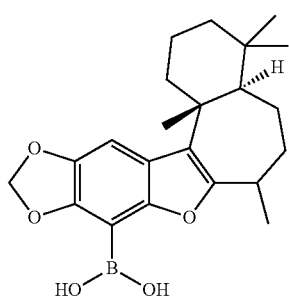
Compound H
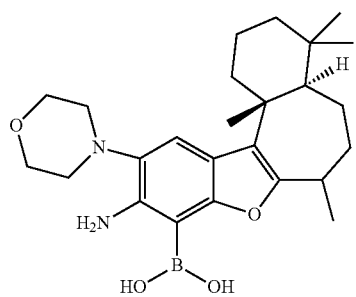
Compound I
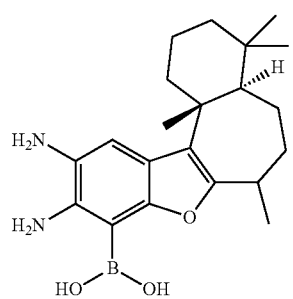
Compound J
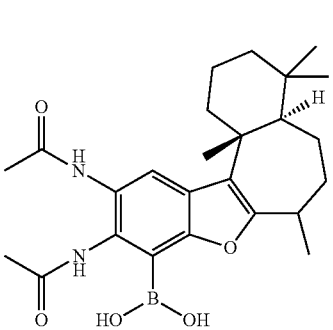
Compound K
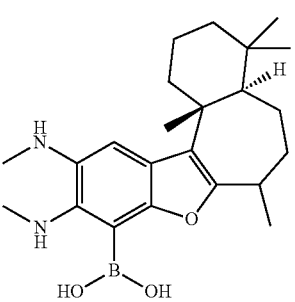
Compound L
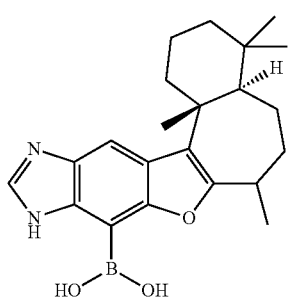
Compound M
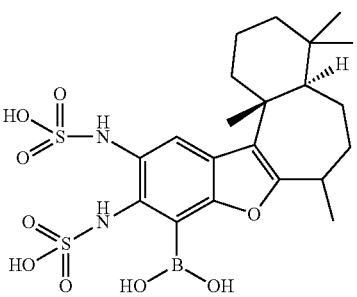

Compound N
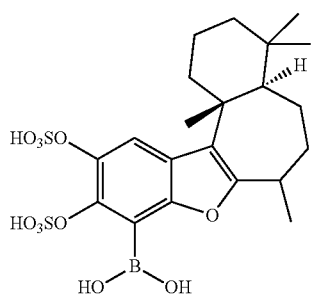
Compound S
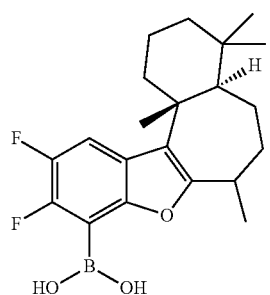
Compound O
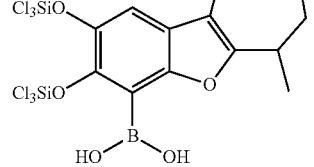
Compund T
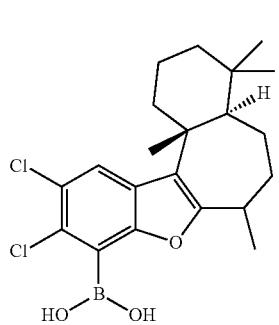
Compound P
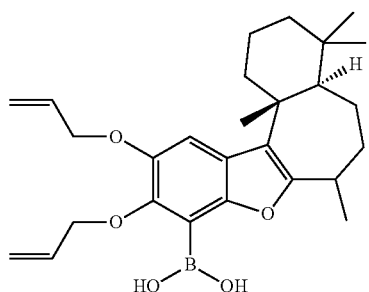
Compound U
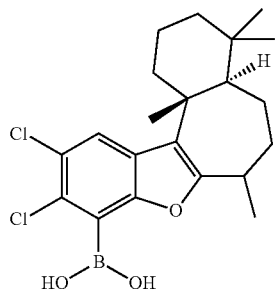
Compound Q
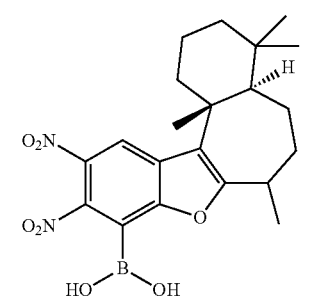
Compound V
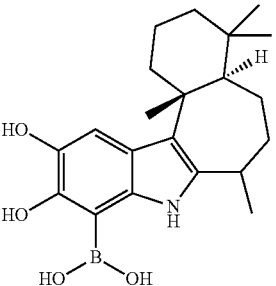
Compound R
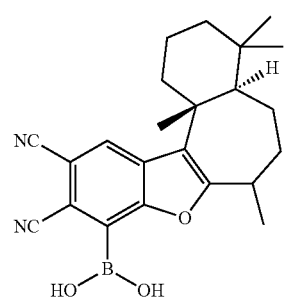
Compound W
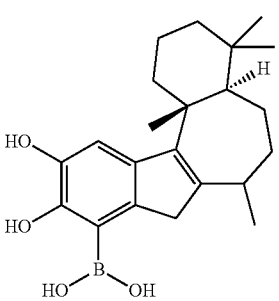

-continued
Compound X
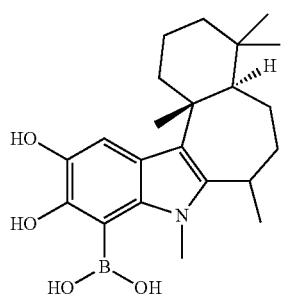
Compound Y
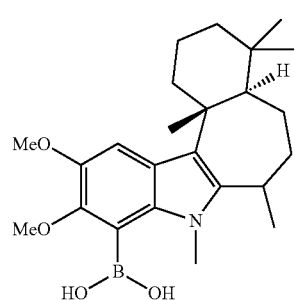
Compound Z
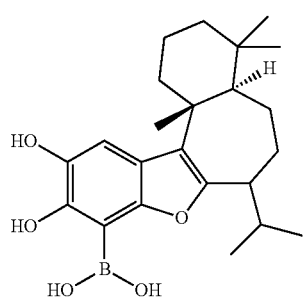
Compound AA
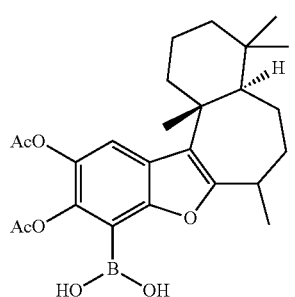
Compound AB
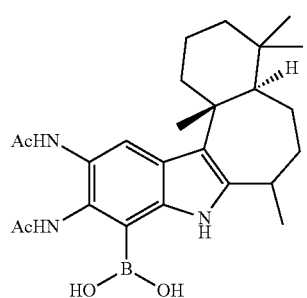
-continued
Compound AC
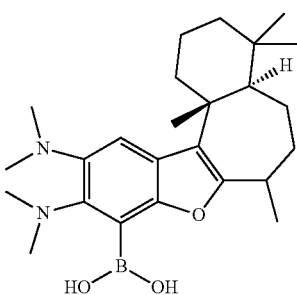
Compound AD
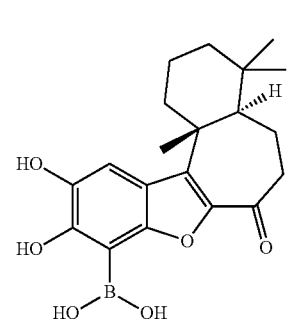
Compound AE
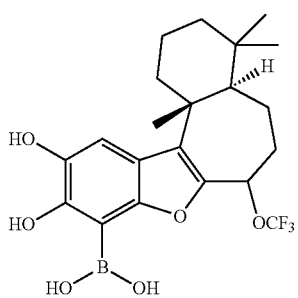
Compound AF
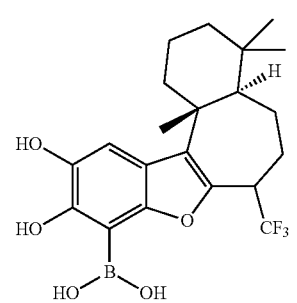
Compound AG
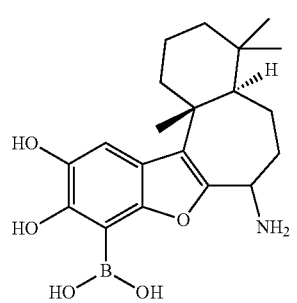

Compound AH
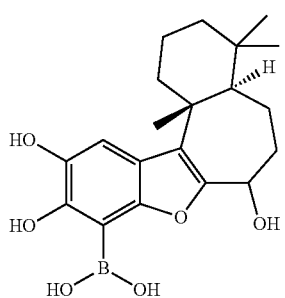
Compound AI
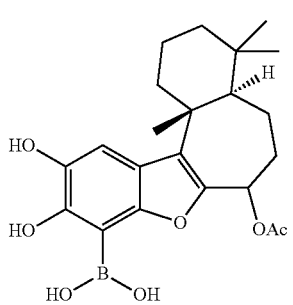
Compound AJ
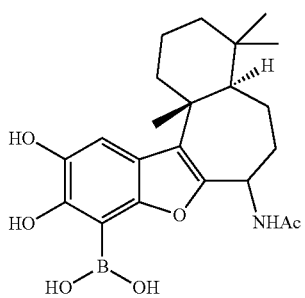
Compound AK
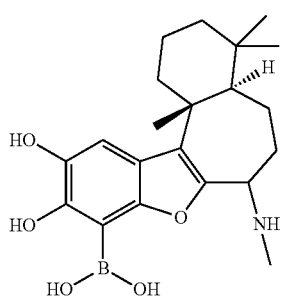
Compound AL
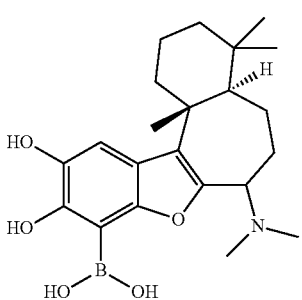
Compound AM
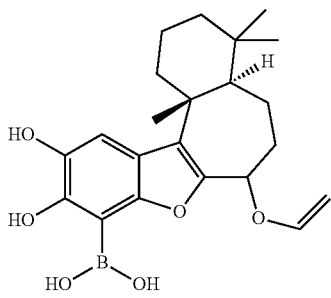
Compound AN
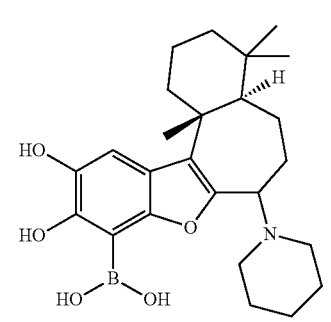
Compound AO
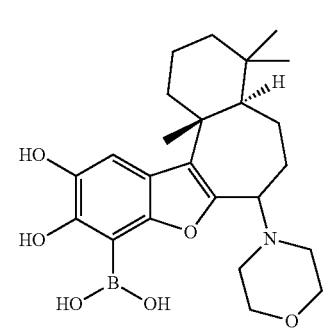
Compound AP
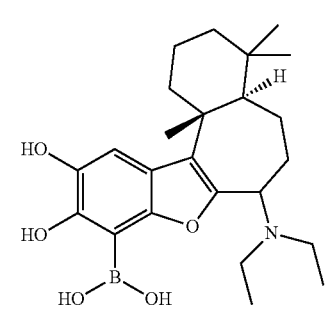
Compound AQ
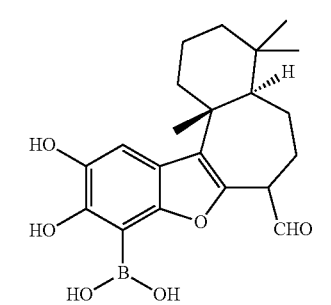

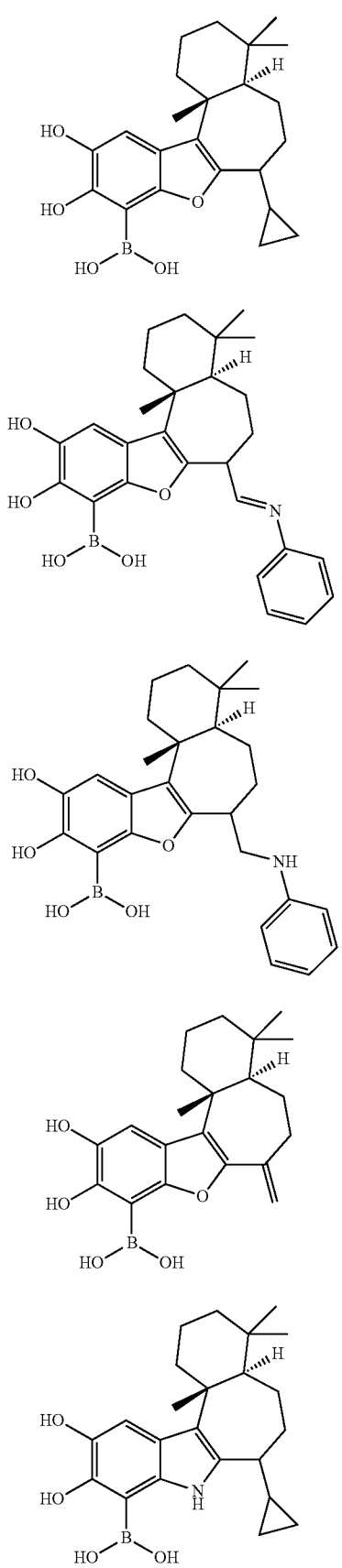

Compound AR

Compound AS

Compound AT

Compound AU

Compound AV

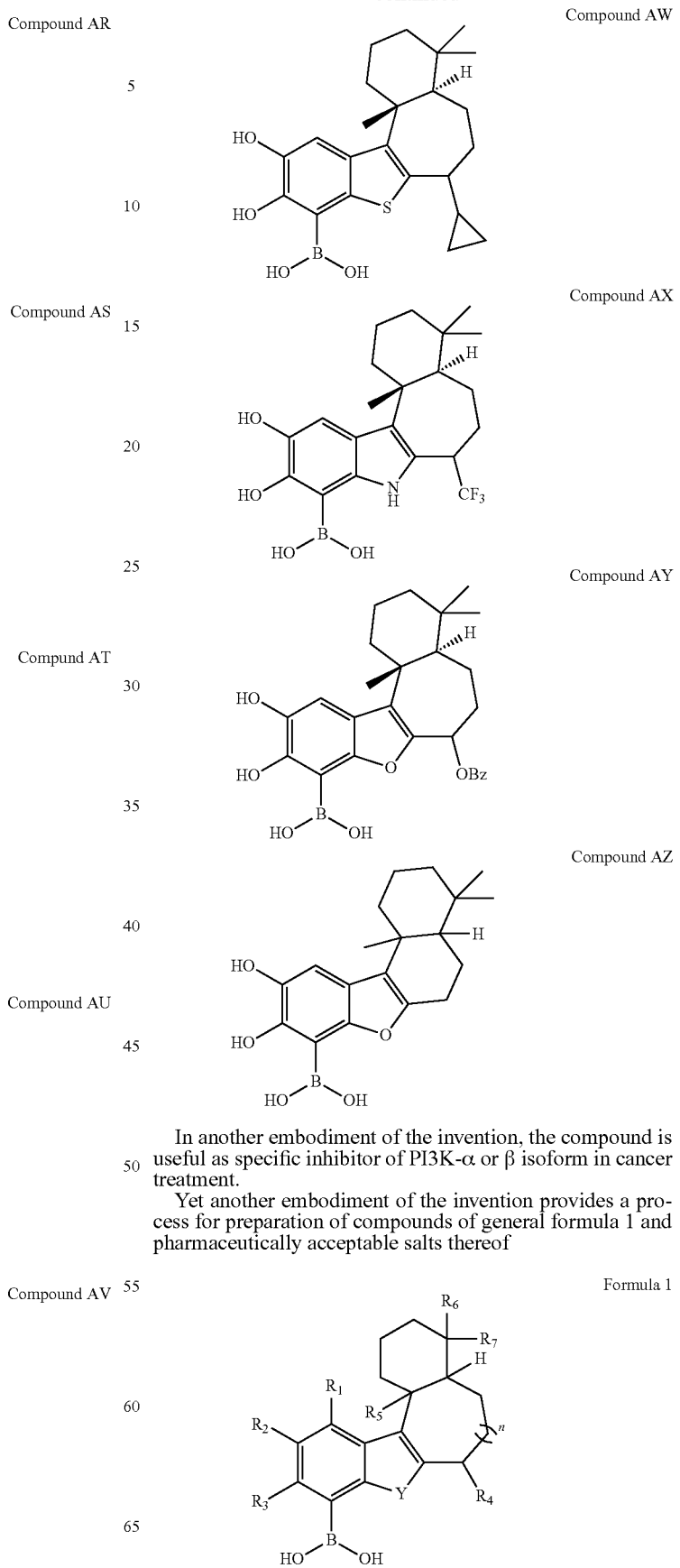

Compound AW

Compound AX

Compound AY

Compound AZ

In another embodiment of the invention, the compound is useful as specific inhibitor of PI3K-α or β isoform in cancer treatment.

Yet another embodiment of the invention provides a process for preparation of compounds of general formula 1 and pharmaceutically acceptable salts thereof Formula 1 wherein,
a) 'Y'=O, S, NH or NR, wherein R=alkyl moiety, aryl moiety, heteroaryl moiety cyclic aliphatic ring or aromatic system;
b) wherein n=0 or 1;
ci) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
wherein, R, R', R" are independently selected from a group consisting of alkyl moiety, aryl moiety, heteroaryl moiety and cyclic aliphatic ring,
wherein the cyclic aliphatic ring is selected from a group consisting of cyclopropyl, cyclobutyl, cyclopentyl and cyclohexyl ring and wherein the cyclic aliphatic ring has different substitutions at different positions,
wherein the alkyl moiety is selected from a group consisting of methyl, ethyl, propyl, isopropyl, butyl and isobutyl,
and wherein aryl or heteroaryl moiety has substitutions selected from a group consisting of halo, alkyl with different chain length, nitro, amino, and sulphonyl substitutions;
di) wherein $R_4$=H or OR or SR or $SO_2R$ or $OSO_3R$ or SiRR'R" or $NH_2$ or NHR or NRR' or an alkyl substituent or one to ten carbon chain either linear or branched, saturated or unsaturated alkyl group optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R,
wherein R, R', R" are independently selected from a group consisting of alkyl moiety, aryl moiety, heteroaryl moiety and cyclic aliphatic ring with different substitutions with varying chain length cyclic aliphatic ring with different substitutions and varying chain length,
wherein the alkyl moiety is selected from a group consisting of methyl, ethyl, propyl, isopropyl, butyl isobutyl,
and wherein aryl or heteroaryl moiety has substitutions selected from a group consisting of halo, alkyl with different chain length, nitro, amino, and sulphonyl substitutions;
wherein the alkyl substituent is selected from a group consisting of methyl, ethyl, propyl and higher homologues,
wherein the higher homologues are linear, branched or alicyclic substituents,
wherein the alicyclic substituents are selected from a group consisting of cyclopentane, cyclohexane, higher membered rings, fused rings and aryl/heteroaryl substituted alkyl groups,
wherein the aryl/heteroaryl substituted alkyl groups are benzylic or unsaturated alkyl groups further selected from a group consisting of cinnamul, crotyl and prenyl substituents;
e) wherein $R_5$, $R_6$ and $R_7$ are independently selected from a group consisting of H, one to ten carbon chain either linear or branched, saturated or unsaturated at any position, and alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R" and R,
wherein R, R', R" independently selected from a group consisting of alkyl moiety, aryl moiety, heteroaryl moiety and cyclic aliphatic ring with different substitutions.
wherein the process comprises the following steps:
i) reacting compound 9 with n-butyl lithium or potassium-tert-butoxide in an ether solvent in presence of a base;

Compound 9

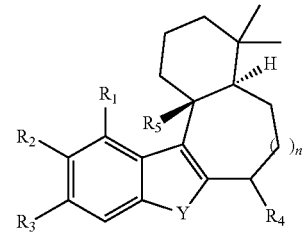

ii) adding triethyl or trimethyl borate to the above mixture obtained in step (i) and stirring;
iii) quenching the reaction of step (ii) with saturated ammonium chloride solution followed by extraction with water immiscible solvent to obtain compound of general formula 10

General formula 10

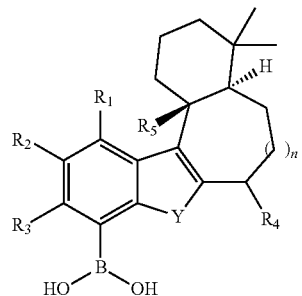

iv) reacting the compound 10 with $BI_3$ or DMS or $AlCl_3$/thiourea in a proportion in the range of 1:1 to 3:4 by moles in an ether solvent;
v) quenching the reaction of step (iv) by addition of hypo solution followed by extraction with a water immiscible solvent to obtain compound of general formula 1.

In yet another embodiment of the invention, the ether solvent used in step (i) and (v) is selected from a group consisting of tetrahydrofuran, dichloromethane, diethyl ether, diisopropyl ether and isopropyl ether.

In yet another embodiment of the invention, the base in step (i) is selected from a group consisting of tetramethyl ethylene diamine, triethyl amine, trimethyl amine and diisopropyl ethyl amine.

In yet another embodiment of the invention, reaction in step (i) is carried out at a temperature in the range of −78° C. to 35° C. for a period ranging between 5 to 10 min.

In yet another embodiment of the invention, reaction in step (ii) is carried out at a temperature in the range of 0-5° C., for a period ranging between 1 to 2 h.

In yet another embodiment of the invention, the water immiscible solvent in step (iii) and (v) is selected from a group consisting of ethylacetate, dichloromethane, ether or chloroform.

In still another embodiment of the invention, reaction in step (iv) is carried out at a temperature ranging between −78° C. to 35° C. for a period ranging between 1 to 3 h, In still another embodiment of the invention, the compound of general formula 1 obtained in step (v) is converted into a pharmaceutically acceptable salt.

In still another embodiment of the invention, the compound of general formula 1 is converted into a pharmaceutically acceptable salt by a process comprising the steps of mixing the compound of general formula 1 with a base in a ratio 1:1 proportion, wherein the base is selected from a group consisting of sodium hydroxide, potassium hydroxide and ammonium hydroxide in water, stirring the reaction mixture for 1-2 h followed by drying to obtain the pharmaceutically acceptable salt of the compound of general formula 1.

Yet another embodiment of the invention provides a pharmaceutical composition comprising an effective amount of the compound of formula 1, optionally along with a pharmaceutically acceptable carrier, salt, excipients or diluents.

In still another embodiment of the invention, the pharmaceutically acceptable carrier is selected from a group consisting of water, buffered saline, glycols, glycerols, olive oil and liposomes.

Still another embodiment of the invention provides a method of treatment of cancer by specific inhibition of PI3K-α or β isoform in a human cancer cell line using a compound of general formula 1,

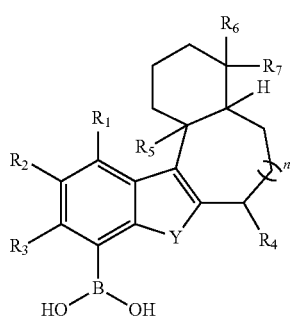

Formula 1 wherein,
a) 'Y'=O, S, NH or NR, wherein R=alkyl moiety, aryl moiety, heteroaryl moiety cyclic aliphatic ring or aromatic system;
b) wherein n=0 or 1;
cii) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
wherein, R, R', R" are independently selected from a group consisting of alkyl moiety, aryl moiety, heteroaryl moiety and cyclic aliphatic ring,
wherein the cyclic aliphatic ring is selected from a group consisting of cyclopropyl, cyclobutyl, cyclopentyl and cyclohexyl ring and wherein the cyclic aliphatic ring has different substitutions at different positions,
wherein the alkyl moiety is selected from a group consisting of methyl, ethyl, propyl, isopropyl, butyl and isobutyl,
and wherein aryl or heteroaryl moiety has substitutions selected from a group consisting of halo, alkyl with different chain length, nitro, amino, and sulphonyl substitutions;
dii) wherein $R_4$=H or OR or SR or $SO_2R$ or $OSO_3R$ or SiRR'R" or $NH_2$ or NHR or NRR' or an alkyl substituent or one to ten carbon chain either linear or branched, saturated or unsaturated alkyl group optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R, wherein R, R', R" are independently selected from a group consisting of alkyl moiety, aryl moiety, heteroaryl moiety and cyclic aliphatic ring with different substitutions with varying chain length cyclic aliphatic ring with different substitutions and varying chain length,
wherein the alkyl moiety is selected from a group consisting of methyl, ethyl, propyl, isopropyl, butyl isobutyl,
and wherein aryl or heteroaryl moiety has substitutions selected from a group consisting of halo, alkyl with different chain length, nitro, amino, and sulphonyl substitutions;
wherein the alkyl substituent is selected from a group consisting of methyl, ethyl, propyl and higher homologues,
wherein the higher homologues are linear, branched or alicyclic substituents,
wherein the alicyclic substituents are selected from a group consisting of cyclopentane, cyclohexane, higher membered rings, fused rings and aryl/heteroaryl substituted alkyl groups,
wherein the aryl/heteroaryl substituted alkyl groups are benzylic or unsaturated alkyl groups further selected from a group consisting of cinnamul, crotyl and prenyl substituents;
e) wherein $R_5$, $R_6$ and $R_7$ are independently selected from a group consisting of H, one to ten carbon chain either linear or branched, saturated or unsaturated at any position, and alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R" and R,
wherein R, R', R" independently selected from a group consisting of alkyl moiety, aryl moiety, heteroaryl moiety and cyclic aliphatic ring with different substitutions.
wherein the method comprises: mixing the compound of general formula 1 and a human cancer cell line selected from a group consisting of a lung cell line (A549), a leukemia cell line (THP1), a prostrate cell line (PC-3) and a colon cell line (caco-2, colo205, HCT-115), and specifically inhibiting PI3K-α or β isoform in the human cancer cell line.

In another embodiment of the invention, dosage of compound of general formula 1 is in the range of 20 mg/kg to 100 mg/kg.

In another embodiment of the invention, the representative compound A has a GI50 concentration in the range of 2.4 µM-2.6 µM when used for in vitro activity against colon and breast cancer cell lines.

In another embodiment of the invention, the representative compound A demonstrates >74% optimal growth inhibition in human cancer cell lines at a concentration of 10 µM.

In another embodiment of the invention, the representative compound E when used for in vitro activity against colon cancer cell lines increases sub-G1/G0 population and shows concentration dependent growth arrest in G1/G0 population and late apoptosis in colon cancer cell lines.

FIGURES AND TABLES

FIG. 1: In vitro cell line based anticancer activity of some representative boronic acid bearing liphagane compounds FIGS. 3, 4 and 5: Shows binding studies of the compound A, Compound E, Liphagal and compound AZ FIG. 1: Shows general structure of boronic acid bearing liphagane scaffold FIG. 2. Results of structural binding (in silico) studies of Compound A with catalytic domain of PI3K-α

Figure 3:
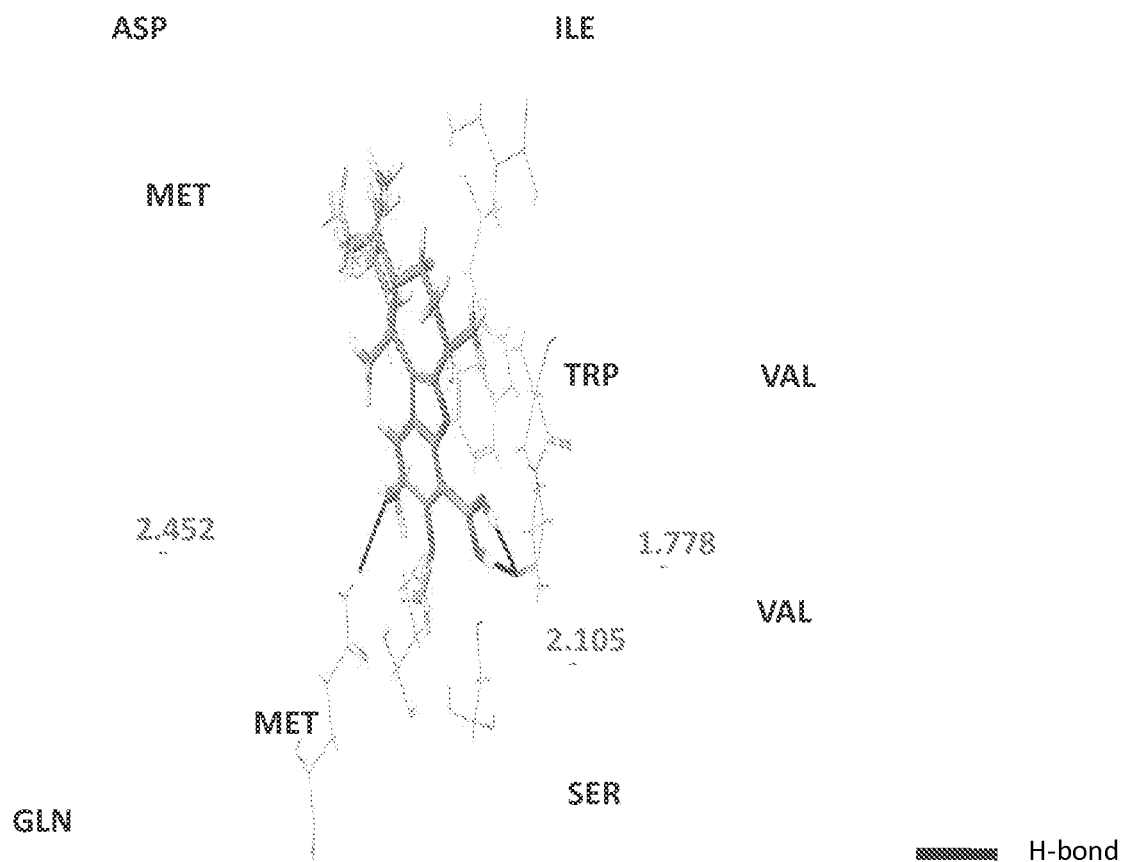

FIG. 3. Results of structural binding (in silico) studies of Compound E with catalytic domain of PI3K-a FIG. 6: Shows general scheme for the synthesis of boronic acid containing compound of general formula 1 (compound 11)

Figure 7:
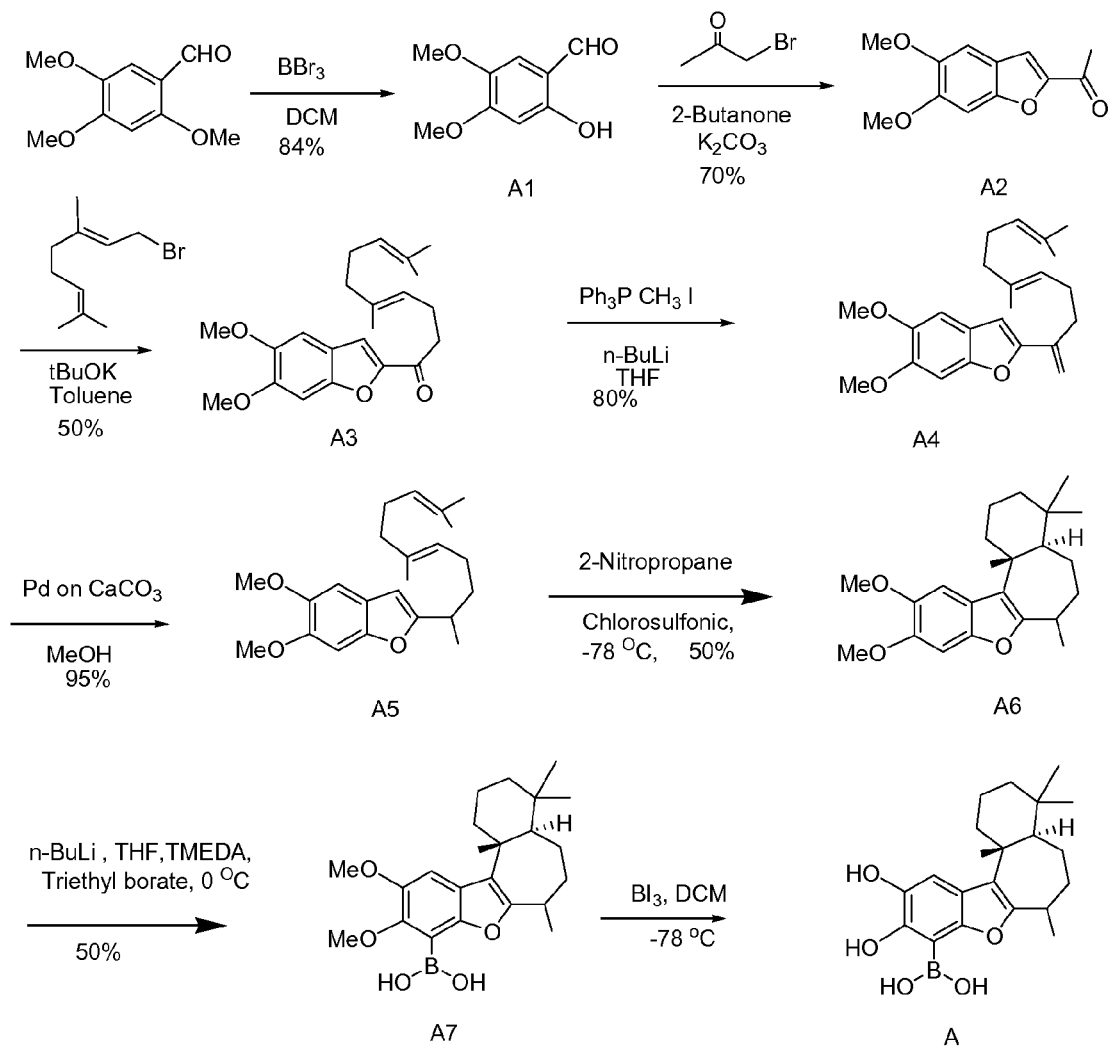

FIG. 7: Typical scheme for the synthesis of compound A

Figure 8:
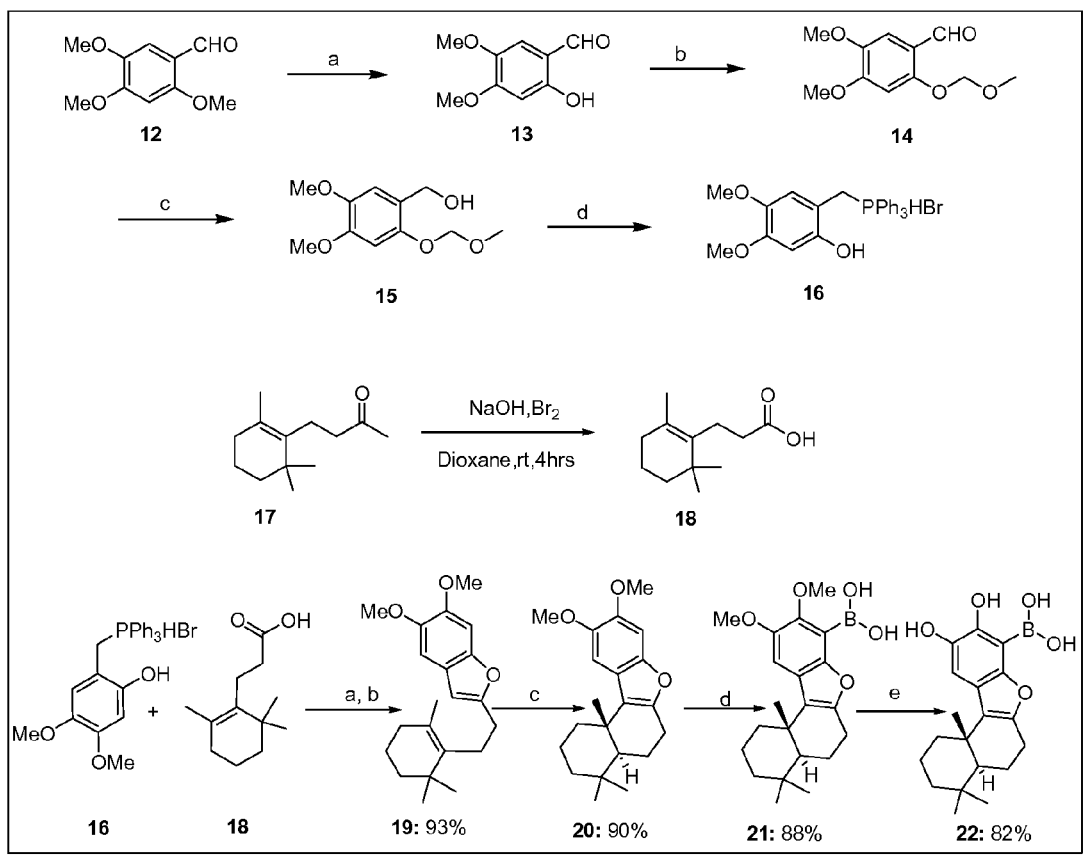

FIG. 8: Typical scheme for the synthesis of compound AZ

Figure 9:
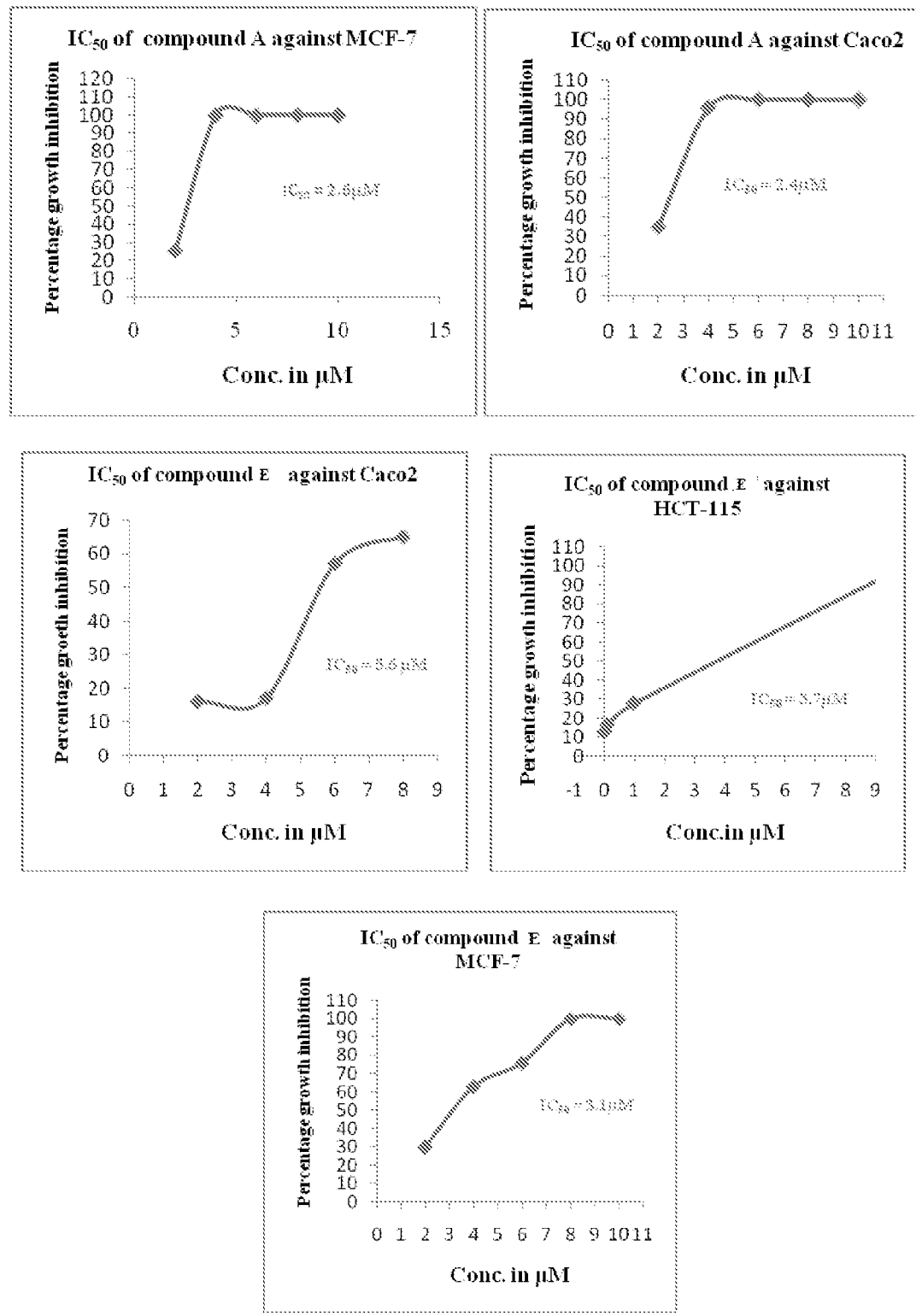

FIG. 9: $IC_{50}$ results of Compound A by MTT assay on caco-2 cell line

Figure 10:
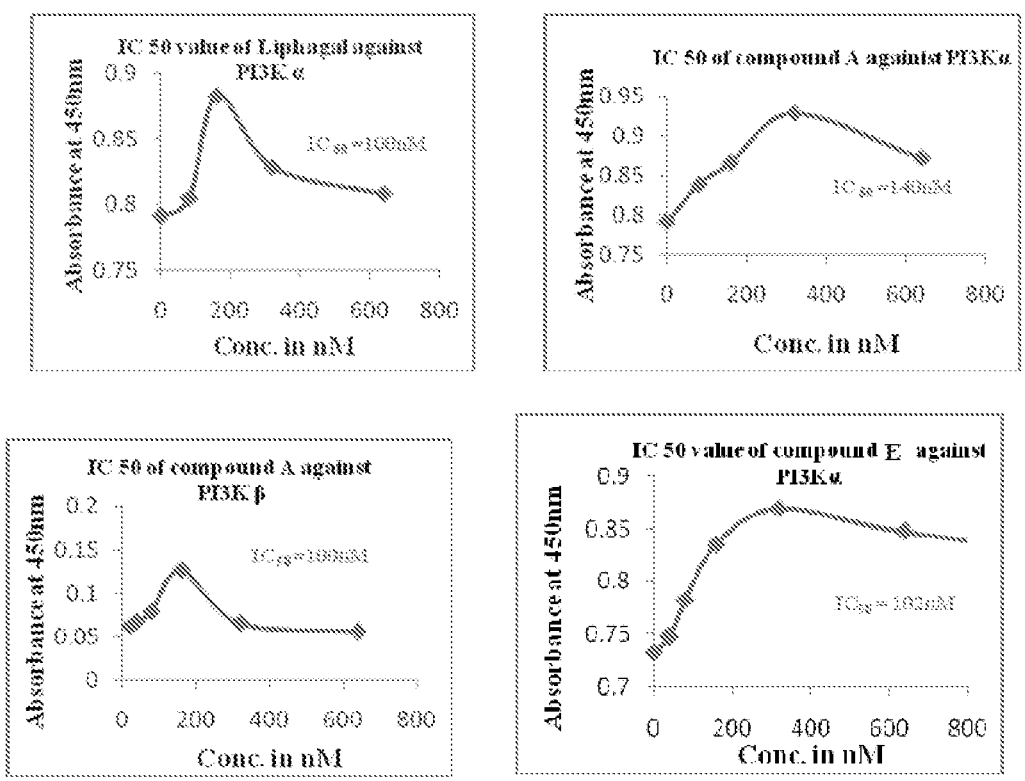

FIG. 10: $IC_{50}$ results of Compound A by enzyme based assay (PI3K-α and β)

Figure 11:
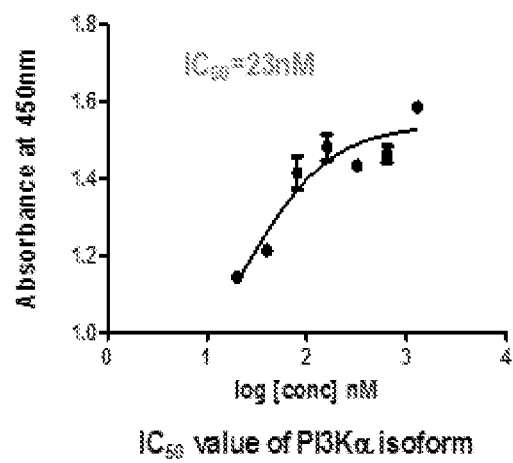
Figure 14:
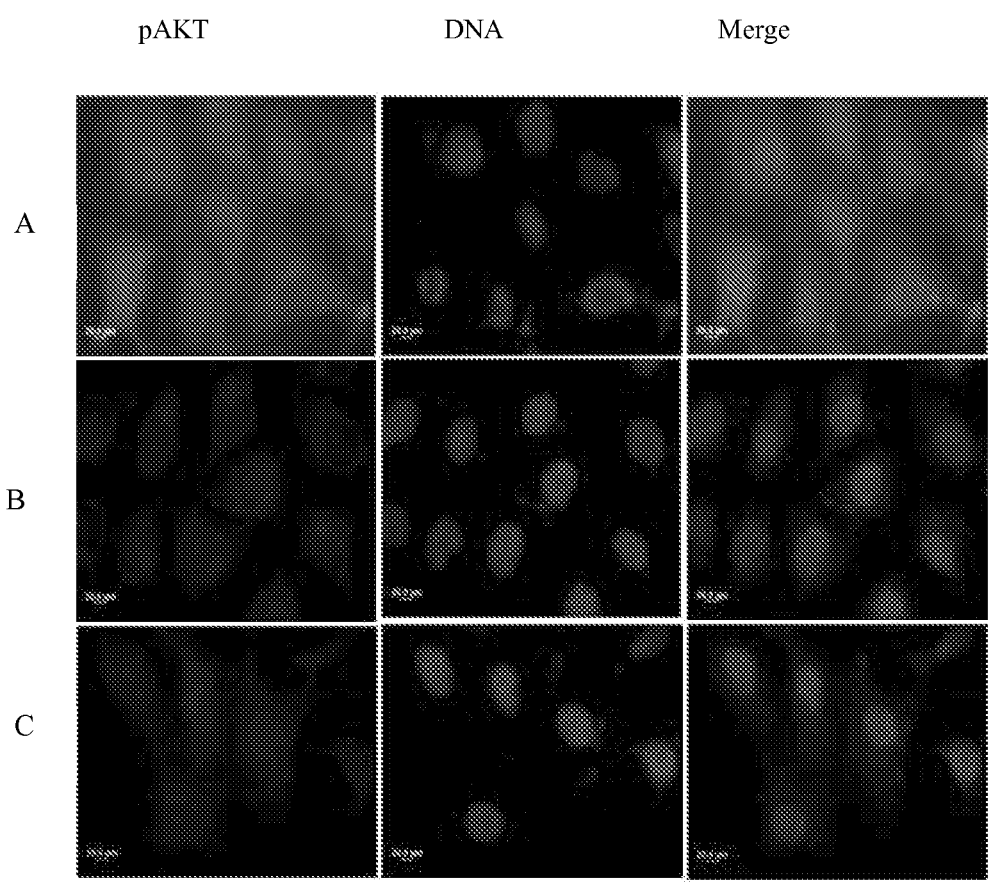

FIG. 11: $IC_{50}$ results of Compound A by enzyme based assay (PI3K-α and β). Graph showing $IC_{50}$ value of PI3K-α isoform for compound-AZ; Table 2: Showing $IC_{50}$ values of PI3K isoforms for compound AZ FIG. 12: Cell cycle analysis of compound A FIG. 13: Showing concentration dependent increase in apoptotic cell population for compound E FIG. 14: Immunofluorescent microscopic analysis of CACO-2 cells using Phospho-Akt (Ser473) rabbit polyclonal IgG (labeled with texas red). A—Untreated cells, B and C—Cells treated with liphagal and compound E, 4 and 3 μM respectively for 24 hr showing inhibition of pAKT. Nuclei were stained blue with DAPI

ABBREVIATIONS

ACN: acetonitrile
Ac: acetyl
$CDCl_3$: deuterated chloroform
$CHCl_3$: chloroform
$^{13}CNMR$: carbon nuclear magnetic resonance
DCM or $CH_2Cl_2$: dichloromethane
DIPEA: diisopropyl ethyl amine
DMF: dimethylformamide
DMSO: dimethylsulfoxide
EtOAc: ethylacetate
h or hr: hour
$^1HNMR$: proton nuclear magnetic resonance
$IC_{50}$: 50% inhibitory concentration
IR: infrared
J: coupling constant (Hz)
MeOH: methanol
MHz: Megahertz
mg: milli gram
μg: microgram
μL: micro liter
Mmol: milli mole
MTT: mitochondrial membrane potential
m/z: mass-to-charge ratio
PI3-K: phosphatidylinositol-3-kinase
TEA: triethyl amine
TFA: trifluoroacetic acid
THF: tetrahydrofuran
TLC: thin layer chromatography
TMA: trimethyl amine
TMEDA: tetramethyl ethylene diamine

DETAILED DESCRIPTION OF THE INVENTION

In an embodiment of the present invention the Formula 1 represents different compounds of meroterpenoid based liphagane scaffold having boronic acid functionality at 6th position of phenyl ring, wherein, R1 to R3 are independently selected from H, OH, OR, COR, CHO, $CO_2R$, OCOR, $NH_2$, NHR, NRR', $NO_2$, F, Cl, Br, I, $OSO_3H$, $SO_2R$, CN, SiRR'R", $OCF_3$, $CF_3$ and R. Wherein, R, R', R" may be alkyl, aryl, heteroaryl or any cyclic aliphatic ring with different substitutions.

In yet another embodiment, 'Y' is O, S, NH, and NR, wherein, R-may be substituted with alkyl, aryl, heteroaryl moiety or any cyclic aliphatic or aromatic system.

In an embodiment of the present invention, n and n1 are selected carbon chain length from 0, 1 and 2.

In an another embodiment, wherein, $R_4$ is H or OR or SR or $SO_2R$ or $OSO_3R$ or SiRR'R" or $NH_2$ or NHR or NRR' or a one to ten carbon chain either linear or branched, saturated or unsaturated alkyl group optionally substituted with OH, H, OH, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" and R. Wherein, R, R', R" are alkyl, aryl, heteroaryl or cyclic aliphatic ring having substitutions with varying chain length.

In an embodiment, wherein, the substituent $R_4$ is also selected from a group consisting of hydrogen, alkyl substituents viz., methyl, ethyl, propyl and the higher homologues either linear of branched, including alicyclic such as cyclopentane, cyclohexane or higher membered rings, fused rings, aryl/heteroaryl substituted alkyl groups including benzlic or its higher homologues that might include unsaturated alkyl groups such as cinnamul, crotyl and prenyl substituents.

In yet another embodiment of the present invention, wherein, $R_5$, $R_6$ and $R_7$ are H or one to ten carbon chain either linear or branched, saturated or unsaturated at any position, alkyl group optionally substituted with OH, H, OH, =O, =S, OR, COR, CHO, $CO_2R$, OCOR, $NH_2$, NHR', NR', NR'R", $NO_2$, F, Cl, Br, I, $OSO_3H$, $SO_2R$, CN, SiRR'R" and R. Here R, R', R" may be alkyl, aryl, heteroaryl or any cyclic aliphatic ring with different substitutions.

In embodiment of the present invention, R is independently selected from H or one to ten carbon chain either linear or branched, saturated or unsaturated, alkyl group optionally substituted with OH, H, OH, =O, =S, OR, COR, CHO, $CO_2R$, OCOR, $NH_2$, NHR, NRR', $NO_2$, F, Cl, Br, I, $OSO_3H$, $SO_2R$, CN, SiRR'R" and R. Here R, R', R" may be alkyl, aryl, heteroaryl or any cyclic aliphatic ring with different substitutions.

Wherein, further the substituent R at various positions is also selected from a group consisting of hydrogen, alkyl substituents viz., methyl, ethyl, propyl and the higher homologues either linear or branched, including alicyclic such as cyclopentane, cyclohexane or higher membered rings, fused ringsm aryl/heteroaryl substituted alkyl groups including benzlic or its higher homologues that might include unsaturated alkyl groups such as cinnamul, crotyl and prenyl substituents.

In an embodiment in the present invention, the routine method was used for the in silico bioinformatics study of liphagal and its boronic acid based compounds, it is as mentioned below: all the computational studies were carried out in the Schrodinger suite 2010 molecular modeling software. The 2D structures of all the molecules were built in the maestro window. All the molecules were then converted to their respective 3D structure, with various conformers, tautomers and ionization states using the Ligprep and Confgen modules. The molecules were then minimized using the OPLS_2005 force field. The 3D crystal structure of PI3Kα reported in Protein Data Bank (PDB) was used as receptor for docking studies (PDB ID: 3HHM). The protein was downloaded from the PDB and was prepared for docking using the Protein Preparation wizard. Hydrogen's were added to the protein and the missing loops were built. Bond length and bond order correction was also carried out for preparing the protein for docking studies. The active site grid was generated based on the already co-crystallised ligand of the receptor using receptor grid generation module. The ligands were docked on to the receptor through this grid using Glide module and flexible docking was carried out for all the conformers in order to find out the binding mode of these ligands. The extra precision (XP) scoring function of Glide was used for carrying out these studies. In yet another embodiment of the present invention, wherein, the results obtained in the in silico studies of liphagal and its boronic acids based compounds are as: based on the docking studies, it was found that the boronic acid analogues of liphagal bind with better affinity to PI3Kα than liphagal. The interaction studies show that boronic acid (OH) are involved in strong H-bond interactions with Val851 and Gln859, whereas liphagal is involved in H-bond interaction at one place only with Gln859. Also the dock score of boronic acid based compound was about −10 and that of liphagal was about −8.5, which shows a stronger affinity of boronic acid analogues towards PI3Kα.

EXAMPLES

The invention is further described by reference to following examples which are intended to illustrate and should not be construed to limit the scope of the present invention.
Materials and Method:
Chemistry:
General: Solvents were purified according to the standard procedures, and reagents used were of highest purity available. All reactions were performed in flame-dried glass apparatus under argon/nitrogen atmosphere unless mentioned otherwise. Anhydrous solvents like $CH_2Cl_2$, $Et_2O$, THF, $CH_3OH$, $CH_3CN$, DMF, pyridine, $Et_3N$ were freshly dried using standard methods. NMR measurements ($^1H$ and $^{13}C$) were recorded on either 400 or 500 MHz spectrometer (Bruker) fitted with pulse-field gradient probe, and trimethylsilane (TMS) or residual resonance of deuterated solvent were used as internal reference. Chemical shifts are expressed in (δ) parts per million and coupling constants J in hertz. Mass spectra were recorded on ESI MS or MALDI-TOF/TOF MS/MS-MS spectrophotometer using 2,5-Dihydroxy benzoic acid/α-Cyano-4-hydroxy benzoic acid/Sinapinic acid (Sigma-Aldrich) as matrix in acetonitrile:water containing 0.01% TFA. Optical rotations were measured on a digital PerkinElmer-241 polarimeter. Analytical TLC was performed on Merck 60 $F_{254}$ plates, and compounds were visualized by spraying and charring with phosphomolybdic acid or 20% $H_2SO_4$ in MeOH as developing reagent. Preparative TLC was performed on pre-coated silica gel 60 $F_{254}$ plates (20×20 cm) purchased from Merck. Silica column chromatography was carried out with silica gel (100-200 mesh) or flash silica gel (230-400 mesh) purchased from Merck.

Example 1

Synthesis of Compound A

For steps 1 to 6 (Ref: Mehta, G; Likhite, N. S.; Ananda Kumar, C. S. Tet. Lett. 2009, 50, 5260.) The steps involved for the synthesis of compound A are described as below—

Step 1: Synthesis of 2-hydroxy, 4,5-dimethoxybenzaldehyde (A1)

To solution of 3,4,5-trimethoxybenzaldehyde (5 g, 25.5 mmol) in $CH_2Cl_2$ (125 ml) at 0° C. was added $BBr_3$ (6.39 g, 25.5 mmol). The resulting dark mixture was stirred at 0° C. for 10 hrs after completion of the reaction checked by TLC $H_2O$ (100 mL) was then added and the mixture was stirred for 10 min and the aqueous phase was extracted by $CH_2Cl_2$. The organic phase was dried over $Na_2SO_4$, and evaporated under reduced pressure. The resulting residue was purified by silica gel ($CH_2Cl_2$) afforded the 2-hydroxy 4,5dimethoxybenzaldehyde A1 (4.3 g) in 87% yield isolated yellow solid: $^1H$ NMR (500 MHz, $CDCl_3$) δ 11.33 (s, 1H), 9.63 (s, 1H), 6.83 (s, 1H), 6.40 (s, 1H), 3.87 (s, 3H), 3.81 (s, 3H) ppm. Mass: ESI [M+Na]$^+$: 225.06; Elemental anal. calcd. for $C_9H_{10}O_4$; C, 59.34; H, 5.53; O, 35.13. found C, 59.14; H, 5.13; O, 34.90.

Step 2: Synthesis of 1-(5,6 dimethoxy benzofuran-2-yl)ethanone (A2)

To a solution of 2-hydroxy 4,5-dimethoxybenzaldehyde (2 g, 10.98 mmol) in butane-2-one (15 ml) added $K_2CO_3$ (6.07 g, 43.95 mmol) and then stirred at 0° C. for 10 min added bromoacetone (2.24 g, 16.47 mmol) and refluxed at 90° C. for 4 hr. After completion of the reaction butane-2-one was distilled off and water was added and extracted by ethylacetate twice. The EtOAc phase was dried over $Na_2SO_4$, Chromatography of the residue on silica gel (3:7 EtOAc/hexane) afforded the ketone A2 (1.69 g) in 70% yield pale yellow solid: $^1H$ NMR (500 MHz, $CDCl_3$) δ 7.29 (s, 1H), 7.04 (s, 1H), 6.98 (s, 1H), 3.94 (s, 3H), 3.90 (s, 3H), 2.30 (s, 3H) ppm. Mass: ESI [M+Na]$^+$: 243.07; Elemental anal. calcd. for $C_{12}H_{12}O_4$; C, 65.45; H, 5.49. found C, 65.20; H, 5.25.

Step 3: Synthesis of 1-(5,6-dimethoxybenzofuran-2-yl)-5,9-dimethyldeca-4,8-dien-1-one (A3)

To a solution of 1-(5,6 dimethoxy benzofuran-2-yl)ethanone A2 (1 g, 4.545 mmol) in anhydrous Toluene added tBuOK (0.51 g, 4.545 mmol) at 0° C. under argon atmosphere and then stirred at the same temperature for 15 min to this reaction mixture geranyl bromide added drop wise. Resulting suspension stirred at the same temperature for 2 hrs. 50 ml water was added to the reaction mixture and layers were separated. Aqueous layer was extracted with ethylaectate. The combined organic extract were washed with brine and dried over $Na_2SO_4$, evaporated under reduced pressure. Chromatography of the residue on silica gel (5% EtOAc/hexanes) afforded the ketone A3 (1.69 g) in 70% yield pale yellow liquid: $^1H$ NMR (500 MHz, $CDCl_3$) δ 7.425 (s, 1H), 7.365 (s, 1H), 7.06 (s, 1H), 5.12-5.16 (m, 1H), 5.08-5.04 (m, 1H), 3.96 (s, 3H), 3.93 (s, 3H), 2.97-2.89 (t, 2H), 2.50-2.40 (m, 2H), 2.17-2.00 (m, 4H), 1.66 (s, 3H), 1.63 (s, 3H), 1.64 (s, 3H), 1.58 (s, 3H), ppm. Mass: ESI [M+Na]$^+$: 379.2; Elemental anal. calcd. for $C_{22}H_{28}O_4$; C, 74.13; H, 7.92. found C, 74.0; H, 5.25.

Step 4: Synthesis of 5,6-dimethoxy-2-((E)-6,10-dimethylundeca-1,5,9-trien-2-yl)benzofuran (A4)

Triphenylphos-phenemethyl iodide (wittig salt, 2.247 g 5.6 mmol) has taken in a dry RBF kept in ice-salt mixture to this added dry THF (6 mL) to the resulting mixture nBuLi (2.5 mol in hexane 3.370, 8.4 mmol), was added drop wise until reaction mixture converted to yellow suspension. To the reaction mixture a solution of ketone (1 g, 2.8 mmol) in THF was added drop wise. Resulting suspension was stirred for 2 hrs. After completion of the reaction 10% ammonium chloride solution 30 ml was added and extracted by EtOAc. Chromatography of the residue on silica gel (3% EtOAc/Hexanes) afforded the compound A4 (0.79 g) in 80% yield colorless liquid: $^1H$ NMR (500 MHz, $CDCl_3$) δ 6.95 (s, 1H), 6.63 (s, 1H), 5.86 (s, 1H), 5.31-5.30 (d, 1H), 5.20-5.18 (d, 2H), 5.11-5.08 (t, 1H), 3.90 (s, 3H), 3.90 (s, 3H), 2.46-2.43 (t, 2H), 2.32-2.28 (q, 2H), 2.08-2.04 (q, 2H), 2.01-1.98 (t, 2H), 1.68 (s, 3H), 1.59 (s, 3H), 1.56 (s, 3H), ppm. Mass: ESI [M+Na]$^+$:

377.22; Elemental anal. calcd. for $C_{23}H_{30}O_3$; C, 77.93; H, 8.53. found C, 77.55; H, 8.35.

Step 5: Synthesis of 5,6-dimethoxy-2-((E)-1,6,10-trimethylundeca-5,9-dien-2-yl)benzofuran (A5)

To a solution of compound A4 (0.7 g 1.9 mmol) in MeOH was added 10 Mol % Pd/C and reaction was shacked at 40 psi pressure for 0.5 hrs. After completion of the reaction (monitored by TLC) filtered the reaction mixture and evaporated the methanol completely. Chromatography of the residue on silica gel (3% EtOAc/Hexanes) afforded the compound A5 (0.633 g) in 90% yield colorless liquid: $^1$H NMR (500 MHz, $CDCl_3$) δ 7.04 (s, 1H), 6.98 (s, 1H), 6.294 (s, 1H), 5.15-5.12 (m, 4H), 3.940 (s, 6H), 2.94-2.91 (m, 1H), 2.10-1.98 (m, 4H), 1.87-1.82 (m, 2H), 1.74 (s, 3H), 1.634 (s, 3H), 1.59 (s, 3H), 1.34-1.32 (d, 3H), ppm. Mass: ESI [M+Na]$^+$: 356.24; Elemental anal. calcd. for $C_{23}H_{32}O_3$; C, 77.49; H, 9.05. found C, 77.49; H, 9.05.

Step 6: Synthesis of Compounds (A6)

To a solution of the benzofuran A5 (0.6 g, 1.6 mmol) in 2-nitropropane (25 mL), at −85° C. was added chlorosulfonic acid (0.977 g, 8.42 mmol). The resulting mixture was allowed to stir at −78° C. for 30 min. An aqueous solution of $NaHCO_3$ was then added and the aqueous phase was extracted with EtOAc. The EtOAc phase was dried over $Na_2SO_4$, filtered and evaporated under reduced pressure. Chromatography of the residue on silica gel (3% EtOAc/Hexanes) afforded the compounds A6 (0.3 g) in 50% yield colorless liquid with racemic mixture $^1$H NMR ($CDCl_3$, 500 MHz) δ 7.13 (s, 1H), 6.85 (s, 1H), 3.89 (s, 3H), 3.88 (s, 3H), 2.56 (br d, J=14.1 Hz, 1H), 2.15 (m, 1H), 1.82 (m, 1H), 1.71 (qt, J=13.7, 3.5 Hz, 1H), 1.69 (m, 1H), 1.64-1.41 (m, 8H), 1.40 (d, J=7.2 Hz, 3H), 1.36 (s, 3H), 1.25 (ddd, J=13.3, 13.3, 3.5 Hz, 1H), 0.99 (s, 3H), 0.95 (s, 3H). Mass: ESI [M+Na]$^+$: 356.24; Elemental anal. calcd. for $C_{23}H_{32}O_3$; C, 77.49; H, 9.05. found C, 77.49; H, 9.05.

Step 7: Synthesis of Compound (A7)

For the purpose of this application, compound A7 has been interchangeably referred to as compound E.

To a solution of benzofuran A6 (0.1 g, 0.281 mmol) in THF (1.5 mL) at 0° C. was added nBuLi (2.5 M in hexane). After stirring at this temperature for 20 min triethylborate was added. The mixture was stirred at rt for 1 hr. Aqueous $NH_4Cl$ was added and the aqueous phase was extracted with EtOAc dried over $Na_2SO_4$, and evaporated under reduced pressure. Chromatography of the residue on silica gel (8% EtOAc/Hexanes) afforded the compounds A7 (0.05 g) in 50% white solid racemic mixture $^1$H NMR (500 MHz, $CDCl_3$) δ 6.83 (s, 1H), 3.94 (s, 3H), 3.92 (s, 3H), 2.56-2.49 (m, 1H), 1.56-1.52 (m, 4H), 1.48 (s, 3H), 1.37 (s, 3H), 0.99 (s, 3H), 0.96 (d, 3H) ppm. Mass: ESI [M+Na]$^+$: 400.24; Elemental anal. calcd. for $C_{23}H_{33}BO_5$; C, 69.01; H, 8.31; B, 2.70. found C, 69.10; H, 8.20; B, 2.50.

Step 8: Synthesis of Compound A

The solution of $BI_3$ in DCM was added slowly and drop wise in the round bottom flask containing solution of compound A7 in DCM at −78° C. The mixture of this was stirred at same temperature for half an hour the slowly raised to rt. The progress of reaction was monitored by TLC. The reaction mixture was neutralized using potassium thiosulphate solution and extracted with DCM solution and separated the organic layer, dried over sodium sulphate, concentrated in vaccuo. The crude was purified by column chromatography using hexane/EtOAc as eluent. $^1$H NMR (500 MHz, $CDCl_3$) δ 6.83 (s, 1H), 2.56-2.49 (m, 1H), 1.56-1.52 (m, 4H), 1.48 (s, 3H), 1.37 (s, 3H), 0.99 (s, 3H), 0.96 (d, 3H) ppm. Mass: ESI [M+Na]$^+$: 372.211; Elemental anal. calcd. for $C_{21}H_{29}BO_5$; C, 67.75; H, 7.85; B, 2.90. found C, 67.65; H, 7.61; B, 2.30.

All the compounds disclosed in formula 1, are prepared by employing the similar method containing different substitutions at R1, R2, R3 and R4 positions, as described for the preparation of compound A. The details of reaction conditions are depicted in the table given below—

| Compound code | | Reactions | | | | |
|---|---|---|---|---|---|---|
| | | Step 1 | Step 2 | Step 3 | Step 4 | Step 5 |
| Compound A | Starting material | 2,4,5-Trimethoxy benzaldehyde | 2-hydroxy-4,5-dimethoxybenzaldehyde | 1-(5,6-dimethoxy benzofuran-2-yl)ethanone | (E)-1-(5,6-dimethoxy benzofuran-2-yl)-5,9-dimethyldeca-4,8-dien-1-one | 5,6-dimethoxy-2-((E)-6,10-dimethylundeca-1,5,9-trien-2-yl)benzofuran |
| | Solvent | Dchloro methane | Butane2-one | Toluene | THF | MeOH |
| | Temperature | RT | Reflux for 4 hrs | 0° C. | 0° C. | RT |
| | Yield | 84% | 70% | 50% | 80% | 95% |
| Compound B | Starting material | 2-methoxy-4,5-bis(trifluoromethoxy)benzaldehyde | 2-hydroxy-4,5-bis(trifluoromethoxy)benzaldehyde | 1-(5,6-bis(trifluoromethoxy)benzofuran-2-yl)ethanone | (E)-1-(5,6-bis(trifluoromethoxy)benzofuran-2-yl)-5,9-dimethyldeca-4,8-dien-1-one | 5,6-bis(trifluoromethoxy)benzofuran-2-((E)-6,10-dimethylundeca-1,5,9-trien-2-yl)benzofuran |
| | Solvent | DCM | Toluene | Toluene | THF | MeOH |
| | Temperature | 0° C. | Reflux for 4 hrs | 0° C. | 0° C. | RT |
| | Yield | 85% | 85% | 60% | 80% | 95% |
| Compound C | Starting material | 4,5-bis(trifluoromethyl)-2-methoxybenzaldehyde | 2-hydroxybenzaldehyde | 1-(5,6-bis(trifluoromethyl)benzofuran-2-yl)ethanone | (E)-1-(5,6-bis(trifluoromethyl)benzofuran-2-yl)-5,9-dimethyldeca-4,8-dien-1-one | 5,6-bis(trifluoromethyl)-2-((E)-6,10-dimethylundeca-1,5,9-trien-2-yl)benzofuran |
| | Solvent | DCM | Toluene | Toluene | THF | MeOH |
| | Temperature | 0° C. | Reflux for 4 hrs | 0° C. | 0° C. | RT |
| | Yield | 85% | 85% | 60% | 80% | 95% |
| Compound D | Starting material | 2-methoxy-4,5-dimethylbenzaldehyde | 2-hydroxy-4,5-dimethylbenzaldehyde | 1-(5,6-dimethylbenzofuran-2-yl)ethanone | | |
| | Solvent | DCM | Toluene | Toluene | THF | MeOH |
| | Temperature | 0° C. | Reflux for 4 hrs | 0° C. | 0° C. | RT |
| | Yield | 85% | 85% | 60% | 80% | 95% |

| | | -continued | | |
|---|---|---|---|---|
| Compound E | Starting material | 2,4,5-Trimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran |
| | Solvent | Dchloromethane | Toluene | THF | MeOH |
| | Temperature | RT | 0° C. | 0° C. | RT |
| | Yield | 84% | 50% | 80% | 95% |
| Compound F | Starting material | 2-hydroxy-4,5-dimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran |
| | Solvent | Dchloromethane | Toluene | THF | MeOH |
| | Temperature | RT | 0° C. | 0° C. | RT |
| | Yield | 84% | 50% | 80% | 95% |
| Compound G | Starting material | 6-methoxybenzo[d][1,3]dioxole-5-carbaldehyde | 1-(benzofuro[6,5-d][1,3]dioxol-6-yl)ethanone | (E)-1-(benzofuro[6,5-d][1,3]dioxol-6-yl)-5,9-dimethyldeca-4,8-dien-1-one | 6-((E)-6,10-dimethylundeca-1,5,9-trien-2-yl)-5H-[1,3]dioxolo[4,5-f]benzofuran (estimated) |
| | Solvent | Dchloromethane | Toluene | THF | MeOH |
| | Temperature | RT | 0° C. | 0° C. | RT |
| | Yield | 84% | 50% | 80% | 95% |
| Compound H | Starting material | 4-amino-2-methoxy-5-morpholinobenzaldehyde | 1-(6-amino-5-morpholinobenzofuran-2-yl)ethanone | (E)-1-(6-amino-5-morpholinobenzofuran-2-yl)-5,9-dimethyldeca-4,8-dien-1-one | 2-((E)-6,10-dimethylundeca-1,5,9-trien-2-yl)-5-morpholinobenzofuran-6-amine |
| | Solvent | Dchloromethane | Toluene | THF | MeOH |
| | Temperature | RT | 0° C. | 0° C. | RT |
| | Yield | 84% | 50% | 80% | 95% |

| | | Compound I | Compound J | Compound K | Compound L |
|---|---|---|---|---|---|
| Starting material | | 4,5-diamino-2-methoxybenzaldehyde | 4,5-diamino-2-hydroxybenzaldehyde | 2-methoxy-4,5-bis(methylamino)benzaldehyde | 6-methoxy-1H-benzo[d]imidazole-5-carbaldehyde |
| | | 1-(5,6-diaminobenzofuran-2-yl)ethanone | 1-(5,6-diaminobenzofuran-2-yl)ethanone | 1-(5,6-bis(methylamino)benzofuran-2-yl)ethanone | 1-(3H-benzofuro[6,5-d]imidazole-6-yl)ethanone |
| | | (E)-1-(5,6-diaminobenzofuran-2-yl)-5,9-dimethyldeca-4,8-dien-1-one | (E)-1-(5,6-diaminobenzofuran-2-yl)-5,9-dimethyldeca-4,8-dien-1-one | (E)-1-(5,6-bis(methylamino)benzofuran-2-yl)-5,9-dimethyldeca-4,8-dien-1-one | (E)-1-(3H-benzofuro[6,5-d]imidazole-6-yl)-5,9-dimethyldeca-4,8-dien-1-one |
| | | 2-((E)-6,10-dimethylundeca-1,5,9-trien-2-yl)benzofuran-5,6-diamine | 2-((E)-6,10-dimethylundeca-1,5,9-trien-2-yl)benzofuran-5,6-diamine | N5,N6-dimethyl-2-((E)-6,10-dimethylundeca-1,5,9-trien-2-yl)benzofuran-5,6-diamine | 6-((E)-6,10-dimethylundeca-1,5,9-trien-2-yl)-3H-benzofuro[6,5-d]imidazole |
| Solvent | | Dichloromethane | Dichloromethane | Dichloromethane | Dichloromethane |
| | | Toluene | Toluene | Toluene | Toluene |
| | | THF | THF | THF | THF |
| | | MeOH | MeOH | MeOH | MeOH |
| Temperature | | RT | RT | RT | |
| | | Reflux for 4 hrs | Reflux for 4 hrs | Reflux for 4 hrs | |
| | | 0° C. | 0° C. | 0° C. | |
| Yield | | 84% | 84% | 84% | |
| | | 70% | 70% | 70% | |
| | | 80% | 80% | 80% | |
| | | 95% | 95% | 95% | |

-continued

|  |  |  |  |  |  |
|---|---|---|---|---|---|
| | Temperature | RT | Reflux for 4 hrs | 0° C. | 0° C. | 95% |
| Compound M | Yield | 84% | 70% | 50% | 80% | |
| | Starting material | 4,5-diamino-2-methoxybenzaldehyde | 4,5-diamino-2-hydroxybenzaldehyde | 1-(5,6-diaminobenzofuran-2-yl)ethanone | (E)-1-(5,6-diaminobenzofuran-2-yl)-5,9-dimethyldeca-4,8-dien-1-one | 2-((E)-6,10-dimethylundeca-1,5,9-trien-2-yl)benzofuran-5,6-diamine |
| | Solvent | Dchloro methane | Butane2-one | Toluene | THF | MeOH |
| | Temperature | RT | Reflux for 4 hrs | 0° C. | 0° C. | RT |
| Compound N | Yield | 84% | 70% | 50% | 80% | 95% |
| | Starting material | 2-hydroxy-4,5-dimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran | 5,6-dimethoxy-2-((E)-6,10-dimethylundeca-1,5,9-trien-2-yl)benzofuran-2-nitropropane |
| | Solvent | Butane2-one | Toluene | THF | MeOH | |
| | Temperature | Reflux for 4 hrs | 0° C. | 0° C. | RT | −78° C. |
| Compound O | Yield | 70% | 50% | 80% | 95% | 50% |
| | Starting material | 2-hydroxy-4,5-dimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran | 5,6-bis(allyloxy)-2-((E)-6,10-dimethylundeca-1,5,9-trien-2-yl)benzofuran-2-nitropropane |
| | Solvent | Dchloro methane | Butane2-one | Toluene | THF | −78° C. |
| | Temperature | RT | Reflux for 4 hrs | 0° C. | 0° C. | |
| Compound P | Yield | 70% | 50% | 80% | 95% | 50% |
| | Starting material | 4,5-bis(allyloxy)-2-methoxybenzaldehyde | 4,5-bis(allyloxy)-2-hydroxybenzaldehyde | 1-(5,6-bis(allyloxy)benzofuran-2-yl)ethanone | (E)-1-(5,6-bis(allyloxy)benzofuran-2-yl)-5,9-dimethyldeca-4,8-dien-1-one | 5,6-bis(allyloxy)-2-((E)-6,10-dimethylundeca-1,5,9-trien-2-yl)benzofuran |
| | Solvent | Dchloro methane | Butane2-one | Toluene | THF | MeOH |

-continued

| | | | | | | |
|---|---|---|---|---|---|---|
| | Temperature | RT | 0° C. | Reflux for 4 hrs | 0° C. | RT |
| Compound Q | Yield | 84% | 50% | 70% | 80% | 95% |
| | Starting material | 4-formyl-5-methoxybenzene-1,2-dinitro | 2-acetylbenzofuran-5,6-dicarbonitro | 4-formyl-5-hydroxybenzene-1,2-dinitro | 2-((E)-5,9-dimethyldeca-4,8-dienoyl)benzofuran-5,6-dicarbonitro | 2-((E)-6,10-dimethylundeca-1,5,9-trien-2-yl)benzofuran-5,6-dicarbonitro |
| | Solvent | Dchloro methane | Toluene | Butane2-one | THF | MeOH |
| | Temperature | RT | 0° C. | Reflux for 4 hrs | 0° C. | RT |
| Compound R | Yield | 84% | 50% | 70% | 80% | 95% |
| | Starting material | 4-formyl-5-methoxybenzene-1,2-dinitrile | 2-acetylbenzofuran-5,6-dicarbonitrile | 4-formyl-5-hydroxybenzene-1,2-dinitrile | 2-((E)-5,9-dimethyldeca-4,8-dienoyl)benzofuran-5,6-dicarbonitrile | 2-((E)-6,10-dimethylundeca-1,5,9-trien-2-yl)benzofuran-5,6-dicarbonitrile |
| | Solvent | Dchloro methane | Toluene | Butane2-one | THF | MeOH |
| | Temperature | RT | 0° C. | Reflux for 4 hrs | 0° C. | RT |
| Compound S | Yield | 84% | 50% | 70% | 80% | 95% |
| | Starting material | 4,5-difluoro-2-methoxybenzaldehyde | 1-(5,6-dicfluorobenzofuran-2-yl)ethanone | 4,5-difluoro-2-hydroxybenzaldehyde | (E)-1-(5,6-difluorobenzofuran-2-yl)-5,9-dimethyldeca-4,8-dien-1-one | 5,6-difluoro-2-((E)-6,10-dimethylundeca-1,5,9-trien-2-yl)benzofuran |
| | Solvent | Dchloro methane | Toluene | Butane2-one | THF | MeOH |
| | Temperature | RT | 0° C. | Reflux for 4 hrs | 0° C. | RT |
| Compound T | Yield | 84% | 50% | 70% | 80% | 95% |
| | Starting material | 4,5-dichloro-2-methoxybenzaldehyde | 1-(5,6-dichlorobenzofuran-2-yl)ethanone | 4,5-dichloro-2-hydroxybenzaldehyde | (E)-1-(5,6-dichlorobenzofuran-2-yl)-5,9-dimethyldeca-4,8-dien-1-one | 5,6-dichloro-2-((E)-6,10-dimethylundeca-1,5,9-trien-2-yl)benzofuran |
| | Solvent | Dchloro methane | Toluene | Butane2-one | THF | MeOH |

|  |  | -continued | | |
|---|---|---|---|---|
| Compound U | Starting material | 2-amino-4,5-dimethoxybenzaldehyde | 1-(5,6-dimethoxy-1H-indol-2-yl)ethanone | (E)-1-(5,6-dimethoxy-1H-indol-2-yl)-5,9-dimethyldeca-4,8-dien-1-one | 5,6-dimethoxy-2-((E)-6,10-dimethylundeca-1,5,9-trien-2-yl)benzo[b]thiophene 2-nitropropane |
|  | Solvent | Butane-2-one | Toluene | THF | MeOH |
|  | Temperature | Reflux for 4 hrs | 0° C. | 0° C. | −78° C. |
|  | Yield | 70% | 50% | 80% | 50% |
| Compound V | Starting material | 2-mercapto-4,5-dimethoxybenzaldehyde | 1-(5,6-dimethoxybenzo[b]thiophen-2-yl)ethanone | (E)-1-(5,6-dimethoxybenzo[b]thiophen-2-yl)-5,9-dimethyldeca-4,8-dien-1-one | 5,6-dimethoxy-2-((E)-6,10-dimethylundeca-1,5,9-trien-2-yl)benzo[b]thiophene 2-nitropropane |
|  | Solvent | Butane-2-one | Toluene | THF | MeOH |
|  | Temperature | Reflux for 4 hrs | 0° C. | 0° C. | −78° C. |
|  | Yield | 70% | 50% | 80% | 50% |
| Compound W | Starting material | 2-hydroxy-4,5-dimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran MeOH |
|  | Solvent | Butane-2-one | Toluene | THF | RT |
|  | Temperature | Reflux for 4 hrs | 0° C. | 0° C. | 95% |
|  | Yield | 70% | 50% | 80% | |
| Compound X | Starting material | 2-amino-4,5-dimethoxybenzaldehyde | 1-(5,6-dimethoxy-1-methyl-1H-indol-2-yl)ethanone | (E)-1-(5,6-dimethoxy-1-methyl-1H-indol-2-yl)-5,9-dimethyldeca-4,8-dien-1-one | (E)-6,10-dimethyl-2-((E)-6,10-dimethylundeca-1,5,9-trien-2-yl)-1H-indole |
|  | Solvent | THF | Toluene | THF | MeOH |
|  | Temperature | rt | 0° C. | 0° C. | RT |
|  | Yield | 60% | 50% | 80% | 95% |

-continued

| | | | | | |
|---|---|---|---|---|---|
| Compound Y | Starting material | 2-amino-4,5-dimethoxybenzaldehyde | 1-(5,6-dimethoxy-1-methyl-1H-indol-2-yl)ethanone | (E)-1-(5,6-dimethoxy-1-methyl-1H-indol-2-yl)-5,9-dimethyldeca-4,8-dien-1-one | 5,6-dimethoxy-1-methyl-2-((E)-6,10-dimethylundeca-1,5,9-trien-2-yl)-1H-indole |
| | Solvent | Butane2-one | THF | THF | MeOH |
| | Temperature | Reflux for 4 hrs | rt | 0° C. | RT |
| | Yield | 70% | 60% | 80% | 95% |
| Compound Z | Starting material | 2,4,5-Trimethoxybenzaldehyde | 2-hydroxy-4,5-dimethoxybenzaldehyde | (E)-1-(5,6-dimethoxybenzofuran-2-yl)-5,9-dimethyldeca-4,8-dien-1-one | 5,6-dimethoxy-2-((E)-2,7,11-trimethyldodeca-2,6,10-trien-3-yl)benzofuran |
| | Solvent | Dchloro methane | Butane2-one | THF | MeOH |
| | Temperature | RT | Reflux for 4 hrs | 0° C. | RT |
| | Yield | 84% | 70% | 80% | 95% |
| Compound AA | Starting material | 2-methoxy, 4,5-Diacetoxy benzaldehyde | 2-hydroxy-4,5-acetoxybenzaldehyde | (E)-1-(5,6-diaceoxybenzofuran-2-yl)-5,9-dimethyldeca-4,8-dien-1-one | 5,6-diacetoxy-2-((E)-6,10-dimethylundeca-1,5,9-trien-2-yl)-1H-indole |
| | Solvent | Dchloro methane | Butane2-one | THF | MeOH |
| | Temperature | RT | Reflux for 4 hrs | 0° C. | RT |
| | Yield | 84% | 70% | 80% | 95% |
| Compound AB | Starting material | 2-amino,4,5-diacetyl amino benzaldehyde | 1-(5,6-diAcetylamino-1H-indol-2-yl)ethanone | (E)-1-(5,6-diacetylamino-1H-indol-2-yl)-5,9-dimethyldeca-4,8-dien-1-one | 5,6-diacetylamine 2-((E)-6,10-dimethylundeca-5,9-dien-2-yl)-1H-indole-5,6-diacetamine |
| | Solvent | Toluene | Toluene | THF | MeOH |
| | Temperature | 0° C. | 0° C. | 0° C. | 2-nitropropane −78° C. |
| | Yield | 50% | 50% | 50% | 60% |

-continued

| Compound | | Starting material | | | |
|---|---|---|---|---|---|
| Compound AC | Starting material | 4,5-bis(dimethylamino)-2-methoxybenzaldehyde | 4,5-bis(dimethylamino)-2-hydroxybenzaldehyde | 1-(5,6-bis(dimethylamino)benzofuran-2-yl)ethanone | (E)-1-(5,6-bis(dimethylamino)benzofuran-2-yl)-5,9-dimethyldeca-4,8-dien-1-one | N5,N5,N6,N6-tetramethyl-2-((E)-6,10-dimethylundeca-1,5,9-trien-2-yl)benzofuran-5,6-diamine |
| | Solvent | Dchloro methane | Butane2-one | Toluene | THF | MeOH |
| | Temperature | RT | Reflux for 4 hrs | 0° C. | 0° C. | RT |
| | Yield | 84% | 70% | | 80% | 95% |
| Compound AD | Starting material | 2-hydroxy-4,5-dimethoxybenzaldehyde | 1-(5,6-dimethoxybenzofuran-2-yl)ethanone | 50% (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of liphagal |
| | Solvent | Butane2-one | Toluene | THF | 2-nitropropane | THF |
| | Temperature | Reflux for 4 hrs | 0° C. | rt | −78° C. | 0-5° C. |
| | Yield | 70% | 85% | | 50% | 50% |
| Compound AE | Starting material | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of liphagal | Tetracyclic intermediate of liphagal with keto group at 10th posotion |
| | Solvent | Toluene | THF | 2-nitropropane | Doxane | MeOH |
| | Temperature | 0° C. | rt | −78° C. | 80° C. | rt |
| | Yield | 50% | 85% | 50% | 60% | 90% |
| Compound AF | Starting material | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic boronic acid intermediate of desmetyl liphagal | |
| | Solvent | Toluene | THF | 2-nitropropane | THF | Dioxane |

-continued

| Compound | | | | | | |
|---|---|---|---|---|---|---|
| Compound AG | Temperature | 0° C. | rt | −78° C. | 0° C. to rt | reflux |
| | Yield | 50% | 85% | 50% | 80% | 60% |
| | Starting material | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of liphagal | Tetracyclic intermediate of liphagal boronic acid | Tetracyclic intermediate of liphagal boronic acid with ktone at 10th position |
| | Solvent | THF | 2-nitropropane | THF | Dioxane | DCM |
| Compound AH | Temperature | 0-5° C. | rt | −78° C. | 80° C. | −78° C. to rt |
| | Yield | 50% | 85% | 50% | 60% | 50% |
| | Starting material | 1-(5,6-dimethoxybenzofuran-2-yl)ethanone | 5,6-dimethoxy-2-((E)-5,9-dimethyldeca-4,8-dienyl)benzofuran | Tetracyclic intermediate of liphagal | Tetracyclic boronic acid intermediate of desmetyl liphagal | |
| | Solvent | Toluene | 2-nitropropane | THF | Dioxane | |
| Compound AI | Temperature | 0° C. | rt | −78° C. | 0° C. to rt | reflux |
| | Yield | 50% | 85% | 50% | 80% | 60% |
| | Starting material | 1-(5,6-dimethoxybenzofuran-2-yl)ethanone | Tetracyclic intermediate of liphagal | Tetracyclic boronic acid intermediate of liphagal | Tetracyclic intermediate of liphagal boronic acid with ktone at 10th position | 5,6-Dihydroxy Tetracyclic intermediate of liphagal boronic acid with ktone at 10th position |
| | Solvent | Toluene | | THF | THF | |
| Compound AJ | Temperature | 0° C. | | | | |
| | Yield | 50% | | | | |
| | Starting material | 5,6-dimethoxy-2-((E)-5,9-dimethyldeca-4,8-dienyl)benzofuran | | | | |

-continued

|  |  |  |  |  |  |
|---|---|---|---|---|---|
| Compound AK | Solvent | 2-nitropropane | THF | Doxane | DCM | MeOH |
|  | Temperature | −78° C. | 0-5° C. | 80° C. | −78° C. to rt | rt |
|  | Yield | 50% | 50% | 60% | 50% | 90% |
|  | Starting material | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of Desmethyl liphagal | Tetracyclic derivative of liphagal with Keto group at 10$^{th}$ position | Tetracyclic derivative of liphagal with Hydroxy group at 10$^{th}$ position |
| Compound AL | Solvent | THF | 2-nitropropane | Doxane | MeOH | THF |
|  | Temperature | rt | −78° C. | reflux | rt |  |
|  | Yield | 85% | 50% | 60% | 90% | 50% |
|  | Starting material | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic derivative of liphagal with Keto group at 10$^{th}$ position | Tetracyclic derivative of liphagal with Hydroxy group at 10$^{th}$ position |
| Compound AM | Solvent | THF | 2-nitropropane | Doxane | MeOH | THF |
|  | Temperature | rt | −78° C. | reflux | rt |  |
|  | Yield | 85% | 50% | 60% | 90% | 50% |
|  | Starting material | 1-(5,6-dimethoxybenzofuran-2-yl)ethanone | 5,6-dimethoxy-2-((E)-5,9-dimethyldeca-4,8-dienyl)benzofuran |  | Tetracyclic intermediate of liphagal |  |
| Compound AN | Solvent | Toluene | THF | 2-nitropropane | Doxane | MeOH |
|  | Temperature | 0° C. | rt | −78° C. | 80° C. | rt |
|  | Yield | 50% | 85% | 50% | 60% | 90% |
|  | Starting material | 1-(5,6-dimethoxybenzofuran-2-yl)ethanone | 5,6-dimethoxy-2-((E)-5,9-dimethyldeca-4,8-dienyl)benzofuran |  | Tetracyclic intermediate of Desmethyl liphagal | Tetracyclic derivative of liphagal with Hydroxy group at 10$^{th}$ posotion |

-continued

| Compound | | Step 1 | Step 2 | Step 3 | Step 4 | Step 5 |
|---|---|---|---|---|---|---|
| Compound AO | Solvent | THF | 2-nitropropane | Doxane | MeOH | THF |
| | Temperature | rt | −78° C. | reflux | rt | rt |
| | Yield | 85% | 50% | 60% | 90% | 50% |
| | Starting material | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of Desmethyl liphagal | Tetracyclic derivative of liphagal with Keto group at $10^{th}$ position | Tetracyclic derivative of liphagal with Hydroxy group at $10^{th}$ position |
| Compound AP | Solvent | THF | 2-nitropropane | Doxane | MeOH | THF |
| | Temperature | rt | −78° C. | reflux | rt | rt |
| | Yield | 85% | 50% | 60% | 90% | 50% |
| | Starting material | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of Desmethyl liphagal | Tetracyclic derivative of liphagal with Keto group at $10^{th}$ position | Tetracyclic derivative of liphagal with Hydroxy group at $10^{th}$ position |
| Compound AQ | Solvent | THF | 2-nitropropane | Doxane | MeOH | |
| | Temperature | rt | −78° C. | reflux | rt | |
| | Yield | 85% | 50% | 60% | 90% | |
| | Starting material | 1-(5,6-dimethoxybenzofuran-2-yl)ethanone | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran | |
| Compound AR | Solvent | Butane-2-one | Toluene | THF | MeOH | |
| | Temperature | Reflux for 4 hrs | 0° C. | 0° C. | RT | |
| | Yield | 70% | 50% | 80% | 95% | |
| | Starting material | 2-hydroxy-4,5-dimethoxybenzaldehyde | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-5,9-dimethyldeca-4,8-dienyl)benzofuran | Tetracyclic intermediate of liphagal |
| | | | | | | Tetracyclic boronic acid intermediate of desmetyl liphagal |

-continued

| | | Compound AS | | | Compound AT | | | Compound AU | | |
|---|---|---|---|---|---|---|---|---|---|---|
| Solvent | Toluene | THF | 2-nitropropane | THF | Toluene | THF | 2-nitropropane | THF | Toluene | THF | Dioxane |
| Temperature | 0° C. | rt | −78° C. | 0° C. to rt | 0° C. | RT | −78° C. | 0-5° C. | 0° C. | 0° C. to rt | reflux |
| Yield | 50% | 85% | 50% | 80% | 50% | 95% | 50% | 50% | 50% | 80% | 60% |
| Starting material | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran | Tetracyclic Dimethoxy liphagal intermediate | 1-(5,6-dimethoxybenzofuran-2-yl)ethanone | (E)-1-(5,6-dimethoxybenzofuran-2-yl)-5,9-dimethyldeca-4,8-dien-1-one | 5,6-dimethoxy-2-((E)-6,10-dimethylundeca-1,5,9-trien-2-yl)benzofuran | Tetracyclic Dimethoxy liphagal intermediate | 1-(5,6-dimethoxybenzofuran-2-yl)ethanone | (E)-2-((E)-5,9-dimethyldeca-4,8-dienyl)benzofuran | Tetracyclic boronic acid intermediate of desmetyl liphagal |

-continued

| Compound | | | |
|---|---|---|---|
| Compound AV | Starting material | 1-(5,6-dimethoxy-1H-indol-2-yl)ethanone | (E)-1-(5,6-dimethoxy-1H-indol-2-yl)-5,9-dimethyldeca-4,8-dien-1-one | Tetracyclic intermediate of 5,6-dimethoxy indole Derivative of Liphagal with keto group at 10th position |
| | Solvent | Toluene | THF | Dioxane | MeOH |
| | Temperature | 0° C. | −78° C. | reflux | rt |
| | Yield | 50% | 50% | 60% | 90% |
| Compound AW | Starting material | 1-(5,6-dimethoxybenzo[b]thiophen-2-yl)ethanone | (E)-1-(5,6-dimethoxybenzo[b]thiophen-2-yl)-5,9-dimethyldeca-4,8-dien-1-one | Tetracyclic intermediate 5,6-dimethoxybenzo[b]thiophen derivative of liphagal |
| | Solvent | Toluene | THF | Dioxane | MeOH |
| | Temperature | 0° C. | −78° C. | reflux | rt |
| | Yield | 50% | 50% | 60% | 90% |
| Compound AX | Starting material | 1-(5,6-dimethoxy-1H-indol-2-yl)ethanone | (E)-1-(5,6-dimethoxy-1H-indol-2-yl)-5,9-dimethyldeca-4,8-dien-1-one | Tetracyclic intermediate of 5,6-dimethoxy indole Derivative of Liphagal with keto group at 10th position |
| | Solvent | Toluene | THF | Dioxane | MeOH |
| | Temperature | 0° C. | −78° C. | reflux | rt |
| | Yield | 50% | 50% | 60% | 90% |
| Compound AY | Starting material | 1-(5,6-dimethoxybenzofuran-2-yl)ethanone | (E)-1-(5,6-dimethoxybenzofuran-2-yl)-5,9-dimethyldeca-4,8-dien-1-one | Tetracyclic intermediate of liphagal with keto group at 10th posotion |

-continued

| | | | | | |
|---|---|---|---|---|---|
| | Solvent | THF | 2-nitropropane | Doxane | MeOH |
| | Temperature | rt | −78° C. | 80° C. | rt |
| | Yield | 85% | 50% | 60% | 90% |
| Compound AZ | Starting material | 4,5-dimethoxy-2-(methoxymethoxy)benzaldehyde | (4,5-dimethoxy-2-(methoxymethoxy)phenyl)methanol | 4,5-dimethoxy-2-methoxymethylbenzylphonium salt | Tricyclic sixmembered derivative of liphagal |
| | Solvent | Toluene | THF | DCM | DCM/THF | 2-nitropropane |
| | Temperature | 0° C. | rt | | Rt to reflux | −78° C. |
| | Yield | 50% | 85% | | 93% | 90% |
| | Starting material | 2,4,5-trimethoxybenzaldehyde | | | | |
| | Solvent | DCM | MeOH | ACN | | |
| | Temperature | 0° C. | rt | reflux | | |
| | Yield | 87% | 98% | 98% | | |

| Compound code | | Reactions | | |
|---|---|---|---|---|
| | | Step 6 | Step 7 | Step 8 |
| Compound A | Starting material | 5,6-dimethoxy-2-((E)-6,10-dimethylundeca-5,9-dien-2-yl)benzofuran | Tetracyclic Dimethoxy liphagal intermediate | Dimethoxy Liphagal boronic acid intermediate |
| | Solvent | 2-nitropropane | THF | DCM |
| | Temperature | −78° C. | 0-5° C. | −78° C. to rt |
| | Yield | 50% | 50% | 40% |
| Compound B | Starting material | 5,6-bis(trifluoromethoxy)-2-((E)-6,10-dimethylundeca-5,9-dien-2-yl)benzofuran | Tetracyclic bis(trifluoromethoxy) liphagal intermediate | |
| | Solvent | 2-nitropropane | THF | |
| | Temperature | −78° C. | 0-5° C. | |
| | Yield | 50% | 50% | |
| Compound C | Starting material | 5,6-bis(trifluoromethyl)-2-((E)-6,10-dimethylundeca-5,9-dien-2-yl)benzofuran | Tetracyclic bis(trifluoromethoxy) liphagal intermediate | |
| | Solvent | 2-nitropropane | THF | |
| | Temperature | −78° C. | 0-5° C. | |
| | Yield | 50% | 55% | |

-continued

| | | | |
|---|---|---|---|
| Compound D | Starting material | 5,6-dimethyl-2-((E)-6,10-dimethylundeca-5,9-dien-2-yl)benzofuran | Tetracyclic dimethyl liphagal intermediate |
| | Solvent | THF | |
| | Temperature | −78° C. | 0-5° C. |
| | Yield | 50% | 50% |
| Compound E | Starting material | 5,6-dimethoxy-2-((E)-6,10-dimethylundeca-5,9-dien-2-yl)benzofuran | Tetracyclic 5,6-dimethoxy liphagal intermediate |
| | Solvent | THF | |
| | Temperature | −78° C. | 0-5° C. |
| | Yield | 50% | 70% |
| Compound F | Starting material | 5,6-dimethoxy-2-((E)-6,10-dimethylundeca-5,9-dien-2-yl)benzofuran | Tetracyclic 5,6-diethyl lipghal intermediate |
| | Solvent | THF | |
| | Temperature | −78° C. | 0-5° C. |
| | Yield | 50% | 58% |
| Compound G | Starting material | 6-((E)-6,10-dimethylundeca-5,9-dien-2-yl)benzofuro[6,5-d][1,3]dioxole | Tetracyclic benzofuro[6,5-d][1,3]dioxole liphagla intermediate |
| | Solvent | THF | |
| | Temperature | −78° C. | 0-5° C. |
| | Yield | 50% | 50% |

-continued

| | | |
|---|---|---|
| Compound H | Starting material | 2-((E)-6,10-dimethylundeca-5,9-dien-2-yl)-5-morpholinobenzofuran-6-amine |
| | Solvent | 2-nitropropane |
| | Temperature | −78° C. |
| | Yield | 50% |
| Compound I | Starting material | 2-((E)-6,10-dimethylundeca-5,9-dien-2-yl)benzofuran-5,6-diamine |
| | Solvent | 2-nitropropane |
| | Temperature | −78° C. |
| | Yield | 50% |
| Compound J | Starting material | 2-((E)-6,10-dimethylundeca-5,9-dien-2-yl)benzofuran-5,6-diamine | Tetracyclic 5,6-diamino Liphagal intermediate |
| | Solvent | 2-nitropropane | Aceticanhydride |
| | Temperature | −78° C. | rt |
| | Yield | 50% | 80% |
| Compound K | Starting material | N5,N6-dimethyl-2-((E)-6,10-dimethylundeca-5,9-dien-2-yl)benzofuran-5,6-diamine |
| | Solvent | 2-nitropropane |
| | Temperature | −78° C. |
| | Yield | 50% |

-continued

| | | | | |
|---|---|---|---|---|
| Compound L | Starting material | 6-((E)-6,10-dimethylundeca-5,9-dien-2-yl)-3H-benzofuro[6,5-d]imidazole | | |
| | Solvent | 2-nitropropane | | |
| | Temperature | −78° C. | | |
| | Yield | 50% | | |
| Compound M | Starting material | 2-((E)-6,10-dimethylundeca-5,9-dien-2-yl)benzofuran-5,6-diamine | Tetracyclic 5,6-Diamine derivative of Liphagal | Tetracyclic 5,6-diamine derivative of Liphagal boronic acid |
| | Solvent | 2-nitropropane | THF | THF |
| | Temperature | −78° C. | 0-5° C. | 0° C. |
| | Yield | 50% | 60% | 50% |
| Compound N | Starting material | Tetracyclic Dimethoxy liphagal intermediate | Dimethoxy Liphagal boronic acid intermediate | 5,6-Dihydroxy tetracyclic liphagal borinic acid |
| | Solvent | DCM | THF | 2-nitropropane |
| | Temperature | −78° C. to rt | 0-5° C. | 0° C. |
| | Yield | 40% | 50% | 55% |
| Compound O | Starting material | Tetracyclic Dimethoxy liphagal intermediate | Dimethoxy Liphagal boronic acid intermediate | 5,6-Dihydroxy tetracyclic liphagal borinic acid |
| | Solvent | DCM | THF | 2-nitropropane |
| | Temperature | −78° C. to rt | 0-5° C. | 0° C. |
| | Yield | 40% | 50% | 55% |
| Compound P | Starting material | 5,6-bis(allyloxy)-2-((E)-6,10-dimethylundeca-5,9-2-yl)benzofuran | Tetracyclic 5,6-bis(allyloxy) Liphagal intermediate | |

-continued

| | | |
|---|---|---|
| Compound Q | Solvent | THF |
| | Temperature | 0-5° C. |
| | Yield | 55% |
| | Starting material | 2-((E)-6,10-dimethylundeca-5,9-dien-2-yl)benzofuran-5,6-dicarbonitrile | Tetracyclic 5,6-Dinitro substituted Liphagal intermediate |
| | Solvent | 2-nitropropane |
| | Temperature | −78° C. |
| | Yield | 50% |
| Compound R | Solvent | THF |
| | Temperature | 0-5° C. |
| | Yield | 45% |
| | Starting material | 2-((E)-6,10-dimethylundeca-5,9-dien-2-yl)benzofuran-5,6-dicarbonitrile | Tetracyclic 5,6-Dinitro substituted Liphagal intermediate |
| | Solvent | 2-nitropropane |
| | Temperature | −78° C. |
| | Yield | 50% |
| Compound S | Solvent | THF |
| | Temperature | 0-5° C. |
| | Yield | 60% |
| | Starting material | 5,6-difluoro-2-((E)-6,10-dimethylundeca-5,9-dien-2-yl)benzofuran | Tetracyclic 5,6-difluoro intermediate |
| | Solvent | 2-nitropropane |
| | Temperature | −78° C. |
| | Yield | 50% |
| Compound T | Solvent | THF |
| | Temperature | 0-5° C. |
| | Yield | 50% |
| | Starting material | 5,6-dichloro-2-((E)-6,10-dimethylundeca-5,9-dien-2-yl)benzofuran | Tetracyclic 5,6-dichloro intermediate of Liphagal |
| | Solvent | 2-nitropropane |
| | Temperature | −78° C. |
| | Yield | 50% |

-continued

| | | |
|---|---|---|
| Compound U | Starting material | Tetracyclic 5,6-Dimethoxy substituted indole analogue of lihagal |
| | Solvent | THF |
| | Temperature | 0-5° C. |
| | Yield | 50% |
| Compound V | Starting material | Tetracyclic 5,6-Dimethoxy substituted indole analogue of lihagal |
| | Solvent | THF |
| | Temperature | 0-5° C. |
| | Yield | 50% |
| Compound W | Starting material | Tetracyclic Dimethoxy liphagal intermediate |
| | Solvent | nitromethane |
| | Temperature | 0-5° C. |
| | Yield | 50% |
| Compound X | Starting material | 5,6-dimethoxy-1-methyl-2-((E)-6,10-dimethylundeca-5,9-dien-2-yl)-1H-indole |
| | Solvent | 2-nitropropane |
| | Temperature | −78° C. |
| | Yield | 50% |
| | Starting material | Tetracyclic 5,6-Dimethoxy substituted indole analogue of lihagal Boronic acid |
| | Solvent | DCM |
| | Temperature | −78° C. to rt |
| | Yield | 40% |
| | Starting material | Tetracyclic 5,6-Dimethoxy substituted indole analogue of lihagal boronic acid |
| | Solvent | DCM |
| | Temperature | −78° C. to rt |
| | Yield | 40% |
| | Starting material | Tetracyclic Dimethoxy benzopyran intermediate of liphagal |
| | Solvent | THF |
| | Temperature | 0° C. to RT |
| | Yield | 60% |
| | Starting material | Tetracyclic 5,6-dimethoxy substituted N-methyl indole analogue of liaphagal |
| | Solvent | THF |
| | Temperature | 0-5° C. |
| | Yield | 56% |
| | Starting material | Tetracyclic Dimethoxy benzopyran intermediate of Liphagal boronic acid |
| | Solvent | DCM |
| | Temperature | −78° C. to RT |
| | Yield | 45% |
| | Starting material | Tetracyclic 5,6-dimethoxy substituted N-methyl indole analogue of liaphagal boronic acid |
| | Solvent | DCM |
| | Temperature | −78° C. to rt |
| | Yield | 45% |

-continued

| | | |
|---|---|---|
| Compound Y | Starting material | 5,6-dimethoxy-1-methyl-2-((E)-6,10-dimethylundeca-5,9-dien-2-yl)-1H-indole |
| | Solvent | 2-nitropropane |
| | Temperature | −78° C. |
| | Yield | 50% |
| Compound Z | Starting material | 5,6-dimethoxy-2-((E)-2,7,11-trimethyldodeca-6,10-dien-3-ylbenzofuran |
| | Solvent | 2-nitropropane |
| | Temperature | −78° C. |
| | Yield | 50% |
| Compound AA | Starting material | 5,6-diacetoxy-2-((E)-6,10-dimethylundeca-5,9-dien-2-ylbenzofuran |
| | Solvent | 2-nitropropane |
| | Temperature | −78° C. |
| | Yield | 50% |
| Compound AB | Starting material | Tetracyclic Diacetylamino indole derivative of liphagal |
| | Solvent | THF |
| | Temperature | 0-5° C. |
| | Yield | 40% |

| | | |
|---|---|---|
| | | Tetracyclic 5,6-dimethoxy substituted N-methyl indole analogue of liphagal THF 0-5° C. 60% |
| | | Tetracyclic Dimethoxy liphagal derivative THF 0-5° C. 50% |
| | | Tetracyclic Diacetoxy liphagal intermediate THF 0-5° C. 50% |
| | | Dimethoxy Liphagal boronic acid derivative DCM −78° C. to rt 50% |

| | | -continued | |
|---|---|---|---|
| Compound AC | Starting material | N5,N5,N6,N6-tetramethyl-2-((E)-6,10-dimethylundeca-5,9-dien-2-yl)benzofuran-5,6-diamine | N5,N5,N6,N6-tetramethyl-substituted derivative of liphagal |
| | Solvent | 2-nitropropane | THF |
| | Temperature | −78° C. | 0-5° C. |
| | Yield | 50% | 50% |
| Compound AD | Starting material | Tetracyclic intermediate of liphagal boronic acid | Tetracyclic intermediate of liphagal boronic acid with ktone at 10th position |
| | Solvent | Doxane | DCM |
| | Temperature | 80° C. | −78° C. to rt |
| | Yield | 60% | 50% |
| Compound AE | Starting material | Tetracyclic intermediate of Liphagal with hydroxy group at 10th position | 5,6-Hydroxy,Tetracyclic intermediate of liphagal with trifluoromethoxy group at 10th position |
| | | | 5,6-Hydroxy,Tetracyclic intermediate of liphagal boronic acid with trifluoromethoxy at 10th position |
| | Solvent | THF | THF | DCM |
| | Temperature | rt | 0° C. to rt | 0° C. |
| | Yield | 60% | 80% | 40% |

-continued

| | | | | |
|---|---|---|---|---|
| Compound AF | Starting material | Tetracyclic intermediate of Liphagal boronic acid intermediate with Keto group at 10$^{th}$ position | Tetracyclic intermediate of Liphagal boronic acid intermediate with Hydroxy group at 10$^{th}$ position | 5,6-Dihydroxy Tetracyclic intermediate of Liphagal boronic acid intermediate with Hydroxy group at 10$^{th}$ position |
| | Solvent | MeOH | DCM | DCM |
| | Temperature | rt | −78° C. to rt | rt |
| | Yield | 80% | 50% | 45% |
| Compound AG | Starting material | 5,6-Dihydroxy Tetracyclic intermediate of liphagal boronic acid with ktone at 10$^{th}$ position | 5,6-Dihydroxy Tetracyclic intermediate of liphagal boronic acid with hydroxy at 10$^{th}$ position | 5,6-Dihydroxy Tetracyclic intermediate of liphagal boronic acid with azide at 10$^{th}$ position |
| | Solvent | MeOH | DCM | MeOH |
| | Temperature | rt | rt | rt |
| | Yield | 90% | 80% | 80% |
| Compound AH | Starting material | Tetracyclic intermediate of 1 Liphagal boronic acid intermediate with Hydroxy group at 10$^{th}$ position | Tetracyclic intermediate of Liphagal boronic acid intermediate with Hydroxy group at 10$^{th}$ position | |
| | Solvent | MeOH | DCM | |
| | Temperature | rt | −78° C. to rt | |
| | Yield | 80% | 45%0% | |

-continued

| Compound AI | Starting material | Tetracyclic derivative of Liphagal boronic acid intermediate with Keto group at 10th position | Tetracyclic derivative of Liphagal boronic acid intermediate with Hydroxy group at 10th position | 5,6-Hydroxy,Tetracyclic intermediate of liphagal boronic acid with Hydroxy at 10th position |
| --- | --- | --- | --- | --- |
| | Solvent | MeOH | THF | Ac₂O |
| | Temperature | rt | 0° C. to rt | 0° C. |
| | Yield | 80% | 80% | 50% |
| Compound AJ | Starting material | 5,6-Dihydroxy Tetracyclic intermediate of liphagal boronic acid with hydroxy at 10th position | 5,6-Dihydroxy Tetracyclic intermediate of liphagal boronic acid with azide at 10th position | 5,6-Dihydroxy Tetracyclic intermediate of liphagal boronic acid with azide at 10th position |
| | Solvent | DCM | MeOH | Ac₂O |
| | Temperature | rt | rt | rt |
| | Yield | 80% | 80% | 50% |
| Compound AK | Starting material | Tetracyclic derivative of liphagal with Amine group at 10th position | Tetracyclic derivative of liphagal with N-methy amine group at 10th position | Tetracyclic derivative of liphagalboronic acid with N-methy amine group at 10th position |
| | Solvent | THF | THF | DCM |
| | Temperature | rt | 0° C. | −78° C. to rt |
| | Yield | 70% | | 50% |

-continued

| | | | | |
|---|---|---|---|---|
| Compound AL | Starting material | Tetracyclic derivative of liphagal with Amine group at 10th position | Tetracyclic derivative of liphagal with N-dimethy amine group at 10th position | Tetracyclic derivative of liphagalboronic acid with N-dimethy amine group at 10th position |
| | Solvent | THF | THF | DCM |
| | Temperature | rt | 0° C. | −78° C. to rt |
| | Yield | 70% | | 50% |
| Compound AM | Starting material | Tetracyclic intermediate of Liphagal with hydroxy group at 10th position | 5,6-Hydroxy,Tetracyclic intermediate of liphagal with venyloxy group at 10th position | 5,6-Hydroxy,Tetracyclic intermediate of liphagal boronic acid with venyloxy at 10th position |
| | Solvent | | THF | DCM |
| | Temperature | | 0° C. to rt | 0° C. |
| | Yield | | 80% | 40% |
| Compound AN | Starting material | Tetracyclic derivative of liphagal with piperidine substitution at 10th position | Tetracyclic derivative of liphagalboronic acid with N-dimethy piperidine substation at 10th position | |
| | Solvent | THF | DCM | |
| | Temperature | 0° C. | −78° C. to rt | |
| | Yield | 70% | 50% | |
| Compound AO | Starting material | Tetracyclic derivative of liphagal with Morpholine substitution at 10th position | Tetracyclic derivative of liphagalboronic acid with N-dimethy Morpholine substation at 10th position | |

-continued

| | | | | | |
|---|---|---|---|---|---|
| Compound AP | Solvent | THF | DCM | | |
| | Temperature | 0° C. | −78° C. to rt | | |
| | Yield | 70% | 50% | | |
| | Starting material | Tetracyclic derivative of liphagal with Amine group at 10th position | Tetracyclic derivative of liphagal with N-dimethyl amine group at 10th position | Tetracyclic derivative of liphagalboronic acid with N-diethyl amine group at 10th position | |
| Compound AQ | Solvent | THF | THF | DCM | |
| | Temperature | rt | 0° C. | −78° C. to rt | |
| | Yield | 70% | | 50% | |
| | Starting material | Tetracyclic Dimethoxy liphagal intermediate | Dimethoxy Liphagal boronic acid intermediate | 5,6Dihydroxy Liphagal boronic acid intermediate | |
| Compound AR | Solvent | THF | DCM | dioxane | |
| | Temperature | 0-5° C. | −78° C. to rt | reflux | |
| | Yield | 50% | 40% | 60% | |
| | Starting material | Tetracyclic intermediate of l Liphagal boronic acid intermediate with Keto group at 10th position | Tetracyclic intermediate of Liphagal boronic acid intermediate with Hydroxy group at 10th position | 5,6dihycroy Tetracyclic intermediate of Liphagal boronic acid intermediate with Hydroxy group at 10th position | |
| Compound AS | Solvent | MeOH | DCM | Nitro methane | |
| | Temperature | rt | −78° C. to rt | 0 to 5° C. | |
| | Yield | 80% | 45%0% | 45% | |
| | Starting material | Dimethoxy Liphagal boronic acid intermediate | 5,6Dihydroxy Liphagal boronic acid intermediate | 5,6Dihydroxy Liphagal boronic acid intermediate formyl group at 10th position | |

-continued

| | | | |
|---|---|---|---|
| Compound AT | Solvent | DCM | MeOH |
| | Temperature | −78° C. to rt | rt |
| | Yield | 40% | 60% |
| | Starting material | Dimethoxy Liphagal boronic acid intermediate | 5,6Dihydroxy Liphagal boronic acid intermediate with formyl group at 10th position |
| Compound AU | Solvent | DCM | dioxane | MeOH, NaBH₄ |
| | Temperature | −78° C. to rt | reflux | rt |
| | Yield | 40% | 60% | 60% |
| | Starting material | Tetracyclic intermediate of desmethyl Liphagal boronic acid intermediate with Keto group at 10th position | Tetracyclic intermediate of desmethyl Liphagal boronic acid intermediate | 5,6-Hydroxy,Tetracyclic intermediate of liphagal boronic acid with Hydroxy at 10th position |
| Compound AV | Solvent | MeOH | THF | Ac₂O |
| | Temperature | rt | 0° C. to rt | 0° C. |
| | Yield | 80% | 80% | 50% |
| | Starting material | Tetracyclic intermediate of 5,6-dimethoxy indole Derivative of Liphagal with Hydroxy group at 10th position | Tetracyclic intermediate of 5,6-dimethoxy indole Derivative of Liphagalboronic acid with cyclopropyl group at 10th position | Tetracyclic intermediate of 5,6-dimethoxy indole Derivative of Liphagalboronic acid with cyclopropyl group at 10th position |
| Compound AW | Solvent | DCM | THF | DCM |
| | Temperature | rt | 0° C. to rt | −78° C. to rt |
| | Yield | 65% | 55% | 45% |
| | Starting material | Tetracyclic 5,6-dimethoxybenzo[b]thiophen derivative of Liphagal | Tetracyclic 5,6-dimethoxybenzo[b]thiophen derivative of | Tetracyclic 5,6-dimethoxybenzo[b]thiophen derivative of |

-continued

| | Compound AX | Compound AY | Compound AZ |
|---|---|---|---|
| Starting material | Liphagal with Hydroxy group at 10th position | Tetracyclic intermediate of 5,6-dimethoxy indole Derivative of Liphagal with Hydroxy group at 10th position | Liphagal with isopropyl group at 10th position |
| Solvent | DCM | DCM | THF |
| Temperature | rt | rt | −78° C. to rt |
| Yield | 65% | 65% | 55% |
| Starting material | Tetracyclic intermediate of 5,6-dimethoxy indole Derivative of Liphagal with Hydroxy group at 10th position | 5,6-Hydroxy,Tetracyclic intermediate of liphagal with benzyl group at 10th position | Tetracyclic intermediate of 5,6-dimethoxy indole Derivative of Liphagal with trifluoromethyl group at 10th position |
| Solvent | DCM | THF | THF |
| Temperature | −78° C. to rt | 0° C. to rt | −78° C. to rt |
| Yield | 45% | 80% | 55% |
| Starting material | Liphagal Boronic acid with trifluoromethyl group at 10th position | Tetracyclic sixmembered derivative of Liphagal boronic acid | 5,6-Hydroxy,Tetracyclic intermediate of liphagal boronic acid with benzyl at 10th position |
| Solvent | DCM | DCM | DCM |
| Temperature | −78° C. to rt | rt | 0° C. |
| Yield | 45% | 85% | 40% |
| Solvent | | THF | |
| Temperature | | 0° C. | |
| Yield | | 92% | |

Compound B: ¹H NMR (500 MHz, CDCl₃) δ6.91 (s, 1H), 3.18 (m, 1H), 1.82 (t, 2H), 1.78 (t, 1H), 1.71 (q, 2H), 1.45 (m, 2H), 1.42 (t, 2H), 1.44 (s, 3H), 1.38 (q, 2H), 1.34 (d, 3H), 1.12 (s, 6H), ppm. Mass: ESI [M+Na]⁺: 531.186; Elemental anal. calcd for $C_{23}H_{27}BF_6O_7$; C, 54.35; H, 5.31; B, 2.10; F, 22.44. found C, 54.33; H, 5.34; B, 2.11; F, 22.41.

Compound C: ¹H NMR (500 MHz, CDCl₃) δ7.60 (s, 1H), 3.18 (m, 1H), 1.82 (t, 2H), 1.78 (t, 1H), 1.66 (q, 2H), 1.49 (m, 2H) 1.44 (s, 3H), 1.48 (t, 2H), 1.36 (m, 2H), 1.34 (d, 3H) 1.11 (s, 6H) ppm. Mass: ESI [M+Na]⁺: 499.215; Elemental anal. calcd for $C_{23}H_{27}BF_6O_3$; C, 58.01; H, 5.31; F, 23.97; B, 2.27. found C, 58.06; H, 5.34; F, 23.99; B, 2.25.

Compound D: ¹H NMR (500 MHz, CDCl₃) δ7.20 (s, 1H), 3.17 (m, 1H), 2.35 (s, 6H), 1.78 (t, 1H), 1.71 (m, 2H), 1.49 (m, 2H), 1.48 (t, 2H), 1.43 (s, 3H), 1.38 (m, 2H) 1.34 (d, 3H) 1.11 (s, 6H) ppm. Mass: ESI [M+Na]⁺: 391.215; Elemental anal. calcd for $C_{23}H_{33}BO_3$; C, 75.1; H, 9.03; B, 2.94. found C, 75.16; H, 9.06; B, 2.89.

Compound E: ¹H NMR (500 MHz, CDCl₃) δ6.9 (s, 1H), 3.73 (s, 6H), 3.17 (m, 1H), 1.82 (t, 2H), 1.71 (m, 2H), 1.49 (m, 2H), 1.48 (t, 2H), 1.43 (s, 3H), 1.37 (t, 2H), 1.34 (d, 3H), 1.11 (s, 6H) ppm. Mass: ESI [M+Na]⁺: 423.25; Elemental anal. calcd for $C_{23}H_{33}BO_5$; C, 69.01; H, 8.32; B, 2.74. found C, 69.05; H, 8.33; B, 2.77.

Compound F: ¹H NMR (500 MHz, CDCl₃) δ7.1 (s, 1H), 3.17 (m, 1H), 2.59 (q, 4H), 1.82 (t, 2H), 1.78 (t, 1H), 1.71 (m, 2H), 1.44 (s, 3H), 1.38 (m, 2H), 1.34 (d, 3H), 1.24 (t, 6H), 1.11 (s, 6H) ppm. Mass: ESI [M+Na]⁺: 419.29; Elemental anal. calcd for $C_{25}H_{37}BO_3$; C, 75.75; H, 9.42; B, 2.65. found C, 75.72; H, 9.44; B, 2.66.

Compound G: ¹H NMR (500 MHz, CDCl₃) δ6.9 (s, 1H), 5.90 (s, 2H), 3.17 (m, 1H), 1.82 (t, 2H), 1.78 (t, 1H), 1.71 (m, 2H), 1.49 (m, 2H), 1.44 (s, 3H), 1.42 (t, 2H), 1.38 (m, 2H), 1.34 (d, 3H), 1.11 (s, 6H) ppm. Mass: ESI [M+Na]⁺: 407.21; Elemental anal. calcd for $C_{22}H_{29}BO_5$; C, 68.76; H, 7.63; B, 2.85. found C, 68.77; H, 7.65; B, 2.84.

Compound H: ¹H NMR (500 MHz, CDCl₃) δ6.67 (s, 1H), 4.2 (bs, 2H). 3.7 (t, 4H), 3.17 (m, 1H) 2.9 (t, 4H), 1.86 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 463.28 Elemental anal. calcd for $C_{25}H_{37}BN2O_4$; C, 68.16; H, 8.43; B, 2.44; N, 6.46. found C, 68.16; H, 8.44; B, 2.41.

Compound I: ¹H NMR (500 MHz, CDCl₃) δ6.4 (s, 1H), 4.15 (bs, 4H). 3.17 (m, 1H), 1.82 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 463.28 Elemental anal. calcd for $C_{21}H_{31}BN2O_3$; C, 68.14; H, 8.44; B, 2.94; N, 7.56. found C, 68.14; H, 8.42; N, 7.55.

Compound J: ¹H NMR (500 MHz, CDCl₃) δ7.8 (s, 1H), 8.01 (bs, 2H), 3.17 (m, 1H), 2.06 (s, 6H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 477.28 Elemental anal. calcd for $C_{25}H_{35}BN_2O_5$; C, 66.04; H, 7.74; B, 2.38; N, 6.17. found C, 66.02; H, 7.74; B, 2.36; N, 6.16.

Compound K: ¹H NMR (500 MHz, CDCl₃) δ6.4 (s, 1H), 4.02 (bs, 2H), 3.17 (m, 1H), 2.78 (d, 6H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 421.27 Elemental anal. calcd for $C_{23}H_{35}BN2O_3$; C, 69.50; H, 8.83; B, 2.75; N, 7.05. found C, 69.51; H, 8.82; B, 2.77; N, 7.04.

Compound L: ¹H NMR (500 MHz, CDCl₃) δ7.56 (s, 1H), 8.03 (s, 1H), 5.07 (bs, 1H), 3.17 (m, 1H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 403.23 Elemental anal. calcd for $C_{22}H_{29}BN_2O_3$; C, 69.47; H, 7.66; B, 2.83; N, 7.35. found C, 69.47; H, 7.65; B, 2.82; N, 7.33.

Compound M: ¹H NMR (500 MHz, CDCl₃) δ6.8 (s, 1H), 5.2 (bs, 2H), 3.17 (m, 1H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 553.16 Elemental anal. calcd for $C_{21}H_{31}BN_2O_9S_2$; C, 47.55; H, 5.88; B, 2.05; N, 5.24; S, 12.09. found C, 47.54; H, 5.89; B, 2.04; N, 5.24; S, 12.08.

Compound N: ¹H NMR (500 MHz, CDCl₃) δ7.3 (s, 1H), 3.17 (m, 1H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 555.12 Elemental anal. calcd for $C_{21}H_{29}BO_{11}S_2$; C, 47.45; H, 5.46; B, 2.05; S, 12.09. found C, 47.44; H, 5.45; B, 2.06; S, 12.1.

Compound O: ¹H NMR (500 MHz, CDCl₃) δ6.8 (s, 1H), 3.17 (m, 1H), 1.85 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]⁺: 658.96 Elemental anal. calcd for $C_{21}H_{27}BCl_6O_5Si_2$; C, 39.45; H, 4.25; B, 1.66; Si, 8.79; Cl, 33.29. found C, 39.44; H, 4.25; B, 1.68; Si, 8.78; Cl, 33.30.

Compound P: ¹H NMR (500 MHz, CDCl₃) δ6.9 (s, 1H), 5.89 (m, 2H), 5.24 (m, 2H), 5.23 (m, 2H) 4.65 (d, 4H), 3.17 (m, 1H), 1.82 (t, 2H), 1.71 (m, 2H), 1.49 (m, 2H), 1.48 (t, 2H), 1.43 (s, 3H), 1.37 (t, 2H), 1.34 (d, 3H), 1.11 (s, 6H) ppm. Mass: ESI [M+Na]⁺: 475.27; Elemental anal. calcd for $C_{27}H_{37}BO_5$; C, 71.69; H, 8.29; B, 2.34. found C, 71.68; H, 8.28; B, 2.33.

Compound Q: ¹H NMR (500 MHz, CDCl₃) δ8.2 (s, 1H), 3.18 (m, 1H), 1.82 (t, 2H), 1.78 (t, 1H), 1.71 (m, 2H), 1.49 (m, 2H) 1.44 (s, 3H), 1.48 (t, 2H), 1.36 (m, 2H), 1.34 (d, 3H) 1.11 (s, 6H) ppm. Mass: ESI [M+Na]⁺: 453.19; Elemental anal. calcd for $C_{21}H_{27}BN_2O_7$; C, 58.69; H, 6.31; N, 6.55; B, 2.57. found C, 58.69; H, 6.33; N, 6.54; B, 2.56.

Compound R: ¹H NMR (500 MHz, CDCl₃) δ8.1 (s, 1H), 3.18 (m, 1H), 1.82 (t, 2H), 1.78 (t, 1H), 1.71 (m, 2H), 1.49 (m, 2H) 1.44 (s, 3H), 1.48 (t, 2H), 1.36 (m, 2H), 1.34 (d, 3H) 1.11 (s, 6H) ppm. Mass: ESI [M+Na]⁺: 313.21; Elemental anal. calcd for $C_{23}H_{27}BN_2O_3$; C, 70.78; H, 6.92; N, 7.18; B, 2.77. found C, 70.77; H, 6.92; N, 7.16; B, 2.78.

Compound S: ¹H NMR (500 MHz, CDCl₃) 67.4 (s, 1H), 3.18 (m, 1H), 1.82 (t, 2H), 1.78 (t, 1H), 1.71 (m, 2H), 1.49 (m, 2H) 1.44 (s, 3H), 1.48 (t, 2H), 1.36 (m, 2H), 1.34 (d, 3H) 1.11 (s, 6H) ppm. Mass: ESI [M+Na]⁺: 399.21; Elemental anal. calcd for $C_{21}H_{27}BF_2O_3$; C, 67.64; H, 7.23; F, 10.12; B, 2.83. found C, 67.65; H, 7.22; F, 10.12; B, 2.84.

Compound T: ¹H NMR (500 MHz, CDCl₃) δ7.2 (s, 1H), 3.18 (m, 1H), 1.82 (t, 2H), 1.78 (t, 1H), 1.71 (m, 2H), 1.49 (m, 2H) 1.44 (s, 3H), 1.48 (t, 2H), 1.36 (m, 2H), 1.34 (d, 3H) 1.11 (s, 6H) ppm. Mass: ESI [M+Na]⁺: 431.143; Elemental anal. calcd for $C_{21}H_{27}BCl_2O_3$; C, 61.64; H, 6.56; Cl, 17.33; B, 2.65. found C, 61.66; H, 6.56; Cl, 17.32; B, 2.64.

Compound U: ¹H NMR (500 MHz, CDCl₃) δ6.59 (s, 1H), 9.1 (s, 2H), 8.03 (s, 1H), 3.18 (m, 1H), 1.78 (t, 1H), 1.75 (t, 2H), 1.64 (m, 2H), 1.49 (m, 2H), 1.48 (t, 2H), 1.44 (s, 3H), 1.38 (m, 2H), 1.34 (d, 3H) 1.11 (s, 6H) ppm. Mass: ESI [M+Na]⁺: 394.226; Elemental anal. calcd for $C_{21}H_{30}BNO_4$; C, 67.95; H, 8.14; N, 3.77; B, 2.91. found C, 67.98; H, 8.15; N, 3.76; B, 2.91.

Compound V: ¹H NMR (500 MHz, CDCl₃) 6.89 (s, 1H), 9.1 (s, 2H), 8.03 (s, 1H), 2.94 (m, 1H), 1.78 (t, 1H), 1.71 (m, 2H), 1.49 (m, 2H), 1.48 (t, 2H), 1.44 (s, 3H), 1.38 (m, 2H), 1.34 (d, 3H) 1.11 (s, 6H) ppm. Mass: ESI [M+Na]⁺: 401.188 Elemental anal. calcd for $C_{21}H_{29}BO_4S$; C, 64.95; H, 7.65; S, 8.24; B, 2.73. found C, 64.96; H, 7.66; S, 8.23; B, 2.72.

Compound W: $^1$H NMR (500 MHz, CDCl$_3$) δ6.54 (s, 1H), 9.1 (s, 2H), 3.34 (s, 2H), 2.34 (m, 1H), 1.53 (t, 2H), 1.49 (m, 2H), 1.46 (t, 2H), 1.43 (t, 1H) 1.41 (m, 2H), 1.38 (m, 2H), 1.26 (s, 3H) 1.17 (d, 3H) 1.12 (s, 6H) ppm. Mass: ESI [M+Na]$^+$: 393.236; Elemental anal. calcd. For C$_{22}$H$_{31}$BO$_4$; C, 71.36; H, 8.44; B, 2.92. found C, 71.36; H, 8.43; B, 2.93.

Compound X: $^1$H NMR (500 MHz, CDCl$_3$) δ6.59 (s, 1H), 9.1 (s, 2H), 3.62 (s, 3H), 2.95 (m, 1H), 1.78 (t, 1H), 1.75 (t, 2H), 1.64 (m, 2H), 1.49 (m, 2H), 1.48 (t, 2H), 1.44 (s, 3H), 1.38 (m, 2H), 1.34 (d, 3H) 1.11 (s, 6H) ppm. Mass: ESI [M+Na]$^+$: 408.242; Elemental anal. calcd for C$_{22}$H$_{32}$BNO$_4$; C, 68.59; H, 8.34; N, 3.65; B, 2.81. found C, 68.58; H, 8.35; N, 3.65; B, 2.83.

Compound Y: $^1$H NMR (500 MHz, CDCl$_3$) δ6.7 (s, 1H), 3.73 (s, 6H). 3.62 (s, 3H), 2.94 (m, 1H), 1.78 (t, 1H), 1.75 (t, 2H), 1.64 (m, 2H), 1.49 (m, 2H), 1.48 (t, 2H), 1.44 (s, 3H), 1.38 (m, 2H), 1.34 (d, 3H) 1.11 (s, 6H) ppm. Mass: ESI [M+Na]$^+$: 436.27; Elemental anal. calcd for C$_{24}$H$_{36}$BNO$_4$; C, 69.73; H, 8.76; N, 3.38; B, 2.64. found C, 69.75; H, 8.77; N, 3.38; B, 2.65.

Compound Z: $^1$H NMR (500 MHz, CDCl$_3$) δ6.9 (s, 1H), 2.98 (m, 1H), 2.21 (m, 1H), 1.82 (t, 2H), 1.78 (t, 1H), 1.71 (m, 2H), 1.49 (m, 2H), 1.48 (t, 2H), 1.44 (s, 3H), 1.38 (m, 2H), 1.11 (s, 6H), 1.01 (d, 6H) ppm. Mass: ESI [M+Na]$^+$: 423.242; Elemental anal. calcd for C$_{23}$H$_{33}$BO$_5$; C, 69.24; H, 8.31; B, 2.70. found C, 69.26; H, 8.35; B, 2.72.

Compound AA: $^1$H NMR (500 MHz, CDCl$_3$) δ7.3 (s, 1H), 3.18, (m, 1H), 2.08 (s, 6H), 1.82 (t, 2H), 1.78 (t, 1H), 1.71 (m, 2H), 1.49 (m, 2H), 1.48 (t, 2H), 1.44 (s, 3H), 1.36 (m, 2H), 1.34 (d, 3H) 1.11 (s, 6H) ppm. Mass: ESI [M+Na]$^+$: 479.236; Elemental anal. calcd for C$_{25}$H$_{33}$BO$_7$; C, 65.76; H, 7.29; B, 2.37. found C, 65.77; H, 7.30; B, 2.38.

Compound AB: $^1$H NMR (500 MHz, CDCl$_3$) δ7.1 (s, 1H), 8.01 (bs, 2H), 10.1 (bs, 1H), 2.94 (m, 1H), 2.06 (s, 6H), 1.85 (t, 2H), 1.78 (t, 1H), 1.61 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]$^+$: 476.28 Elemental anal. calcd for C$_{25}$H$_{36}$BN$_3$O$_4$; C, 66.24; H, 8.04; B, 2.38; N, 9.17. found C, 66.25; H, 8.02; B, 2.39; N, 9.16.

Compound AC: $^1$H NMR (500 MHz, CDCl$_3$) δ6.66 (s, 1H), 3.17 (m, 1H), 2.83 (s, 12H), 1.82 (t, 2H), 1.78 (t, 1H), 1.71 (m, 2H), 1.49 (m, 2H), 1.46 (t, 2H), 1.44 (s, 3H), 1.38 (m, 2H), 1.34 (d, 3H), 1.11 (s, 6H) ppm. Mass: ESI [M+Na]$^+$: 449.302 Elemental anal. calcd for C$_{25}$H$_{39}$BN$_2$O$_3$; C, 70.42; H, 9.22; B, 2.54; N, 6.52. found C, 70.43; H, 9.21; B, 2.55; N, 6.53.

Compound AD: $^1$H NMR (500 MHz, CDCl$_3$) δ6.85 (s, 1H), 9.1 (s, 2H), 2.75 (t, 3H), 1.83 (t, 2H) 1.78 (t, 1H), 1.56 (m, 2H), 1.49 (m, 2H), 1.48 (t, 2H), 1.44 (s, 3H), 1.11 (s, 6H) ppm. Mass: ESI [M+Na]$^+$: 395.201; Elemental anal. calcd for C$_{20}$H$_{25}$BO$_6$; C, 64.55; H, 6.83; B, 2.91. found C, 64.54; H, 6.84; B, 2.92.

Compound AE: $^1$H NMR (500 MHz, CDCl$_3$) δ6.83 (s, 1H), 9.1 (s, 2H), 4.33 (t, 1H), 1.89 (m, 2H) 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 465.51; Elemental anal. calcd for C$_{21}$H$_{26}$BF$_3$O$_6$; C, 57.05; H, 5.91; B, 2.39; F, 12.89. found C, 57.06; H, 5.92; B, 2.40; F, 12.88.

Compound AF: $^1$H NMR (500 MHz, CDCl$_3$) δ6.83 (s, 1H), 9.1 (s, 2H), 3.83 (t, 1H), 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 449.184; Elemental anal. calcd for C$_{21}$H$_{26}$BF$_3$O$_5$; C, 59.18; H, 6.15; B, 2.59; F, 13.35. found C, 59.16; H, 6.16; B, 2.58; F, 13.35.

Compound AG: $^1$H NMR (500 MHz, CDCl$_3$) δ6.83 (s, 1H), 9.1 (s, 2H), 4.13 (m, 1H), 2.61 (bs, 2H), 1.93 (m, 2H), 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 396.206; Elemental anal. calcd for C$_{20}$H$_{28}$BNO$_5$; C, 64.36; H, 7.56; B, 2.9; N, 3.75. found C, 64.34; H, 7.54; B, 2.89; N, 3.77.

Compound AH: $^1$H NMR (500 MHz, CDCl$_3$) δ6.83 (s, 1H), 9.1 (s, 2H), 4.76 (m, 1H), 3.5 (bs, 1H), 1.87 (m, 2H), 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 397.20; Elemental anal. calcd for C$_{20}$H$_{27}$BO$_6$; C, 64.26; H, 7.26; B, 2.89. found C, 64.25; H, 7.24; B, 2.88.

Compound AI: $^1$H NMR (500 MHz, CDCl$_3$) δ6.83 (s, 1H), 9.1 (s, 2H), 5.43 (m, 1H), 2.25 (s, 3H), 1.93 (m, 2H), 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 439.210; Elemental anal. calcd for C$_{22}$H$_{29}$BO$_7$; C, 63.26; H, 7.02; B, 2.62. found C, 63.26; H, 7.04; B, 2.63.

Compound AJ: $^1$H NMR (500 MHz, CDCl$_3$) δ6.83 (s, 1H), 9.1 (s, 2H), 8.10 (bs, 1H), 5.13 (m, 1H), 2.15 (s, 3H), 1.97 (m, 2H), 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 438.214; Elemental anal. calcd for C$_{22}$H$_{30}$BNO$_6$; C, 63.64; H, 7.28; O, 23.26; B, 2.60; N, 3.35. found C, 63.65; H, 7.30; N, 3.34.

Compound AK: $^1$H NMR (500 MHz, CDCl$_3$) δ6.83 (s, 1H), 9.1 (s, 2H), 4.13 (m, 1H), 3.05 (m, 1H), 2.45 (d, 3H), 1.83 (m, 2H), 1.82 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 410.21; Elemental anal. calcd for C$_{21}$H$_{30}$BNO$_5$; C, 65.15; H, 7.84; B, 2.76; N, 3.96. found C, 65.14; H, 7.85; B, 2.76; N, 3.95.

Compound AL: $^1$H NMR (500 MHz, CDCl$_3$) δ6.83 (s, 1H), 9.1 (s, 2H), 4.13 (m, 1H), 3.05 (m, 1H), 2.25 (d, 6H), 1.82 (t, 2H), 1.80 (m, 2H) 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 424.235; Elemental anal. calcd for C$_{22}$H$_{32}$BNO$_5$; C, 65.85; H, 8.05; B, 2.68; N, 3.49. found C, 65.82; H, 8.02; B, 2.67; N, 3.51.

Compound AM: $^1$H NMR (500 MHz, CDCl$_3$) δ6.83 (s, 1H), 9.1 (s, 2H), 6.47 (d, 1H), 5.03 (t, 1H), 4.18 (dd, 1H), 4.04 (dd, 1H), 2.05 (m, 2H, 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 423.26; Elemental anal. calcd for C$_{22}$H$_{29}$BO$_6$; C, 66.21; H, 7.35; B, 2.69. found C, 66.23; H, 7.36; B, 2.68.

Compound AN: $^1$H NMR (500 MHz, CDCl$_3$) δ6.83 (s, 1H), 9.1 (s, 2H), 4.13 (t, 1H), 2.24 (d, 4H), 1.82 (t, 2H), 1.80 (m, 2H) 1.78 (t, 1H), 1.50 (m, 6H), 1.49 (m, 2H), 1.48 (t, 2H), 1.44 (s, 3H), 1.38 (m, 2H), 1.11 (s, 6H) ppm. Mass: ESI [M+Na]$^+$: 464.235; Elemental anal. calcd for C$_{25}$H$_{36}$BNO$_5$; C, 68.05; H, 8.25; B, 2.48; N, 3.19. found C, 68.10; H, 8.22; B, 2.47; N, 3.21.

Compound AO: $^1$H NMR (500 MHz, CDCl$_3$) δ6.83 (s, 1H), 9.1 (s, 2H), 4.13 (t, 1H), 3.65 (t, 4H) 2.34 (d, 4H), 1.82 (t, 2H), 1.80 (m, 2H) 1.78 (t, 1H), 1.49 (m, 2H), 1.48 (t, 2H), 1.44 (s, 3H), 1.38 (m, 2H), 1.11 (s, 6H) ppm. Mass: ESI [M+Na]$^+$: 466.35; Elemental anal. calcd for C$_{24}$H$_{34}$BNO$_6$; C, 65.08; H, 7.69; B, 2.24; N, 3.17. found C, 65.09; H, 7.71; B, 2.25; N, 3.18.

Compound AP: $^1$H NMR (500 MHz, CDCl$_3$) δ6.83 (s, 1H), 9.1 (s, 2H), 4.13 (t, 1H), 2.4 (q, 4H), 1.82 (t, 2H), 1.80 (m, 2H) 1.78 (t, 1H), 1.49 (m, 2H), 1.48 (t, 2H), 1.44 (s, 3H), 1.38 (m, 2H), 1.11 (s, 6H), 1.05 (t, 6H) ppm. Mass: ESI [M+Na]$^+$: 452.28; Elemental anal. calcd for C$_{24}$H$_{36}$BNO$_5$; C, 67.18; H, 8.49; B, 2.51; N, 3.28. found C, 67.19; H, 8.47; B, 2.53; N, 3.27.

Compound AQ: $^1$H NMR (500 MHz, CDCl$_3$) δ6.83 (s, 1H), 9.76 (s, 1H), 9.1 (s, 2H) 3.89 (t, 1H), 2.08 (m, 2H) 1.83 (t, 2H), 1.78 (t, 1H), 1.49 (m, 2H), 1.48 (t, 2H), 1.44 (s, 3H), 1.38 (m, 2H), 1.11 (s, 6H) ppm. Mass: ESI [M+Na]+: 409.34; Elemental anal. calcd for $C_{21}H_{27}BO_6$; C, 65.37; H, 7.08; B, 2.91. found C, 65.36; H, 7.09; B, 2.92.

Compound AR: $^1$H NMR (500 MHz, CDCl$_3$) δ6.83 (s, 1H), 9.1 (s, 2H) 2.93 (m, 1H), 1.83 (t, 2H), 1.78 (t, 1H), 1.71 (m, 2H) 1.49 (m, 2H), 1.48 (t, 2H), 1.44 (s, 3H), 1.38 (m, 2H), 1.11 (s, 6H), 0.59 (m, 1H), 0.34 (m, 4H) ppm. Mass: ESI [M+Na]+: 409.34; Elemental anal. calcd for $C_{21}H_{27}BO_6$; C, 65.37; H, 7.08; B, 2.91. found C, 65.34; H, 7.09; B, 2.92.

Compound AS: $^1$H NMR (500 MHz, CDCl$_3$) δ7.3-7.5 (m, 5H), 6.83 (s, 1H), 6.59 (d, 1H) 9.1 (s, 2H) 2.8 (m, 1H), 1.83 (t, 2H), 1.78 (t, 1H), 1.71 (m, 2H) 1.49 (m, 2H), 1.48 (t, 2H), 1.44 (s, 3H), 1.38 (m, 2H), 1.11 (s, 6H) ppm. Mass: ESI [M+Na]+: 484.23; Elemental anal. calcd for $C_{27}H_{32}BNO_5$; C, 70.81; H, 6.72; B, 2.31; N, 3.04. found C, 70.84; H, 6.73; B, 2.32; N, 3.06.

Compound AT: $^1$H NMR (500 MHz, CDCl$_3$) δ7.05 (dd, 2H), 6.83 (s, 1H), 6.59 (t, 1H), 6.43 (d, 2H) 9.1 (s, 2H), 3.48 (t, 2H), 3.28 (m, 1H), 1.83 (t, 2H), 1.78 (t, 1H), 1.71 (m, 2H) 1.49 (m, 2H), 1.48 (t, 2H), 1.44 (s, 3H), 1.38 (m, 2H), 1.11 (s, 6H) ppm. Mass: ESI [M+Na]+: 486.253; Elemental anal. calcd for $C_{27}H_{34}BNO_5$; C, 70.01; H, 7.43; B, 2.32; N, 3.04. found C, 70.06; H, 7.44; B, 2.35; N, 3.06.

Compound AU: $^1$H NMR (500 MHz, CDCl$_3$) δ6.83 (s, 1H), 9.1 (s, 2H), 5.62 (d, 1H), 4.98 (d, 1H), 2.23 (t, 2H), 1.83 (t, 2H), 1.78 (t, 1H), 1.71 (m, 2H), 1.49 (m, 2H), 1.48 (t, 2H), 1.44 (s, 3H), 1.41 (m, 2H), 1.11 (s, 6H) ppm. Mass: ESI [M+Na]+: 393.17; Elemental anal. calcd for $C_{21}H_{27}BO_5$ C, 68.17; H, 7.38; B, 2.91. found C, 68.16; H, 7.35; B, 2.94.

Compound AV: $^1$H NMR (500 MHz, CDCl$_3$) δ6.83 (s, 1H), 9.1 (s, 2H), 10.05 (bs, 1H), 2.73 (m, 1H), 1.73 (t, 2H), 1.78 (t, 1H), 1.63 (m, 2H) 1.49 (m, 2H), 1.48 (t, 2H), 1.44 (s, 3H), 1.38 (m, 2H), 1.11 (s, 6H), 0.59 (m, 1H), 0.34 (m, 4H) ppm. Mass: ESI [M+Na]+: 420.24; Elemental anal. calcd for $C_{23}H_{32}BNO_4$; C, 69.57; H, 8.18; B, 2.71; N, 3.56. found C, 69.55; H, 8.13; B, 2.71; N, 3.58.

Compound AW: $^1$H NMR (500 MHz, CDCl$_3$) δ6.83 (s, 1H), 9.1 (s, 2H), 2.74 (m, 1H), 1.73 (t, 2H), 1.78 (t, 1H), 1.63 (m, 2H) 1.49 (m, 2H), 1.48 (t, 2H), 1.44 (s, 3H), 1.38 (m, 2H), 1.11 (s, 6H), 0.59 (m, 1H), 0.34 (m, 4H) ppm. Mass: ESI [M+Na]+: 437.02; Elemental anal. calcd for $C_{23}H_{31}BO_4S$; C, 66.57; H, 7.58; B, 2.61; S, 7.78. found C, 66.55; H, 7.59; B, 2.62; S, 7.77.

Compound AX: $^1$H NMR (500 MHz, CDCl$_3$) δ6.83 (s, 1H), 9.1 (s, 2H), 10.1 (bs, 1H), 3.53 (t, 1H), 1.83 (t, 2H), 1.78 (t, 1H), 1.64 (m, 2H), 1.49 (m, 2H), 1.48 (t, 2H), 1.44 (s, 3H), 1.38 (m, 2H), 1.11 (s, 6H) ppm. Mass: ESI [M+Na]+: 448.194; Elemental anal. calcd for $C_{21}H_{27}BF_3O_4N$; C, 59.38; H, 6.45; B, 2.59; F, 13.40; N, 3.29. found C, 59.34; H, 6.43; B, 2.58; F, 13.41; N, 3.28.

Compound AY: $^1$H NMR (500 MHz, CDCl$_3$) δ7.95 (d, 2H), 7.47 (t, 1H), 7.37 (dd, 2H), 6.83 (s, 1H), 9.1 (bs, 2H), 5.48 (t, 1H), 2.16 (m, 1H), 1.83 (t, 2H), 1.78 (t, 2H), 1.49 (m, 2H), 1.48 (t, 2H), 1.44 (s, 3H), 1.38 (m, 2H), 1.11 (s, 6H) ppm. Mass: ESI [M+Na]+: 501.218; Elemental anal. calcd for $C_{27}H_{31}BO_7$; C, 67.71; H, 6.59; B, 2.26. found C, 67.74; H, 6.58; B, 2.26.

Compound AZ: For step 1 to 7 Ref: (Pereira A. R.; Strangman, W. K.; Marion, F.; Feldberg, L.; Roll, D.; Mallon, R.; Hollander, I.; Andersen, R. J. J. Med. Chem. 2010, 53, 8523)

Step 1: Synthesis of compound 13 (2-hydroxy-4,5-dimethoxybenzaldehyde): To a solution of 3,4,5-trimethoxybenzaldehyde (5 g, 25.510 mmol) in CH$_2$Cl$_2$ (125 ml) at 0° C., BBr$_3$ (6.39 g, 25.510 mmol) was added. The resulting dark mixture was stirred at rt for 9 h. Water (100 mL) was charged and the mixture was stirred for 10 min, the aqueous phase was extracted by CH$_2$Cl$_2$. Organic phase was dried over Na$_2$SO$_4$, and evaporated under reduced pressure. The resulting residue was purified by silica gel column chromatography using plain dichloromethane as eluent, afforded the 2-hydroxy-4,5-dimethoxybenzaldehyde 13 (4.3 g, 87%) isolated as yellow solid. Mp 105-107° C.; $^1$H NMR (CDCl$_3$, 400 MHz): δ 11.40 (br. s, 1H), 9.70 (s, 1H), 6.91 (s, 1H), 6.48 (s, 1H), 3.94 (s, 3H), 3.88 (s, 3H) ppm. $^{13}$C NMR (CDCl$_3$. 125 MHz): 194.0, 159.3, 157.3, 142.9, 113.3, 112.9, 100.1, 56.4, 56.3. HRMS (ESI) m/z: [M+H]+ calcd for C9H10O4+H+ 183.0657. Found 183.0653.

Step 2: Synthesis of compound 13 (4,5-dimethoxy-2-(methoxymethoxy)benzaldehyde)

A solution of 5 (1 g, 5.49 mmol) in anhydrous CH$_2$Cl$_2$ under nitrogen was cooled to 0° C., to it diisopropyl ethylamine (DIPEA) (1.77 g, 13.736 mmol) and MOMCl (0.66 g, 8.241 mmol) were added. The reaction mixture was stirred at room temperature for 1 h. After completion of the reaction, water was added extracted with dichloromethane. The organic extract was washed with brine, dried over anhydrous Na$_2$SO$_4$ and evaporated under reduced pressure, the resultant product 14 (2.15 g, 98%) as colorless liquid was used for further reaction without purification. $^1$H NMR (CDCl$_3$, 400 MHz): δ 10.34 (s, 1H), 7.30 (s, 1H), 6.77 (s, 1H), 5.26 (s, 2H), 3.95 (s, 3H), 3.88 (s, 3H), 3.54 (s, 3H) ppm. $^{13}$C NMR (CDCl$_3$, 125 MHz): 188.0, 156.4, 155.5, 144.4, 118.1, 108.2, 99.9, 95.4, 56.4, 56.2, 56.1. HRMS (ESI) m/z: [M+H]+ calcd for C11H14O5+H+ 227.0919. Found 227.0897

Step 3: Synthesis of compound 15 (4,5-dimethoxy-2-(methoxymethoxy)phenyl methanol)

The solution of compound 14 (1 g, 4.423 mmol) and sodium hydroxide (0.177 g, 4.423 mmol) in MeOH was taken in round bottom flask, to it NaBH$_4$ (0.25 g, 6.635 mmol) was added. The reaction mixture was stirred for half hour at room temperature. The reaction mixture was concentrated under reduced pressure to remove MeOH, added water and was extracted with ethyl acetate, washed with brine, dried over anhydrous Na$_2$SO$_4$ and evaporated under reduced pressure afforded colorless liquid 15 (0.99 g, 98%), the resultant product was used for further reaction without purification. $^1$H NMR (200 MHz, CDCl$_3$): δ 6.86 (s, 1H), 6.75 (s, 1H), 5.16 (s, 2H), 4.65-4.62 (d, J=5.29 Hz, 2H), 3.87 (s, 3H), 3.86 (s, 3H), 3.52 (s, 3H) ppm. $^{13}$C NMR (CDCl$_3$, 100 MHz): 149.15, 149.0, 144.1, 122.1, 112.56, 101.3, 96.0, 60.7, 56.3, 56.1, 55.9. HRMS (ESI) m/z: [M+Na]+ calcd for C11H16O5+Na+ 251.0896. Found 251.0874

Step 4: Synthesis of compound 16 (2-hydroxy-4,5-dimethoxybenzyl)triphenylphosphonium hydrogen bromide salt): A solution of compound 15 (1 g, 4.384 mmol) in acetonitrile was taken, to this PPh$_3$HBr (1.8 g, 5.260 mmol) was added at room temperature and refluxed for about 2 h. After completion of the reaction solvent was removed under reduced pressure and washed with ether, gave compound 16 (1.69 g, 90%) as a white amorphous solid. Mp 240-242° C.; $^1$H NMR (CDCl$_3$, 400 MHz): δ 8.62 (br. s, 1H), 7.75-7.71 (m, 3H), 7.60-7.52 (m, 12H), 7.03 (s, 1H), 6.44-6.43 (d, J=12.8 Hz, 1H), 4.48-4.45 (d, J=12 Hz, 2H), 3.69 (s, 3H), 3.48 (s, 3H) ppm. $^{13}$CNMR (CDCl$_3$, 125 MHz): 134.7, 134.7, 134.3, 130.0, 129.9, 113.9, 113.90, 101.9, 101.9, 56.3, 55.9, 25.3, 24.8. HRMS (ESI) m/z: [M]+ calcd for C27H26O3P 429.1620 (—HBr). Found 429.1615 (—HBr).

Step 5: Synthesis of compound 18 a starting material 3-(2,6,6-trimethylcyclohex-1-enyl)propanoic acid: 17 g (425.001 mmol) of NaOH was dissolved in water to make a 70 ml solution in a 250 ml conical flask with a magnetic stirrer. The alkali solution was then cooled in an ice bath and 17 g (106.25 mmol) of bromine was added to the solution after stirring for 1 h, 4.5 g (23.19 mmol) of dihydro-β-ionone 17 in 10 ml of dioxane was dropped into the solution, the stirring was continued at rt for 4 h. The excess of hypobromite was neutralized with 10% sodium bisulfite and solution was extracted with diethylether to remove remaining impurities. Acidification of the alkaline solution with conc. hydrochloric acid was done under usual conditions and workup gave 18 (4.1 g, 90.1%) as a colorless liquid. $^1$H NMR (CDCl$_3$, 400 MHz): δ 2.44-2.39 (m, 2H), 2.37-2.31 (m, 2H), 1.93-1.89 (t, J=8 Hz, 2H), 1.61 (s, 3H), 1.58-1.54 (s, 2H), 1.44-1.41 (m, 2H), 1.00 (s, 6H). $^{13}$CNMR (CDCl$_3$, 100 MHz): 180.3, 135.4, 128.5, 39.7, 34.9, 34.7 (multiple merged peaks), 28.4, 23.5, 19.6, 19.4. HRMS (ESI) m/z: [M+H]$^+$ calcd for C12H20O2+H$^+$ 197.1541. Found 197.1530.

Step 6: Synthesis of compound 19 (5,6-dimethoxy-2-(2-(2,6,6-trimethylcyclohex-1-enyl)ethyl)benzofuran): The intermediate 16 (2 g, 4.651 mmol) was taken in dry DCM along with dihydro-β-ionicacid 18 (0.91 g, 4.65 mmol) in round bottom flask, in dry conditions and cooled to 0° C. To it DCC (2.87 g, 13.953 mmol) and DMAP (0.56 g, 4.651 mmol) were added and stirred at room temperature for 18 h. DCM was evaporated under reduced pressure and the crude reaction mixture was dissolved in THF and to it was added triethylamine and refluxed for 3 h. THF was evaporated under reduced pressure and purified by column chromatography 5% ethyl acetate: hexane afforded 19 (1.42 g, 93%) as colorless oil. $^1$H NMR (400 MHz, CDCl$_3$): δ 6.93 (s, 1H), 6.85 (s, 1H), 6.20 (d, J=0.6 Hz, 1H), 3.81 (d, 6H), 2.70-2.66 (m, 2H), 2.34-2.30 (m, 2H), 1.87-1.85 (t, J=6.1 Hz, 2H), 1.58 (s, 3H), 1.54-1.44 (m, 2H), 1.51-1.49 (m, 2H), 0.96 (s, 6H). $^{13}$CNMR (CDCl$_3$, 100 MHz): 158.8, 149.1, 146.9, 146.1, 136.2, 128.1, 102.7, 101.0, 95.3, 56.4, 56.2, 39.7 (multiple merged peaks), 35.0, 32.7, 29.3, 28.5, 27.2, 19.8, 19.4 (merged peaks). HRMS (ESI) m/z: [M+H]$^+$ calcd for C21H28O3+H$^+$ 329.2117. Found 329.2099.

Step 7: Synthesis of compound 20: The solution of compound 19 (1 g, 3.049 mmol) was prepared in 2-nitro propane and cooled to 78° C., to it chlorosulfonic acid (1.06 g, 9.146 mmol) was added under inert atmosphere. The reaction mixture was stirred for 30 min. Then quenched with NaHCO$_3$ and extracted by ethyl acetate. The organic layer was dried over Na$_2$SO$_4$ and evaporated under reduced pressure and purified by column chromatography using 5% ethyl acetate:hexane afforded 20 (0.9 g, 90% yield) as colorless oil. $^1$H NMR (400 MHz, CDCl$_3$): δ 7.00 (s, 1H), 6.97 (s, 1H), 3.91 (s, 3H), 3.89 (s, 3H), 2.79-2.74 (m, 1H), 2.72-2.65 (m, 1H), 2.42 (d, J=13.0 Hz, 1H), 2.06-1.91 (m, 2H), 1.87-1.76 (m, 2H), 1.50-1.63 (m, 2H), 1.45-1.39 (m, 2H), 1.31 (s, 3H), 0.97 (s, 3H), 0.95 (s, 3H). $^{13}$CNMR (CDCl$_3$, 125 MHz): 151.2, 149.2, 146.4, 145.4, 124.3, 118.8, 102.4, 95.5, 56.6, 56.2, 52.6, 41.8, 37.6, 35.9, 33.5, 33.1, 24.9, 21.8, 21.3 (merged peaks), 18.8. HRMS (ESI) m/z: [M+H]$^+$ calcd for C21H28O3+H$^+$ 329.2117. Found 329.2105, [M+Na]$^+$ calcd for C21H28O3+Na$^+$ 351.1936. Found 351.1931

Step 8: Synthesis of compound 21: The solution of compound 20 (1 g, 3.048 mmol) was prepared in dry THF, and cooled to 0° C. under dry condition. To it n-BuLi (0.195 g, 3.048 mmol) was added and the reaction mixture was kept for 20 minutes stirring, to it triethyl borate (0.45 g, 3.048 mmol) was added and continued stirring for another 1 h at rt. Quenched with ammonium chloride solution and extracted by ethyl acetate. Concentrated under reduced pressure and purified by column chromatography using 6% ethyl acetate: hexane afforded 21 (1.043 g, 92%) as a colorless liquid. $^1$H NMR (400 MHz, CDCl$_3$) δ 7.18 (s, 1H), 6.83 (s, 2H), 3.96 (s, 3H), 3.93 (s, 3H), 2.80-2.73 (m, 2H), 2.42 (d, J=12.0 Hz, 1H), 2.03 (m, 2H, merged signals), 1.89-1.76 (m, 2H), 1.73-1.66 (m, 2H), 1.45-1.40 (m, 2H), 1.32 (s, 3H), 0.99 (s, 3H), 0.96 (s, 3H). $^{13}$C NMR (CDCl$_3$, 100 MHz) 153.0, 152.9, 151.0, 148.4, 124.3, 122.4, 107.1, 61.9, 56.7, 52.7, 41.8, 36.1, 33.5, 33.2 (merged peaks), 25.1, 21.9, 21.4, 18.9, 18.8. HRMS (ESI) m/z: [M+H]$^+$ calcd for C$_{21}$H$_{29}$BO$_5$+H$^+$ 372.2217. Found 372.2231.

Step 9: Synthesis of compound 22: To (0.5 g, 4.301 mmol) of dry aluminium chloride, 5 ml of dichloromethane was poured, then (0.245 g, 3.225 mmol) of crystalline thiourea was added in small portions and stirred for 20 minutes. The reaction mixture becomes transparent oily solution. Then compound 21 (0.1 g, 0.268 mmol) dissolved in dichloromethane was added to this over a period of 5 minutes and stirred for 2 h at rt. The excess of AlCl$_3$ was removed by quenching with ice and extracted by dichloromethane and then purified by column chromatography using 15% ethylacetate: hexane afforded 22 (0.077 g, 85% yield) as colorless liquid. $^1$H NMR (500 MHz, CDCl$_3$): δ 7.10 (s, 1H), 6.74 (s, 1H), 6.48 (br.s, 1H), 3.94 (s, 2H), 2.80-2.71 (m, 2H), 2.39 (d, J=10 Hz, 1H), 2.20-2.03 (m, 2H), 1.80-1.70 (m, 2H), 1.54-1.51 (m, 2H), 1.44-1.37 (m, 2H), 1.30 (s, 3H), 0.98 (s, 3H), 0.95 (s, 3H). $^{13}$C NMR (CDCl$_3$, 125 MHz): 153.4, 151.1, 147.9, 142.9, 124.3, 118.1, 114.1, 105.1, 52.6, 41.8, 37.7, 36.0, 33.5, 29.5, 25.0, 21.9, 21.4, 18.9, 18.8; HRMS (ESI) m/z: [M$^+$]: calcd for C$_{19}$H$_{25}$BO$_5$ 344.1795. Found 344.1761.

Biology:

1. Cytotoxic Assay

The MTT assay (MTT Assay (Legrier M E, Yang C P, Yan H G et al. Targeting protein translation in human non small lung cancer via combined MEK and mammalian target of rapamycin suppression. *Cancer Res* 67:11300-8(2007).) is useful for measuring the effect of a wide range of compounds on the in vitro growth of either normal or cancer cell lines. The assay was set up in a 96-well, flat-bottomed polystyrene microtiter plate. 3-5000 cells were suspended per well in appropriate growth medium, and the cells were added to replicate wells (triplicates were preferred). It was preferable to add the cells to the required number of wells in the plate prior to adding the drugs or the test agents. After the cells were added to the plate, it was placed on the incubator for overnight incubation, while the agents to be tested were being prepared. After overnight incubation drugs or test compounds were added at defined concentrations to each set of replicate wells and incubated for 48 hrs in CO$_2$ incubator. Most of these compounds were dissolved in dimethyl sulfoxide (DMSO) for the final addition. After 48 hr incubation, diluted the MTT stock solution (2.5 μg/ml) with an equal volume of tissue culture medium and added 20 μl of this solution directly to each well with a multichannel pipette. As with the adherent-cell method, return the plates to the incubator for a period of at least 4 h. After 4 hr incubation centrifuge the plates at 1000 g for 10 min at ambient temperature, followed by inversion of the plates and blotting of excess medium. Add 150 μl of working DMSO to solubilize the MTT formazan product. A standard micro plate reader with adjustable wavelength across the visible spectrum was used. The OD values at 570 nm obtained for each set of triplicates corresponding to a specific concentration of a test agent was then transferred into a spreadsheet program.

Results: Cytotoxicity assay based on MTT was performed on the panel of cancer cell lines using compound A and compound E as a test material. In order to determine the effect of compound A and compound E on cell proliferation and in relative $IC_{50}$ values, MCF-7, caco-2 & HCT-115 were treated with compound A and compound E at indicated concentrations (0.01, 0.1, 1, 10 μM) for 48 h. In the present study, compound A and compound E produced concentration dependent inhibition of cell proliferation. From the MTT based inhibition in cell proliferation, the calculated cell based $IC_{50}$ value of 2.6 μM and 2.4 μM in breast (MCF-7) and colon (caco-2) cell line were observed for compound A and 5.6, 3.7 and 3.1 μM in colon (caco-2, HCT-115) and breast (MCF-7) for compound E was calculated (FIG. 3). These results depicted that both compound A and compound E showed more effectiveness against colon cell proliferation as reflected by relative $IC_{50}$ values and therefore towards the colon cancer in general.

2. PI3K Inhibition Assays:

PI3K inhibition assay (PI3K Assay (Emmanuelle M, Huang Y, Yan H G et al. Targeting Protein Translation in Human Non-Small Cell Lung Cancer via Combined MEK and Mammalian Target of Rapamycin Suppression. *Cancer Res* 67:(23). (2007).) was carried out by PI3 Kinase activity/inhibitor assay kit, where PI3 kinase reaction was set up in Glutathione-coated strips/plate for inhibitor reaction. Kinase and inhibitors were pre-incubated for 10 minutes prior to the addition of PIP2 substrate. 5 μL of 5× kinase reaction buffer were added in each well followed by the further addition of 5 μL/well of PIP2 substrate. Then distilled $H_2O$ was added to each well so as to make up a final volume of 25 μL/well. Incubation was done at rt for 1 hour which was followed by washing the wells 3 times with 200 μL of 1×TBST per well and then 2 times with 200 μL of IX TBS per well. Then 100 μL of the Substrate TMB per well was added and then to keep for colour development in the dark for 5-20 minutes. However, appearance of the blue color to avoid over-development were monitored. 100 μL of the stop solution per well was used to stop the reaction. Readings were recorded at 450 nm.

Figure 4:
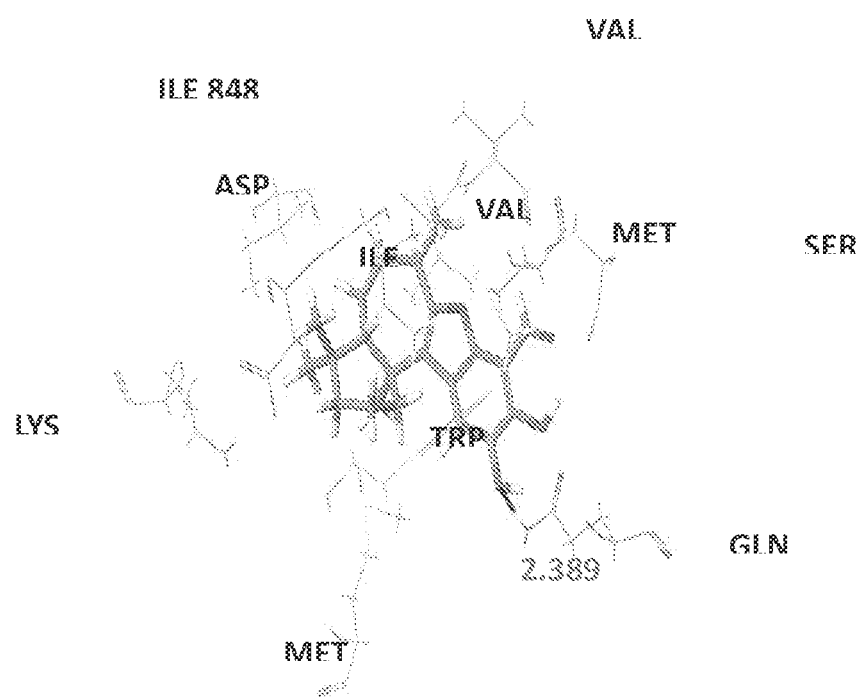
Figure 5:
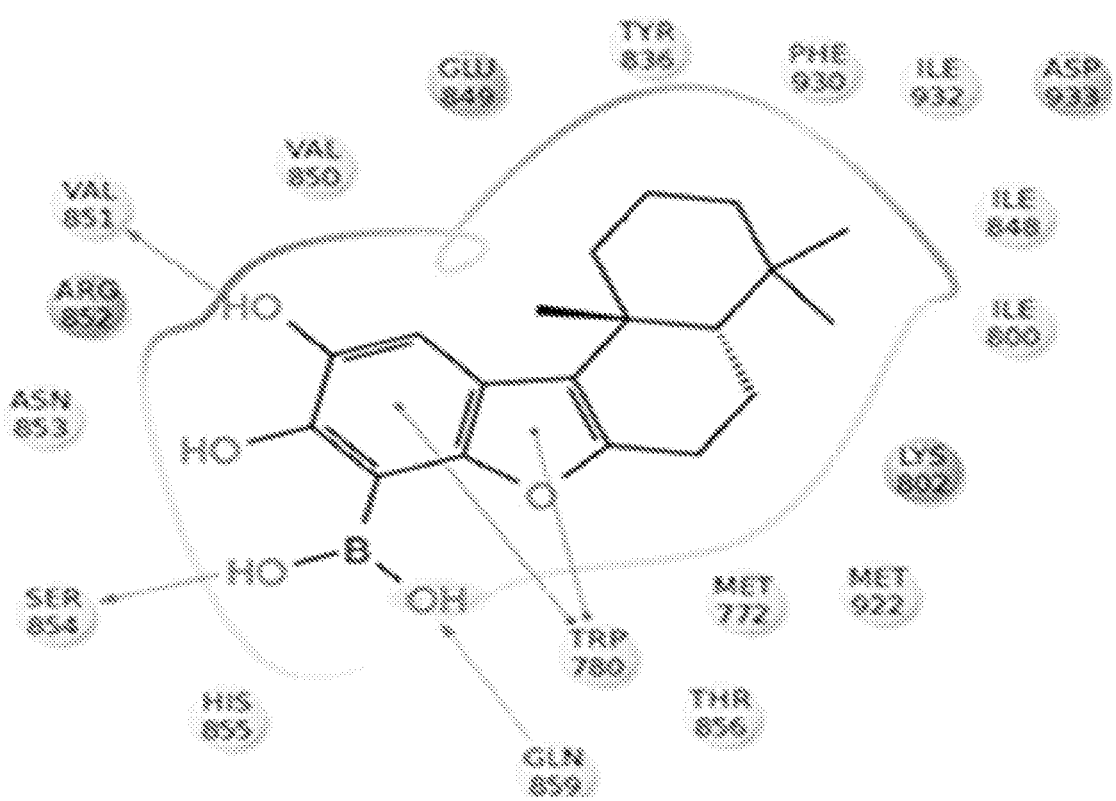

Results:

The $IC_{50}$ value of a drug measures the effectiveness of a compound in inhibiting biological or biochemical function. Drug molecules can be categorized as low, active or highly active based on $IC_{50}$ values. The determination of enzyme based $IC_{50}$ values helps in early analysis and estimation of the drug activities in order to narrow down drug candidates for further experimental purpose. The liphagal, compound A and compound E used in the present study inhibited PI3Kα enzyme activity in dose dependent pattern with varying concentration i.e 20, 40, 80, 160, 320 and 640 nM respectively. Moreover, an $IC_{50}$ of 108, 140 and 102 nM for liphagal, compound A and compound E against PI3Kα was observed and 100 nM for compound A against PI3Kβ was also determined (FIGS. 4 and 5). This approach will not only enhance origin specific cancer drug discovery process, but will also save time and resources committed.

TABLE 2

Showing $IC_{50}$ values of PI3K isoforms for compound-AZ

| Compound | PI3K ($IC_{50}$) | | | |
|---|---|---|---|---|
| AZ | α | β | γ | δ |
| | 23 nM | 5.7 μM | 85.39 μM | 303 μM |

3. Cell Cycle Analysis:

Analysis (Cell cycle (Waxman D J, Schwartz P S, Harnessing apoptosis for improved anti-cancer gene therapy, *Cancer Res.* 63:8563-8572(2003).) of a population of cells replication state can be achieved by fluorescence labeling of the nuclei of cells in suspension and then analyzing the fluorescence properties of each cell in the population. The experiment was performed using caco-2, colon human cancer cell line. Cells were seeded in 6 well plates at the concentration of $3\times10^5$ cells/ml/well. Plate was incubated in $CO_2$ incubator for overnight. After overnight incubation test sample(s) were added at desired concentration, sparing wells for negative and positive control and incubated for 24 hrs. After 24 hr incubation, cell were trypsinized along with test sample from each well was extracted using a micropippete and separately transferred into 15 ml centrifuge tubes. Tubes were centrifuged at 3000 rpm for 5 min. The supernatant was discarded and pellet was resuspended in 1 ml filtered PBS and centrifuged at 2000 rpm for 5 min. After 5 mins supernatant was discarded and pellet was resuspended in 70% ethanol. Cells were fixed for at least 1 hour at 4° C. (cells may be stored in 70% ethanol at −20° C. for several weeks prior to PI staining and flow cytometric analysis). Cells were again centrifuged at 2000 rpm for 5 minutes and washed twice in filtered PBS by centrifuging at 2000 rpm for 5 min. Supernatant was discarded and tubes were placed in inverted position over tissue paper till all the supernatant drained over the paper. 1 ml of cell cycle reagent (CCR) was added in each acquisition tube in dark. Reading was taken on flow cytometer (BD Biosciences).

Figure 6:
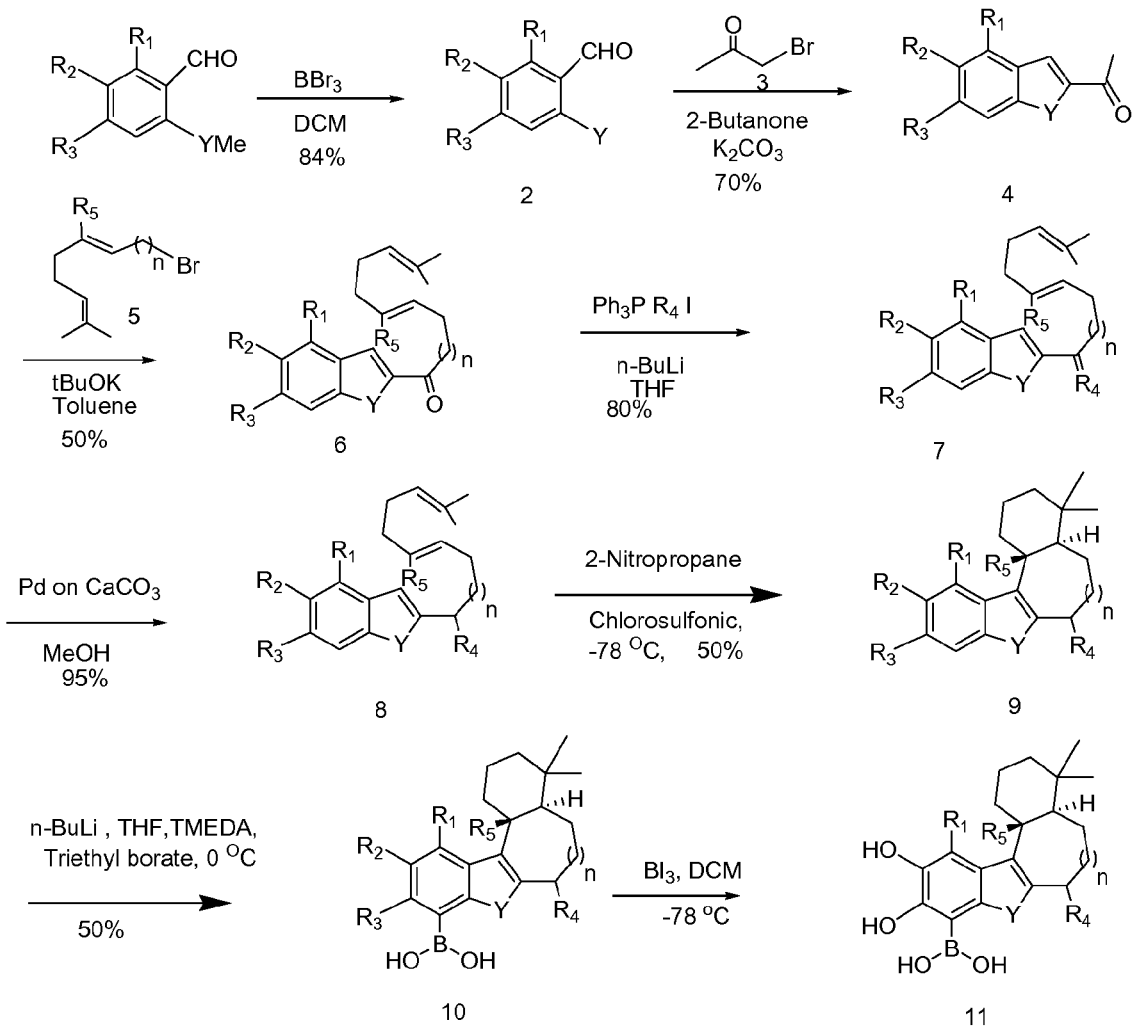

Results: Cell cycle is the life cycle of a cell. Each stage of the cell cycle i,e. G1 (Gap1), S, G2 (Gap 2), & M (mitosis) have unique events that occur within each of them. Two of the most popular flow cytometric applications are the measurement of cellular DNA content and the analysis of the cell cycle which are fundamental processes of cell survival. In the present study, the effect of compound E on the DNA content by cell cycle phase distribution was assessed by using colon (caco-2) cell line. In addition to determining the relative cellular DNA content, flow cytometry also enables the identification of the cell distribution during the various phases of the cell cycle. Cells ($2\times10^6$/ml/6-well plate), exposed to different concentrations of compound E were stained with propidium iodide (PI) to determine DNA fluorescence and cell cycle phase distribution. The percentage of compound E treated sub-G0 cells with 1, 5, 7 and 9 μM for 24 h was found to be 62.5%, 64.3%, 65.6% and 70.2% respectively. Under similar conditions, Liphagal treated cultures showed 64.9% cells in sub-G0 phase. Further, the cell cycle at G2/M phase was not affected indicating that compound E treatments does not produce any mitotic block or cause delay in cell cycle. Overall, each treatment with an increase in concentration led to an increase in sub-G0 after 24 h treatment. Thus, it is clear that compound E induced early cell cycle arrest with concentration dependent manner (FIG. 6).

4. Annexin-V Apoptotic Assay:

The cell death status was analysed using Annexin-V (Annexin-V apoptotic assay (Yunqing Li, FadilaGuessous, SherwinKwon, Manish Kumar. PTEN Has Tumor-Promoting Properties in the Setting of Gain-of-Function p53 Mutations, 2008 *Cancer Res;* 68: (6) (2008).) Flow cytometery. The experiment was performed using caco-2 colon human cancer cell line. Cells were seeded in 6 well plates at the concentration of $2\times10^5$ cells/ml/well. Plates were incubated in $CO_2$ incubator for overnight. After overnight incubation test sample(s) were added at desired concentration, sparing wells for negative and positive control and incubated for 48 hrs. After 48 hr incubation, cell were trypsinized and separately transferred into 15 ml centrifuge tubes. Tubes were centrifuged at 3000 rpm for 5 min. The supernatant was discarded and pellet was resuspended in 1 ml filtered PBS and centrifuged at 2000 rpm for 5 min. After 5 mins supernatant was discarded and pellet was resuspended in 400 ml of 1× binding buffer to make cell suspension. From this suspension, 100 μl of cells is transferred in falcon tube and then 10 μl of propidium iodide (PI) and 5 μl Annexin-V antibody were added and incubated for 30 min in dark. After 30 min incubation in dark, apoptosis were analysed by flow cytometer (BD Biosciences).

Results: In the present study, the percentage of compound E treated late apoptotic cells with 1, 5, 7 and 9 μM for 48 h was found to be 36.3%, 34.8%, 38.5% and 56.8% respectively. Under similar conditions, Liphagal treated cultures showed 42.7% cells late apoptotic phase and reverse was found in early apoptotic phase with cell population decreasing 21.9%/o, 23.4%, 21.4% and 14.7% in early apoptotic phase. Further, there were not so much population of cell in necrotic phase indicating that compound E, treatments does not produce any early apoptosis and necrosis. Overall, there was a concentration dependent net increase in late apoptotic cell population (FIG. 7).

Materials & Methods:

For immunofluorescence microscopic analysis, 4×104 CACO-2 cells/ml were seeded on 18-mm coverslips in 6-well plates, one day before experiment. Cells were serum starved overnight and treated with liphagal and compound E, 4 and 3 μM respectively for 24 hr. Following treatment, cells were washed in PBS, followed by fixation in absolute methanol at −20° C. for 5 min[19]. The fixed cells were blocked with 10% goat serum in PBS for 20 min at room temperature to eliminate non-specific binding of secondary antibody. Cells were incubated with polyclonal rabbit pAKT (serine 473) primary antibody (1:100 in 0.5% BSA in PBS; Santa Cruz Biotechnology) for 1 h at 25° C. in moist chamber, then washed and incubated with secondary antibody. The cells were washed and incubated for 45 min with a Texas red-conjugated goat antirabbit antibody (1:500 in 0.5% BSA in PBS; Santa Cruz Biotechnology) at 25° C. The coverslips were mounted on glass slides with 4',6-diamidino-2-phenylindole-containing ProLong Gold Antifade mounting medium (Invitrogen) and visualized by fluorescence microscope (Olympus, IX81) under an Olympus 60× oil immersion objective lens. The negative controls were also used in which incubation of cells with primary antibody was omitted.

Results: Phosphorylation (activation) of Akt is associated with protection of cells from apoptosis[20] (K. Nicholson, N. Anderson. 2002. The protein kinase B/Akt signaling pathway in human malignancy. *Cell signal* 14: 381-395). In the present studies it was observed that treatment of CACO-2 cells with liphagal and compound E, 4 and 3 M respectively for 24 hr caused the inhibition of pAkt (Ser 473). The inhibition of Akt consequently leads to apoptosis. The untreated cells showed the pAKT in the cytoplasm (FIG. 8).

ADVANTAGES OF THE PRESENT INVENTION

Advantages of introducing boronic acid functionality: Recent report on synthetic analog of liphagal (Alban R. Pereira, Wendy K. Strangman, Synthesis of phosphatidylinositol 3-kinase (PI3K) inhibitory analogues of the sponge meroterpenoid Liphagal; J. Med. Chem., 2010, 53 (24), pp 8523-8533) with an IC50 of 66 nM and selectivity towards PI3K-α, suggests that this analog possess greater chemical structure stability and gives opportunity for developing this skeleton into lead preclinical candidate. As a part of our ongoing program on developing isoform selective PI3K inhibitors, it occurred to us that it would be interesting to embark a program on the preparation of compounds based on this modified structure, leveraging the evidence of biological activity exhibited by this molecule. In this direction, we initiated our efforts, and planed to replace aldehyde functionality with boronic acid. Further, the 14-formyl-15,16-dihydroxy substitution pattern in the aromatic ring of liphagal is required to achieve nanomolar potency. It is also demonstrated that the absence of the C-14 formyl group appears to destabilize the liphagane heterocyclic ring system, making it more susceptible to air oxidation and skeletal rearrangements involving ring B contraction. This evidence suggests that the C-8 desmethyl analog with contracted B ring to six-membered, must be ultimately responsible for the activity, which supports our envision. Therefore, instead of formyl at the C-14, we designed a contracted B ring analog without formyl functionality having boronic acid in this place, assuming that this analog would offer more rigidity to the structure. Also, using a boronic acid instead of an aldehyde could circumvent the associated drawbacks. Moreover, boron has ability to biomimic carbon and forms the covalent adducts with the serine or histidine residues of the active site ((a) Adams, J. A.; Behnke, M.; Chen, S.; Cruichshank, A. A.; Dick, L. R.; Grenier, L.; Klunder, J. M.; Ma, Y. T.; Plamondon, L.; Stein, R. L. Bioorg. Med. Chem. Lett. 1998, 98, 333. (b) Paramore, A.; Frantz, S. Nat. Rev. Drug Discovery 2003, 2, 611).

Keeping in view the role of boron, the importance of boronic acid bearing compounds of liphagal are visualized as potential PI3K inhibitor. The evidence from the computational in silico docking of this boronic acid bearing liphagal compounds PI3K showed excellent H-bonding interactions with key amino acids, which are also previously reported as a key amino acid to be involved in inhibitory interactions in the p110α active site of PI3K-α with improved docking score of −8.08 over 1 and 2.12 The biological potential of boronic acid as PI3K inhibitor was also examined, which has shown PI3K-α isoform selectivity and excellent inhibitory activity ($IC_{50}$ 23 nM) for one of the compound i.e. compound-AZ.

We claim:

1. A compound of general formula 1, and pharmaceutically acceptable salts thereof,

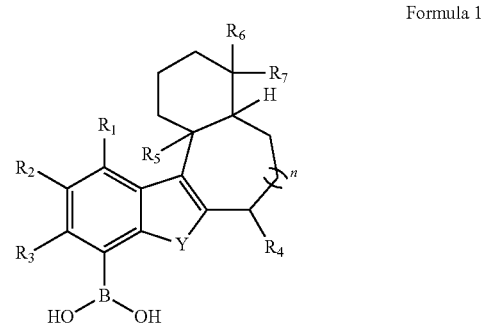

Formula 1 wherein,
a) 'Y'=O, S, NH or NR, wherein R=alkyl moiety, aryl moiety, heteroaryl moiety, cyclic aliphatic ring or an aromatic system;
b) wherein n=0 or 1;
c) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
wherein, R, R', R" are independently selected from a group consisting of alkyl moiety, aryl moiety, heteroaryl moiety and cyclic aliphatic ring,
wherein the cyclic aliphatic ring is selected from a group consisting of cyclopropyl, cyclobutyl, cyclopentyl and cyclohexyl ring and wherein the cyclic aliphatic ring has substitutions, wherein the alkyl moiety is selected from a group consisting of methyl, ethyl, propyl, isopropyl, butyl and isobutyl, and wherein the aryl or heteroaryl moiety has substitutions selected from a group consisting of halo, alkyl, nitro, amino, and sulphonyl substitutions;

d) wherein $R_4$=H or OR or SR or $SO_2R$ or $OSO_3R$ or SiRR'R" or $NH_2$ or NHR or NRR' or a saturated or unsaturated one to ten carbon chain optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R, wherein R, R', R" are independently selected from a group consisting of alkyl moiety, aryl moiety, heteroaryl moiety and cyclic aliphatic ring with substitutions, wherein the alkyl moiety is selected from a group consisting of methyl, ethyl, propyl, isopropyl, butyl and isobutyl, and wherein the aryl or heteroaryl moiety has substitutions selected from a group consisting of halo, alkyl, nitro, amino, and sulphonyl substitutions;

wherein the alkyl substituent is selected from a group consisting of methyl, ethyl, and propyl, e) wherein $R_5$ is independently selected from a group consisting of H, a $C_1$ to $C_{10}$ alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R" and R, f) wherein R6 and r7 ae independently a methyl group, wherein R, R', R" are independently selected from a group consisting of alkyl moiety, aryl moiety, heteroaryl moiety and cyclicaliphatic ring with substitutions.

2. The compound as claimed in claim 1, wherein the compound of general formula 1 is represented by compounds of formula A, B, C, D, E, F, G, H, I, J, K, L, M, N, O, P, Q, R, S, T, U, V, W, X, Y, Z, AA, AB, AC, AD, AE, AF, AG, AH, AI, AJ, AK, AL, AM, AN, AO, AP, AQ, AR, AS, AT, AU, AV, AW, AX, AY and AZ:

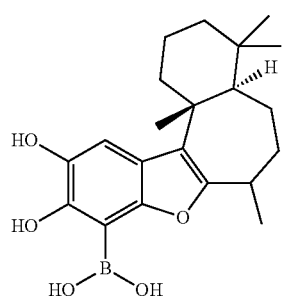

Compound A

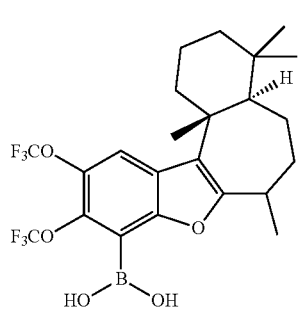

Compound B

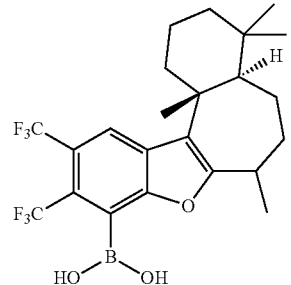

Compound C

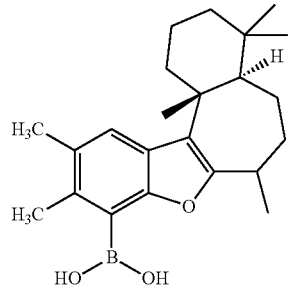

Compound D

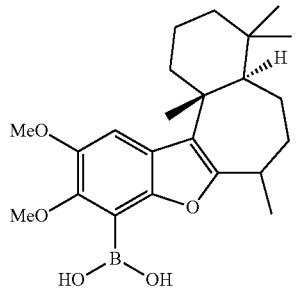

Compound E

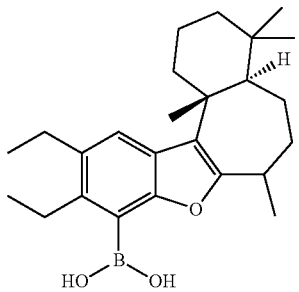

Compound F

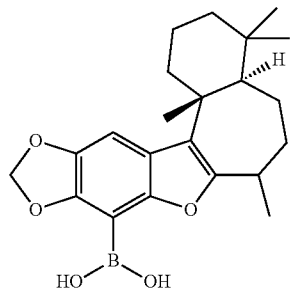

Compound G

-continued
Compound H
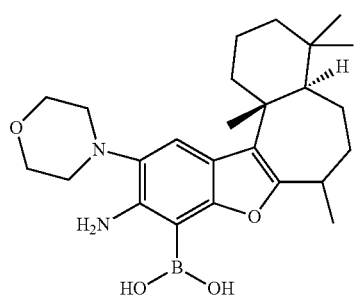
Compound I
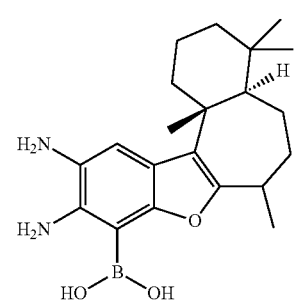
Compound J
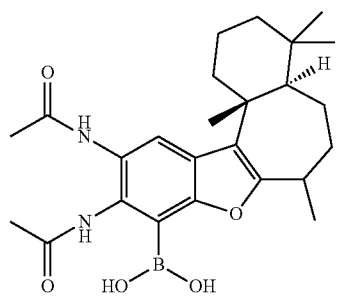
Compound K
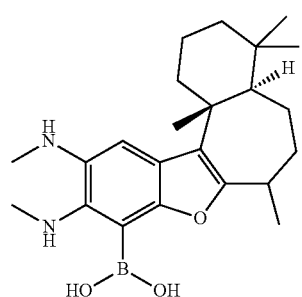
Compound L
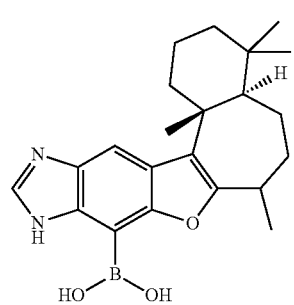
-continued
Compound M
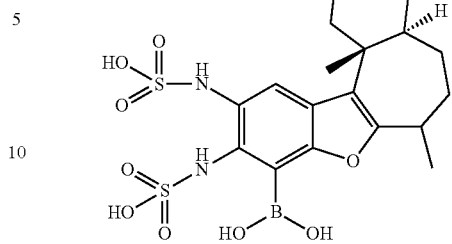
Compound N
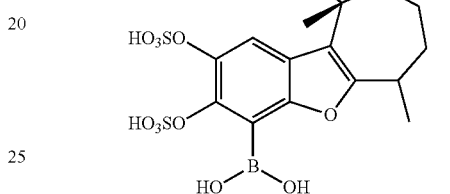
Compound O
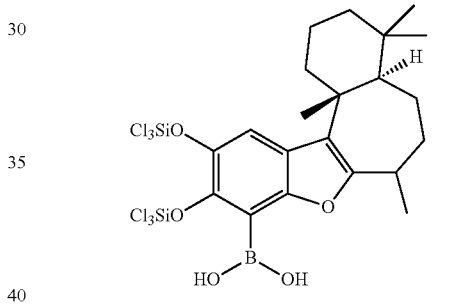
Compound P
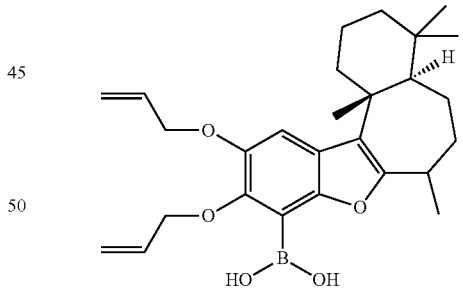
Compound Q
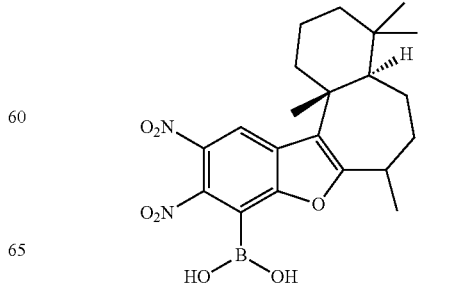

95
-continued

Compound R

Compound S

Compound T

Compound U

Compound V

96
-continued

Compound W

Compound X

Compound Y

Compound Z

Compound AA

-continued
Compound AB
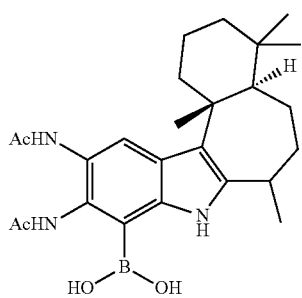
Compound AC
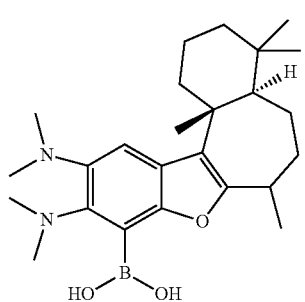
Compound AD
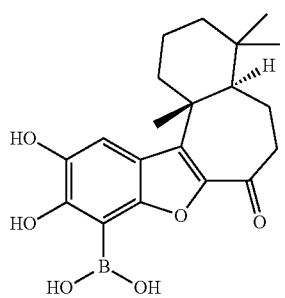
Compound AE
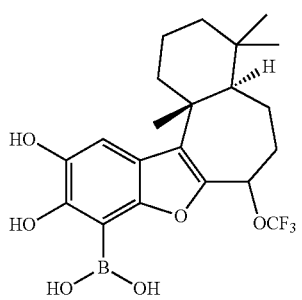
Compound AF
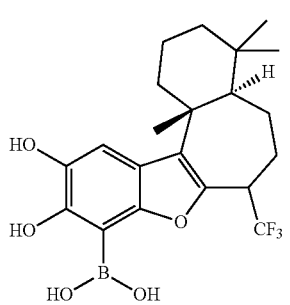
-continued
Compound AG
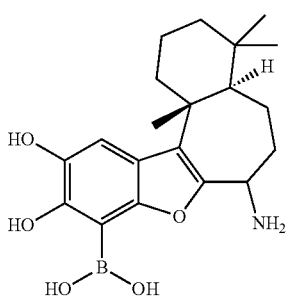
Compound AH
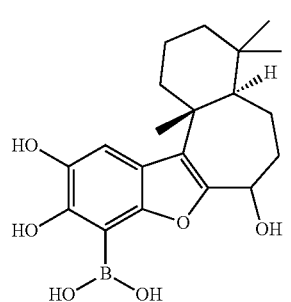
Compound AI
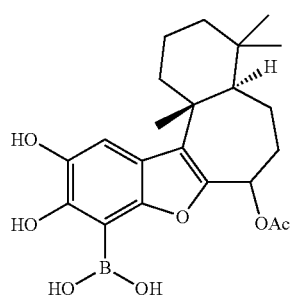
Compound AJ
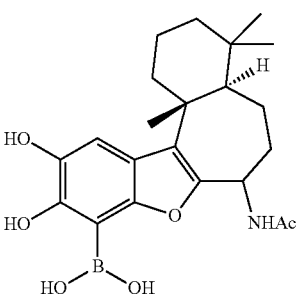
Compound AK
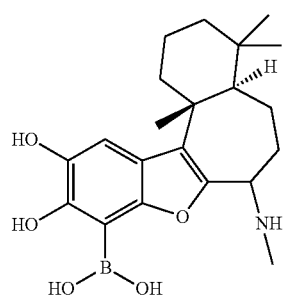

Compound AL
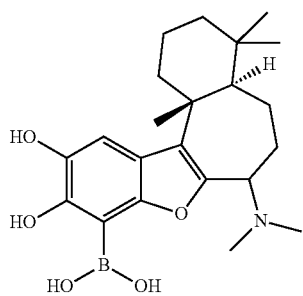
Compound AM
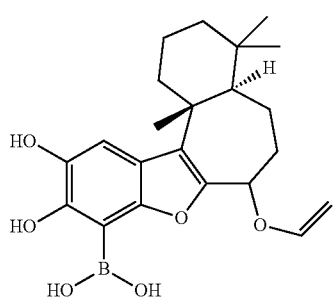
Compound AN
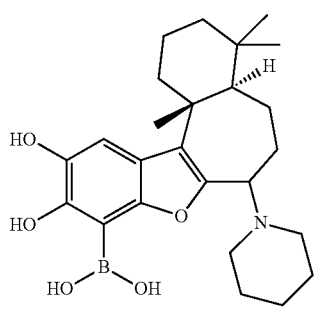
Compound AO
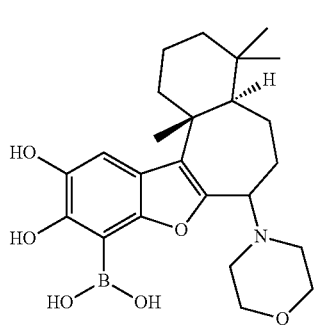
Compound AP
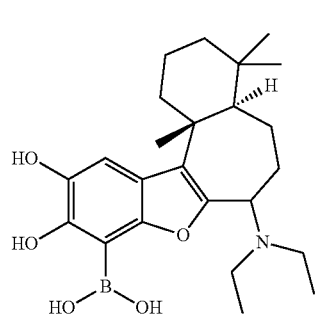
Compound AQ
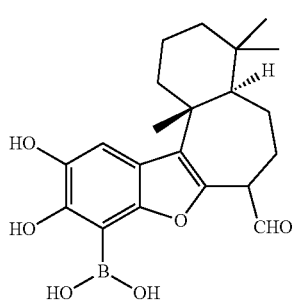
Compound AR
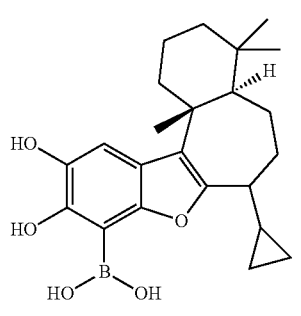
Compound AS
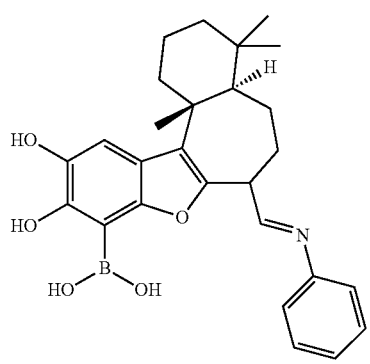
Compund AT
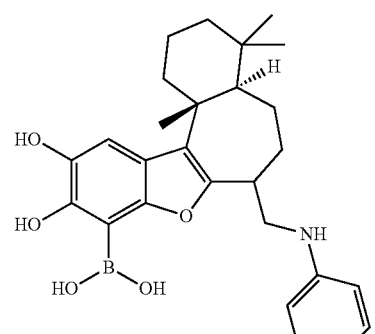
Compound AU
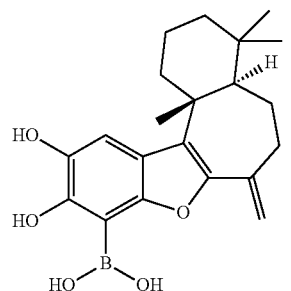

101

-continued

Compound AV

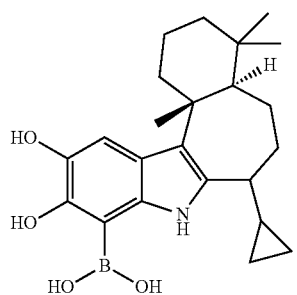

Compound AW

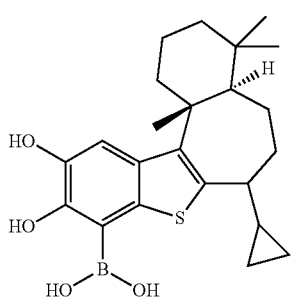

Compound AX

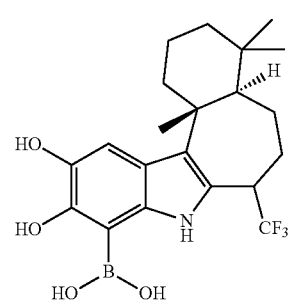

Compound AY

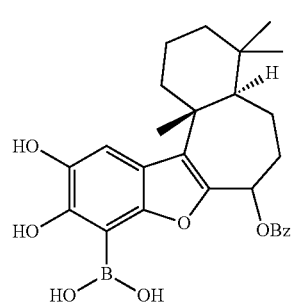

Compound AZ

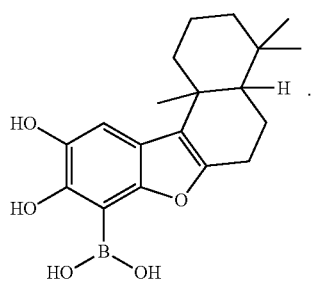

3. A process for preparation of compounds of general formula 1 and pharmaceutically acceptable salts thereof

102

Formula 1

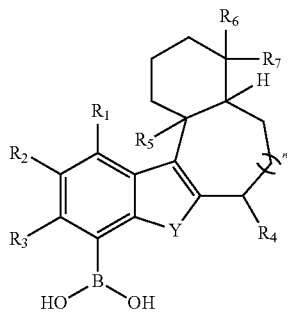

wherein,
- a) 'Y'=O, S, NH or NR, wherein R=alkyl moiety, aryl moiety, heteroaryl moiety, cyclic aliphatic ring or an aromatic system;
- b) wherein n=0 or 1;
- c) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
  wherein, R, R', R" are independently selected from a group consisting of alkyl moiety, aryl moiety, heteroaryl moiety and cyclic aliphatic ring,
  wherein the cyclic aliphatic ring is selected from a group consisting of cyclopropyl, cyclobutyl, cyclopentyl and cyclohexyl ring and wherein the cyclic aliphatic ring has substitutions,
  wherein the alkyl moiety is selected from a group consisting of methyl, ethyl, propyl, isopropyl, butyl and isobutyl,
  and wherein aryl or heteroaryl moiety has substitutions selected from a group consisting of halo, alkyl, nitro, amino, and sulphonyl substitutions;
- d) wherein $R_4$=H or OR or SR or $SO_2R$ or $OSO_3R$ or SiRR'R" or $NH_2$ or NHR or NRR' or a saturated or unsaturated one to ten carbon chain optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R,
  wherein R, R', R" are independently selected from a group consisting of alkyl moiety, aryl moiety, heteroaryl moiety and cyclic aliphatic ring with substitutions,
  wherein the alkyl moiety is selected from a group consisting of methyl, ethyl, propyl, isopropyl, butyl and isobutyl,
  and wherein aryl or heteroaryl moiety has substitutions selected from a group consisting of halo, alkyl, nitro, amino, and sulphonyl substitutions;
  wherein the alkyl substituent is selected from a group consisting of methyl, ethyl, and propyl;
- e) wherein $R_5$ is independently selected from a group consisting of H, a $C_1$ to $C_{10}$ alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R" and R,
  wherein R, R', R" are independently selected from a group consisting of alkyl moiety, aryl moiety, heteroaryl moiety and cyclic aliphatic ring with substitutions; and
- f) wherein R6 and R7 are independently a methyl group;
  wherein the process comprises the following steps:
  i) reacting compound 9 with n-butyl lithium or potassium-tert-butoxide in an ether solvent in presence of a base;

Compound 9

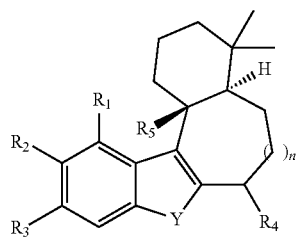

ii) adding triethyl or trimethyl borate to the mixture obtained in step (i) and stirring;
iii) quenching the reaction of step (ii) with saturated ammonium chloride solution followed by extraction with water immiscible solvent to obtain compound of general formula 10

General formula 10

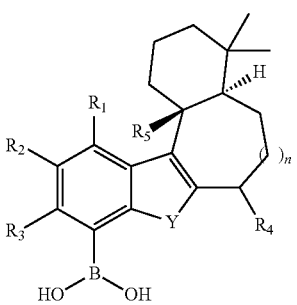

iv) reacting the compound 10 with $BI_3$ or DMS or $AlCl_3$/thiourea in a proportion in the range of 1:1 to 3:4 by moles in an ether solvent;
v) quenching the reaction of step (iv) by addition of hypo solution followed by extraction with a water immiscible solvent to obtain compound of general formula 1.

4. The process as claimed in claim 3, wherein the ether solvent used in step (i) and (iv) is selected from a group consisting of tetrahydrofuran, dichloromethane, diethyl ether, diisopropyl ether and isopropyl ether.

5. The process as claimed in claim 3, wherein the base in step (i) is selected from a group consisting of tetramethyl ethylene diamine, triethyl amine, trimethyl amine and diisopropyl ethyl amine.

6. The process as claimed in claim 3, wherein reaction in step (i) is carried out at a temperature in the range of −78° C. to 35° C. for a period ranging between 5 to 10 min.

7. The process as claimed in claim 3, wherein reaction in step (ii) is carried out at a temperature in the range of 0-5° C., for a period ranging between 1 to 2 h.

8. The process as claimed in claim 3, wherein the water immiscible solvent in step (iii) and (v) is selected from a group consisting of ethylacetate, dichloromethane, ether and chloroform.

9. The process as claimed in claim 3, wherein the reaction in step (iv) is carried out at a temperature ranging between −78° C. to 35° C. for a period ranging between 1 to 3 h.

10. The process as claimed in claim 3, wherein the compound of general formula 1 obtained in step (v) is converted into a pharmaceutically acceptable salt.

11. The process as claimed in claim 10, wherein the compound of general formula 1 is converted into a pharmaceutically acceptable salt by a process comprising the steps of mixing the compound of general formula 1 with a base in a ratio 1:1 proportion, wherein the base is selected from a group consisting of sodium hydroxide, potassium hydroxide and ammonium hydroxide in water, stirring the reaction mixture for 1-2 h followed by drying to obtain the pharmaceutically acceptable salt of the compound of general formula 1.

12. A pharmaceutical composition comprising the compound of formula 1, optionally along with a pharmaceutically acceptable carrier, salt, excipient or diluent.

13. The pharmaceutical composition as claimed in claim 12, wherein the pharmaceutically acceptable carrier is selected from a group consisting of water, buffered saline, glycols, glycerols, olive oil and liposomes.

14. A method of treatment of cancer by specific inhibition of PI3K-α or β isoform in a human cancer cell line using a compound of general formula 1,

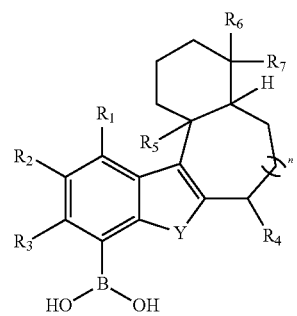

wherein,
a) 'Y'=O, S, NH or NR, wherein R=alkyl moiety, aryl moiety, heteroaryl moiety, cyclic aliphatic ring or aromatic system;
b) wherein n=0 or 1;
c) wherein $R_1$, $R_2$ and $R_3$ are independently selected from a group consisting of H, OH, OR, COR, CHO, $CO_2R$, OCOR, $NH_2$, NHR, NR, NRR', $NO_2$, F, Cl, Br, I, $OSO_3H$, $SO_2R$, CN, SiRR'R", $OCF_3$, $CF_3$ and R,
wherein, R, R', R" are independently selected from a group consisting of alkyl moiety, aryl moiety, heteroaryl moiety and cyclic aliphatic ring,
wherein the cyclic aliphatic ring is selected from a group consisting of cyclopropyl, cyclobutyl, cyclopentyl and cyclohexyl ring and wherein the cyclic aliphatic ring has substitutions,
wherein the alkyl moiety is selected from a group consisting of methyl, ethyl, propyl, isopropyl, butyl and isobutyl,
and wherein aryl or heteroaryl moiety has substitutions selected from a group consisting of halo, alkyl, nitro, amino, and sulphonyl substitutions;
d) wherein $R_4$=H or OR or SR or $SO_2R$ or $OSO_3R$ or SiRR'R" or $NH_2$ or NHR or NRR' or a saturated or unsaturated one to ten carbon chain optionally substituted with OH, H, =O, =S, OR, COR, CHO, $CO_2R$, OCOR, $NH_2$, NHR, NRR', $NO_2$, F, Cl, Br, I, $OSO_3H$, $SO_2R'$, CN, SiRR'R" or R,
wherein R, R', R" are independently selected from a group consisting of alkyl moiety, aryl moiety, heteroaryl moiety and cyclic aliphatic ring with substitutions, wherein the alkyl moiety is selected from a group consisting of methyl, ethyl, propyl, isopropyl, butyl and isobutyl, and wherein aryl or heteroaryl moiety has substitutions selected from a group consisting of halo, alkyl, nitro, amino, and sulphonyl substitutions;

wherein the alkyl substituent is selected from a group consisting of methyl, ethyl, and propyl;

e) wherein $R_5$ is independently selected from a group consisting of H, a $C_1$ to $C_{10}$ alkyl group, wherein the alkyl group is optionally substituted with OH, H, =O, =S, OR, COR, CHO, $CO_2R$, OCOR, $NH_2$, NHR', NRR', $NO_2$, F, Cl, Br, I, $OSO_3H$, $SO_2R$, CN, SiR'R'R'' and R, wherein R, R', R'' independently selected from a group consisting of alkyl moiety, aryl moiety, heteroaryl moiety and cyclic aliphatic ring with substitutions; and, f) wherein $R_6$ and $R_7$ are independently a methyl group;

wherein the method comprises: mixing the compound of general formula 1 and a human cancer cell line selected from a group consisting of a lung cell line (A549), a leukemia cell line (THP1), a prostrate cell line (PC-3) and a colon cell line (caco-2, colo205, HCT-115), and specifically inhibiting PI3K-α or β isoform in the human cancer cell line.

15. The method as claimed in claim 14, wherein the dosage of compound of general formula 1 is in the range of 20 mg/kg to 100 mg/kg.

16. The method as claimed in claim 14, wherein the representative compound of Formula A has a GI50 concentration in the range of 2.4 μM-2.6 μM when used for in vitro activity against colon and breast cancer cell lines.

17. The method as claimed in claim 14, wherein the representative compound of Formula A demonstrates >74% optimal growth inhibition in human cancer cell lines at a concentration of 10 μM.

18. The method as claimed in claim 14, wherein the representative compound of Formula E when used for in vitro activity against colon cancer cell lines increases sub-G1/G0 population and shows concentration dependent growth arrest in G1/G0 population and late apoptosis in colon cancer cell lines.

* * * * *